(12) United States Patent
Arbabian et al.

(10) Patent No.: US 10,014,570 B2
(45) Date of Patent: Jul. 3, 2018

(54) SINGLE TRANSDUCER FOR DATA AND POWER IN WIRELESSLY POWERED DEVICES

(71) Applicant: The Board of Trustees of the Leland Stanford Junior University, Palo Alto, CA (US)

(72) Inventors: Mohammad Amin Arbabian, San Francisco, CA (US); Marcus J. Weber, Palo Alto, CA (US); Jayant Charthad, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 15 days.

(21) Appl. No.: 15/371,648

(22) Filed: Dec. 7, 2016

(65) Prior Publication Data

US 2017/0125892 A1 May 4, 2017

Related U.S. Application Data

(63) Continuation-in-part of application No. 14/276,827, filed on May 13, 2014, now Pat. No. 9,544,068.
(Continued)

(51) Int. Cl.
*G08C 19/10* (2006.01)
*H01Q 1/27* (2006.01)
(Continued)

(52) U.S. Cl.
CPC ........... *H01Q 1/273* (2013.01); *A61B 5/0024* (2013.01); *A61B 5/0028* (2013.01); *A61B 5/686* (2013.01);
(Continued)

(58) Field of Classification Search
CPC ....... H01Q 1/273; H01Q 1/2291; H02J 50/20; H02J 7/025; H02J 7/345; H02J 17/00;
(Continued)

(56) References Cited

U.S. PATENT DOCUMENTS

| | | | |
|---|---|---|---|
| 9,197,143 B1* | 11/2015 | Townsend | H02J 1/108 |
| 2014/0021825 A1* | 1/2014 | Ocalan | H02N 11/002 |
| | | | 310/300 |
| 2014/0162729 A1* | 6/2014 | Garden | H04B 1/3888 |
| | | | 455/566 |

* cited by examiner

*Primary Examiner* — Tesfaldet Bocure
(74) *Attorney, Agent, or Firm* — Lumen Patent Firm

(57) ABSTRACT

A wireless powering and communication system is provided that includes a base unit, and an external unit that is separate from the base unit, where the base unit includes a single transducer circuit configured for uplink data communication to the external unit, where the transducer circuit is configured for power recovery from the external unit, a multiplexer circuit, a power recovery and conditioning circuit, a controller circuit, and a communication circuit, where the multiplexer circuit is configured to decouple power and data paths to enable operation with the single transducer circuit, the power recovery and conditioning circuit is configured to recover and optionally store power from power received by the single transducer circuit, the power recovery and conditioning circuit is configured to power the controller circuit and the communication circuit, the controller circuit is configured to control the multiplexer circuit, the communication circuit is configured to provide data to the multiplexer circuit.

19 Claims, 35 Drawing Sheets

Related U.S. Application Data

(60) Provisional application No. 61/822,763, filed on May 13, 2013, provisional application No. 62/405,466, filed on Oct. 7, 2016.

(51) Int. Cl.
| | |
|---|---|
| *H01Q 1/22* | (2006.01) |
| *H04B 5/00* | (2006.01) |
| *A61B 5/00* | (2006.01) |
| *H02J 7/02* | (2016.01) |
| *H04B 11/00* | (2006.01) |
| *H04B 13/00* | (2006.01) |
| *H02J 50/20* | (2016.01) |
| *A61B 5/01* | (2006.01) |
| *A61B 5/053* | (2006.01) |
| *A61B 5/11* | (2006.01) |
| *A61B 5/145* | (2006.01) |
| *H02J 7/34* | (2006.01) |

(52) U.S. Cl.
CPC ........... *H01Q 1/2291* (2013.01); *H02J 7/025* (2013.01); *H02J 50/20* (2016.02); *H04B 5/0081* (2013.01); *H04B 11/00* (2013.01); *H04B 13/005* (2013.01); *A61B 5/0017* (2013.01); *A61B 5/0071* (2013.01); *A61B 5/0084* (2013.01); *A61B 5/01* (2013.01); *A61B 5/0538* (2013.01); *A61B 5/11* (2013.01); *A61B 5/14503* (2013.01); *A61B 2560/0219* (2013.01); *H02J 7/345* (2013.01)

(58) Field of Classification Search
CPC ... A61B 5/0024; A61B 5/0028; A61B 5/0071; A61B 5/01; A61B 5/0084; A61B 5/11; A61B 5/0538; A61B 5/0017; A61B 2560/02; A61B 5/686; H04B 5/0081; H04B 11/00; H04B 13/005
USPC .................................................... 340/870.11
See application file for complete search history.

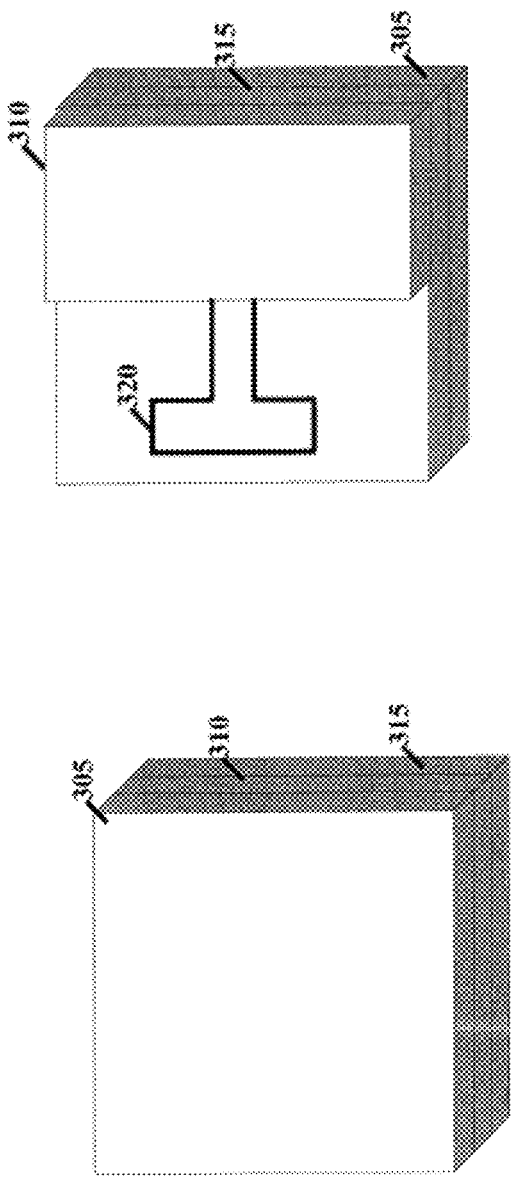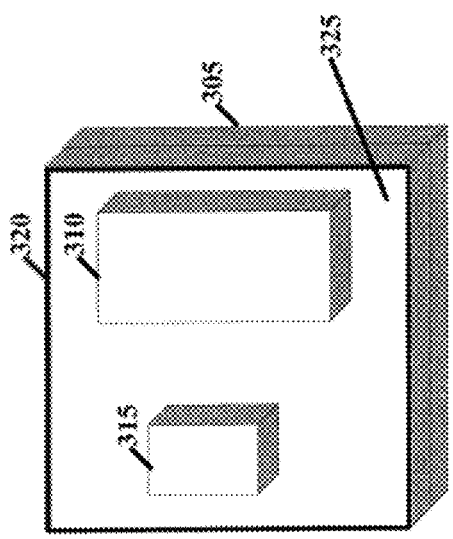
FIG. 3B
FIG. 3C
FIG. 3A

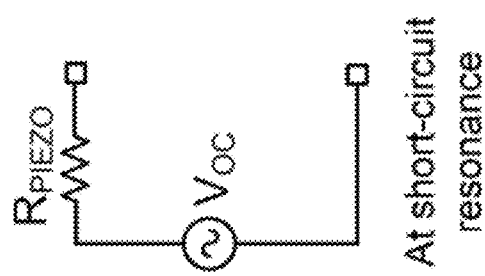
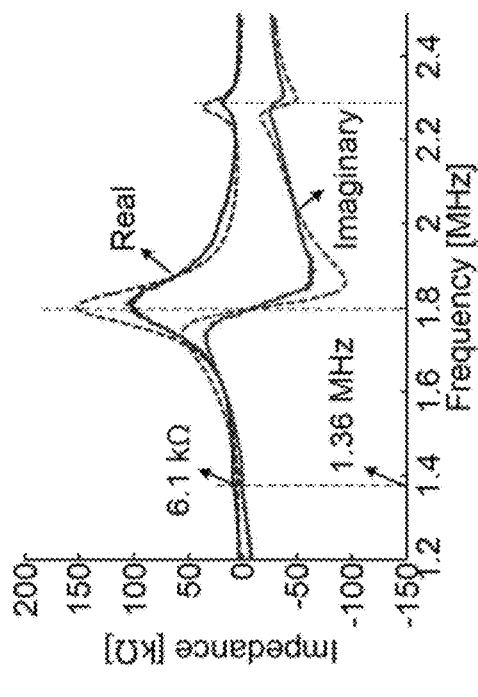
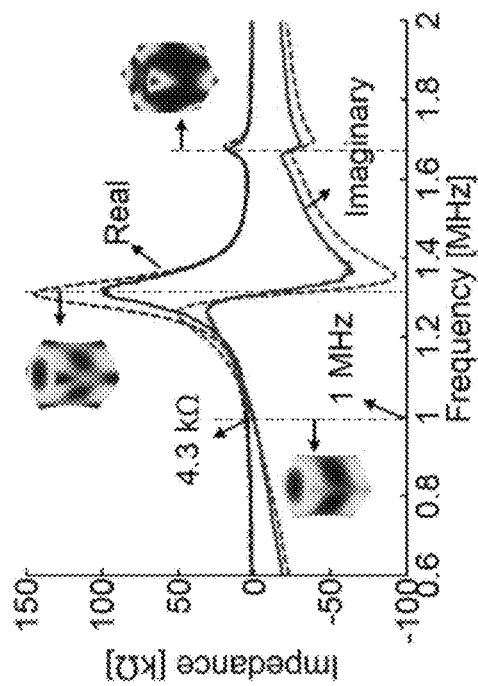
FIG. 11A
FIG. 11B
FIG. 11C

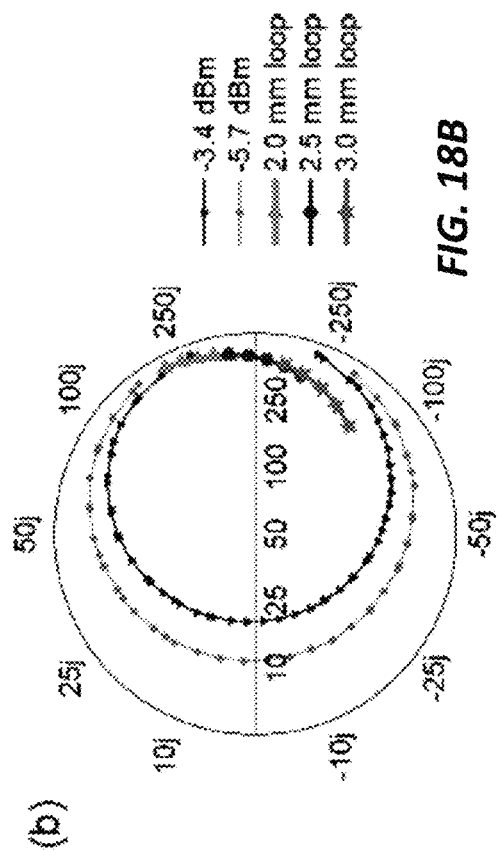
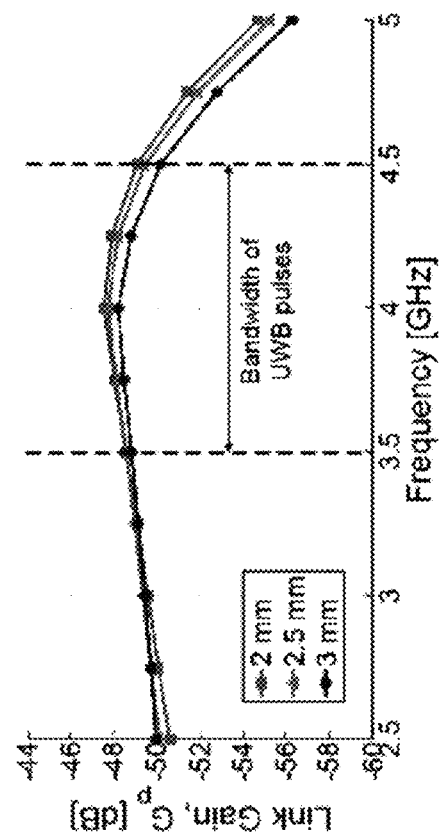
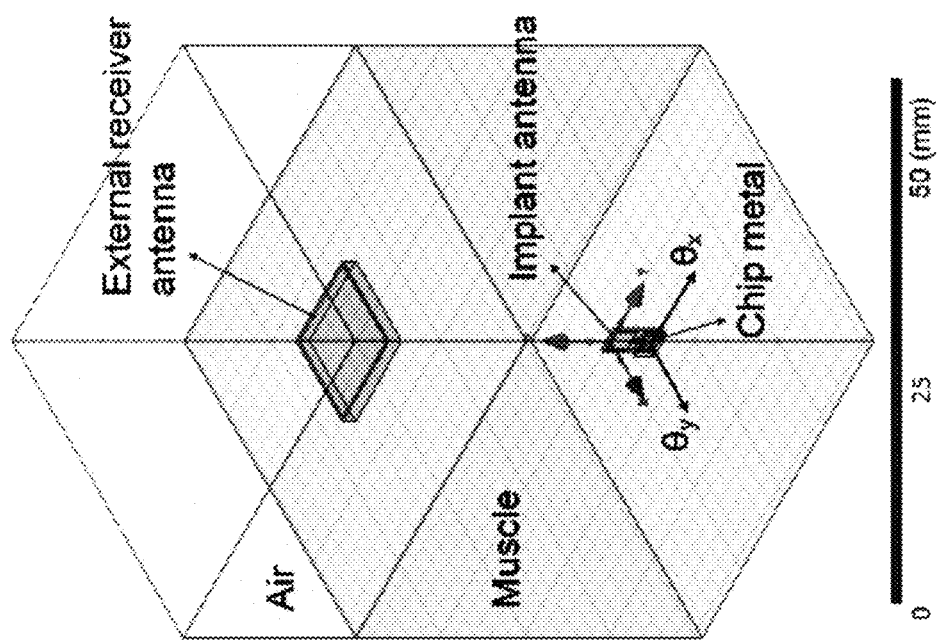
FIG. 18B
FIG. 18C
FIG. 18A $$P_{TX} > P_{thermal} + 10\log(BW) + SNR + L_{amp} + L_{freespace} + L_{body} + L_{other} - G_{TX} - G_{RX}$$
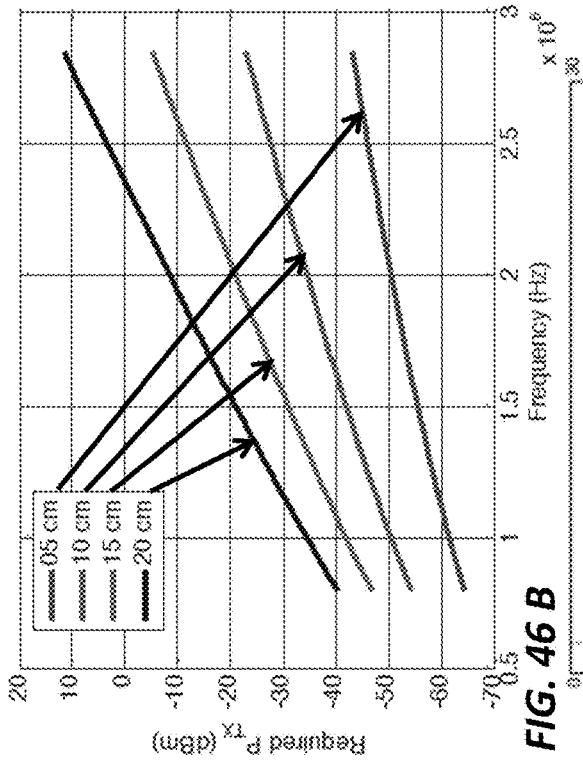
FIG. 46 B
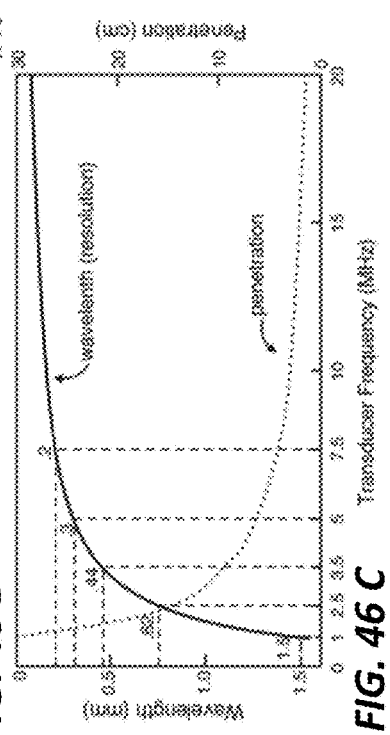
FIG. 46 C
| | |
|---|---|
| $P_{thermal}$ | -174 dBm |
| BW | ~ 100 kHz |
| SNR | ~ 15 dB |
| $L_{amp}$ | ~ 10 dB |
| $L_{freespace}$ | ~ 30-50 dB ($\lambda^2/4*pi$) |
| $L_{body}$ | ~ 1 dB/cm/MHz |
| $L_{other}$ | ~ 3 dB (reflection etc) |
| $G_{TX}$ | ~ 3 dB |
| $G_{RX}$ | ~ 20 dB* |
Sim at 1MHz for 1cm² ~24dB (oil)
Sim at 3MHz for 1cm² ~30dB (oil)
Max operating frequency ~3MHz for 10-15cm
FIG. 46 A

SINGLE TRANSDUCER FOR DATA AND POWER IN WIRELESSLY POWERED DEVICES

CROSS-REFERENCE TO RELATED APPLICATIONS

This application claims priority from U.S. Provisional Patent Application 62/405,466 filed Oct. 7, 2016, which is incorporated herein by reference. This application is a continuation-in-part of U.S. patent application Ser. No. 14/276,827 filed May 13, 2014 now issued as U.S. Pat. No. 7,544,068 on Jan. 10, 2017, which is incorporated herein by reference. U.S. patent application Ser. No. 14/276,827 claims priority from U.S. Provisional Patent Application 61/822,763 filed May 13, 2013, which is incorporated herein by reference.

FIELD OF THE INVENTION

The present invention relates generally to wirelessly powered devices. More particularly, the invention relates to wirelessly powered devices having a single transducer for power recovery and "active" uplink communication.

BACKGROUND OF THE INVENTION

For many applications of wirelessly powered nodes, such as internet of things (IoT) or biomedical applications, aggressive miniaturization of the device is critical. Miniaturization is important for biocompatibility (in the case of implantable devices), reducing the cost, ease of fabrication and better reliability of these devices. Typically, different transducers (more than one) are used in wirelessly powered devices for recovering wireless power, and for bi-directional communication with external device(s). Using more than one transducer can increase the size and cost of these devices, and poses a challenge for their miniaturization. The current invention relates to using a single transducer for several functions, mainly for wireless power recovery as well as bi-directional data communication.

Wirelessly-powered, highly-miniaturized implantable medical devices (IMDs) can play a crucial role in eliminating the invasiveness and discomfort caused by batteries and wires in most traditional implants. Miniaturization of implants to mm and sub-mm dimensions can also open up the possibility of having a network of sensor nodes in body for applications such as multisite neural recording and stimulation. However, there exists in the art the engineering problem of efficiently delivering 100's of μW to a few mWs, to depths near ~10 cm in the body, for miniaturized implants in demanding applications such as: deep brain stimulation (DBS), optogenetics and peripheral nerve stimulation. Besides powering of the implant, many applications would benefit from a bi-directional communication link for control functions and data uplink, and all of this functionality needs to be implemented into a small package for practicality.

SUMMARY OF THE INVENTION

To address the needs in the art, a wireless powering and communication system is provided that includes a base unit, and an external unit, where the external unit is separate from the base unit, where the base unit includes a single transducer circuit with a single port or feed, configured for uplink data communication to the external unit, where the transducer circuit is configured for power recovery from the external unit, a multiplexer circuit, a power recovery and conditioning circuit, a controller circuit, and a communication circuit, where the multiplexer circuit is configured to decouple power and data paths to enable operation with the single transducer circuit, where the power recovery and conditioning circuit is configured to recover and optionally store power from power received by the single transducer circuit, where the power recovery and conditioning circuit is configured to power the controller circuit and the communication circuit, where the controller circuit is configured to control the multiplexer circuit, where the communication circuit is configured to provide data to the multiplexer circuit.

According to one aspect of the invention, the external unit is configured to detect backscatter signals, where the base unit further includes a load circuit configured to provide different loads to the transducer circuit during active backscatter communication with the backscatter configured external unit. In one aspect where the load circuit includes an active load circuit that is powered from the power recovery and conditioning circuit.

In another aspect of the invention, the power recovery and conditioning circuit is configured to power the multiplexer circuit.

In a further aspect of the invention, the base unit is implantable to a biological host.

In yet another aspect of the invention, the multiplexer circuit includes a circulator having a first port, a second port and a third port, where a power signal enters the first port from the transducer circuit, where the power signal exits the circulator from the second port and enters the power recovery and conditioning circuit, where a data signal enters the third port from the communication circuit, where the data signal exits the first port and enters the transducer circuit. The circulator can either be a conventional circulator, or a non-magnetic circulator, including but not limited to an active circulator.

According to another aspect of the invention, the single transducer circuit includes a capacitive micromachined ultrasound transducer (CMUT), which could either be precharged or not, a piezoelectric micromachined ultrasound transducer (PMUT), an electro magnetic acoustic transducer (EMAT), an electret, a piezoelectric transducer, an RF antenna, a capacitive energy coupler, an inductive coil, or an optical transducer.

In a further aspect of the invention, the power and data are transmitted at different resonance frequencies, off-harmonic frequencies or intermediate frequencies in an inductive band of the transducer circuit.

In one aspect of the invention, the multiplexer circuit includes a fixed matching network or filter, or includes a reconfigurable matching network or filter.

In yet another aspect of the invention, the power and data are transmitted at different amplitudes and the multiplexer circuit decouples power and data paths based on the different amplitudes.

According to another aspect of the invention, the multiplexer circuit includes a first transmit switch block and a first receive switch block, where when transmit switch block is closed, data is communicated from the communication circuit to the transducer circuit, where when the receive switch block is closed, power is transferred from the transducer circuit to the power recovery and conditioning circuit. In one aspect the first transmit switch block and the first receive switch block are driven by the controller circuit. In another aspect, the base unit further includes a downlink receiver circuit, where when a second receive switch block is closed, data is communicated from the transducer to the downlink receiver circuit.

In a further aspect of the invention, the base unit further includes a sensor, where the sensor is configured for temperature, pressure, chemical, pH, impedance, or aptamer-based sensing, electrical or electrophysiological sensing including but not limited to neural, EMG or ECG recording, or detecting biological species such as: proteins, DNA, biomolecules, or biomarkers.

According to another aspect of the invention, the base unit further includes a stimulator circuit, where the stimulator circuit is configured for electrical, optical or acoustic stimulation, or the release of a chemical, a drug or a biological agent.

In a further aspect of the invention, the multiplexer circuit includes wires directly connected between the transducer circuit, the power recovery and conditioning circuit, and the communication circuit.

According to one aspect of the invention, the base unit further includes a downlink receiver circuit, where downlink data is communicated from the multiplexer circuit to the downlink receiver circuit, where the downlink receiver circuit receives power from the power recovery and conditioning circuit, where the downlink receiver circuit sends data to the controller circuit.

In another aspect of the invention, the base unit further includes a low-power auxiliary power block, where the low-power auxiliary power block is configured to recover power from the single transducer circuit before the power recovery and conditioning circuit can fully turn on, where the low-power auxiliary power block is configured for partially or fully powering a component selected from the group consisting of the multiplexer circuit, the controller circuit, the power recovery and conditioning circuit, and the communication circuit. In one aspect, the low-power auxiliary power block is also configured to recover power from the single transducer circuit during the time when the power recovery and conditioning circuit is on.

BRIEF DESCRIPTION OF THE DRAWINGS

FIGS. 3A-3C show example base units, according to various aspects of the current invention.

FIGS. 11A-11C shows a simulated (dashed line) and measured (solid line) impedance of (a) 1 mm×1 mm×1.4 mm, and (b) 0.7 mm×0.7 mm×1.0 mm piezoelectric devices, also showing the displacement profiles of the 1.4 $mm^2$ piezoelectric device at the resonance frequencies, (c) Equivalent circuit model of the piezoelectric device at short-circuit resonance frequency, according to embodiments of the current invention.

FIGS. 18A-18C show (a) HFSS simulation setup for the antenna showing tissue modeled as muscle (muscle has high losses and gives conservative link gain results), antenna feed, bondwires, and IC modeled as a metal sheet. (b) Simulated load-pull curves of the PA superimposed with the simulated impedance for different antenna dimensions. (c) Simulated link gain, $G_P$, showing a flat gain profile between 3.5-4.5 GHz for all antenna sizes, according to embodiments of the current invention.

FIGS. 46A-46C show an example link budget calculation for ultrasonic "active" data uplink, according to the current invention.

DETAILED DESCRIPTION

Figure 1:
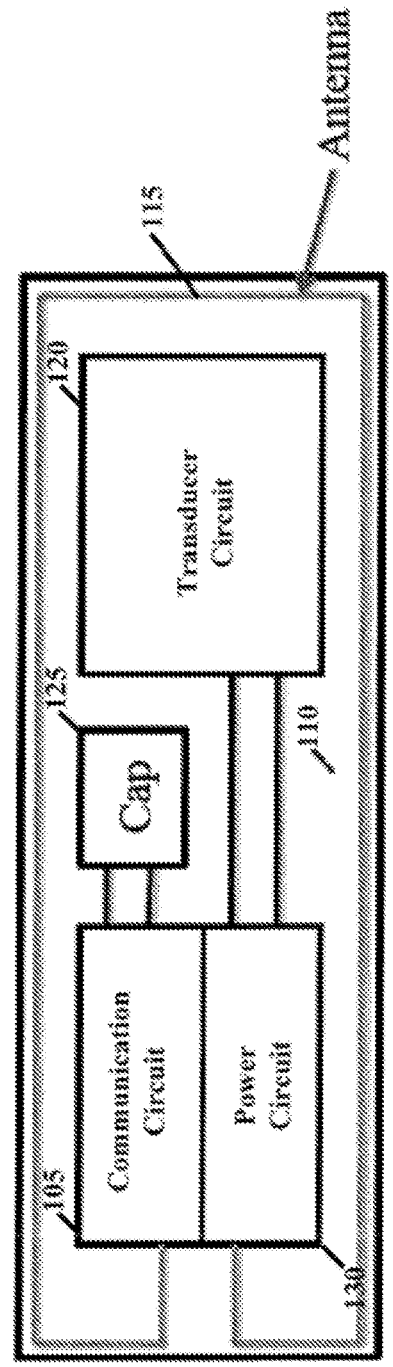
FIG. 1 shows a block diagram of an example base unit, according to various aspects of the current invention.

The present invention is directed to data transfer and powering between a device that is external to a patient and one or more low-power devices (which can include one or more sensors) that are implanted in the patient. By utilizing a combination of ultrasound (US) signals to power the low-power devices via an external device, the low-power devices can communicate with the external device using US and/or RF, which avoids degradation of the signals due to tissue (which can increase with signal frequency). In this manner, an effective amount of energy from the power signals provided to the low-power devices can be captured due to the dimensions of the power signals' wavelength. Such low-power devices can be used as medical implants for applications such as: pacemakers, glucose or electrolyte monitoring, neural recording, optogenetics (implanted sensors that emit light locally and can be programmed wirelessly), deep brain stimulation, peripheral nerve stimulation with implants (muscle or brain), pressure and/or temperature monitoring, blood pressure modulation, imaging, artificial organs, swallowable pill applications and cardiac mapping. While the present disclosure is not necessarily limited to such applications, various aspects of the disclosure may be appreciated through a discussion of various examples using this data transfer and powering context.

Various aspects of the present disclosure are directed toward apparatuses that include a base unit and a communication circuit that communicate, while implanted in a patient, signals between the patient and at least one device located external to the patient. The apparatuses can include an electrical circuit that is secured by the base unit. The electrical circuit includes an antenna, at least one transducer, a capacitor circuit, and a power circuit. The antenna is configured with the communication circuit to communicate RF signals between the base unit and the at least one device located external to the patient. The RF signals can also include downlink data from the device located external to the patient. The transducer communicates US signals between the base unit and the at least one device located external to the patient, and harvests energy carried by the US signals. The capacitor circuit stores the energy harvested by the transducer, and the power circuit powers-up the base unit based on the energy harvested by the transducer and stored by the capacitor circuit. Further, the base unit prompts the communication circuit to transmit signals characterizing the patient's biological or physiological attribute, via the antenna, to the at least one device located external to the patient.

Additionally, the communication circuit can also transmit the signals using a pulse-based communication scheme that includes periodic bursts of energy, that last less than 100 nanoseconds, at RF or microwave frequencies that are between 0.1 GHz and 10 GHz. In other embodiments, the pulsed-based communication scheme includes utilizing at least one of pulse position modulation (PPM), multi-PPM, pulse-amplitude modulation (PAM), and pulse width modulation (PWM). Further, in certain embodiments, the base unit also includes: an oscillator circuit that generates the pulse-based signals (e.g., an LC oscillator or ring-oscillator), a pulser circuit that modulates the pulse-based signals, and a power amplifier circuit that buffers the pulse-based signals and transmits the pulse-based signals via the antenna. Moreover, in other embodiments, the signals characterizing the patient's biological or physiological attribute are transmitted as active pulse signals, and the base unit also includes: an oscillator circuit that generates the active pulse transmission signals, a pulser circuit that modulates the active pulse transmission signals, and a power amplifier circuit that buffers the active pulse transmission signals and transmits the pulse-based signals via the antenna.

Certain apparatuses, methods, and systems also include the device being located external to the patient. Additionally, in certain embodiments, the base unit is arranged and sized to communicate with the device located external to the patient and other base units (that are similarly constructed) using a combination of RF and US signals. The base units and the device external to the patient can be synchronized based on communication notches in the US signal that are used to calibrate and correct for mismatch, delay, skew, or jitter in communication between the base units and the external device. The base unit can also include a light-emitting diode (LED) (or a laser diode) or other light source, and the power circuit powers-up the LED based on the energy stored by the capacitor circuit and activates the laser diode periodically or based on a pattern that is communicated to the base unit via the downlink data. Moreover, the base unit can include one or more of a chemical sensor, an impedance sensor, a fluorescence sensor, an optical sensor, temperature sensor, electrical voltage or spike sensors, and a vibrational sensor. In such embodiments, the power circuit powers-up and activates operational aspects of the sensor(s) included with the base unit. Additionally, in these embodiments, the base unit can use RF frequencies to transmit the pulse-based signals and uplink communication data indicative of the operation of the sensor from the base unit to the device located external to the patient. Moreover, in certain embodiments, the device located external to the patient transmits further downlink communication data indicative of a further operation of the sensor in response to receiving the uplink communication data indicative of the operation of the sensor from the base unit to the device located external to the patient.

In certain embodiments, the antenna, the transducer, the capacitor circuit, and the power circuit are provided as part of a silicon chip or integrated circuit. Additionally, in other embodiments, the transducer and the power circuit are provided as part of a silicon chip (or integrated circuit), and the antenna and the capacitor circuit are provided external to the silicon chip (or integrated circuit). Further, the capacitor circuit can include a piezoelectric or capacitive micro-machined transducer, and, in such embodiments, the US signal is converted into electrical energy, via the piezoelectric or the capacitive micro-machined transducer, and stored in the capacitor circuit.

The embodiments and specific applications discussed herein may be implemented in connection with one or more of the above-described aspects, embodiments and implementations, as well as with those shown in the appended figures.

Turning now to the figures, FIG. 1 shows a block diagram of an example base unit 100 and communication circuit 105, consistent with various aspects of the present disclosure. The base unit 100 includes a communication circuit 105. The base unit 100 and the communication circuit 105 communicate, while implanted in a patient, signals between the patient and at least one device located external to the patient (e.g., as shown and discussed in further detail with reference to FIG. 4). Additionally, the base unit 100 also includes an electrical circuit 110 that is secured by the base unit 100. As shown in FIG. 1, the electrical circuit 110 can include an (optional) antenna 115 that is configured to the communication circuit 105 to communicate RF signals between the base unit 100 and the at least one device located external to the patient. The RF signals include downlink data from the device located external to the patient. The downlink data can also be carried over US signals. The electrical circuit 110 also includes a transducer circuit 120 that communicates US signals between the base unit 100 and the at least one device located external to the patient, and also harvests energy carried by the US signals. Further, the electrical circuit 110 includes a capacitor circuit 125 that stores the energy harvested by the transducer circuit 120. The electrical circuit 110 also includes a power circuit 130 that powers up the base unit 100, based on the energy harvested by the transducer circuit 120 and stored by the capacitor circuit 125. Additionally, the power circuit 130 prompts the communication circuit to transmit signals characterizing the patient's biological or physiological attribute, via the antenna 115, to the at least one device located external to the patient. As discussed below in connection with FIG. 3, for example, one skilled in the art may appreciate that the base unit can have a sensor interface (and/or an actuator/stimulator) that is part of the base unit 100 and connected to the communication circuit 105 and/or power circuit 130. As noted below, the depiction of the antenna 115 in FIG. 1 is representative, and other shapes (and types) of antennas can be used.

As noted above, the (implanted) base unit 100 can communicate with the device located external to the patient and other base units (that are similarly constructed) that are also implanted in the patient using a combination of RF and US signals. Additionally, as noted above, the base unit(s) can include one or more sensors, with each base unit including the same or different types of sensors, which can be implanted at various places in the patient (including the brain).

Figure 2:
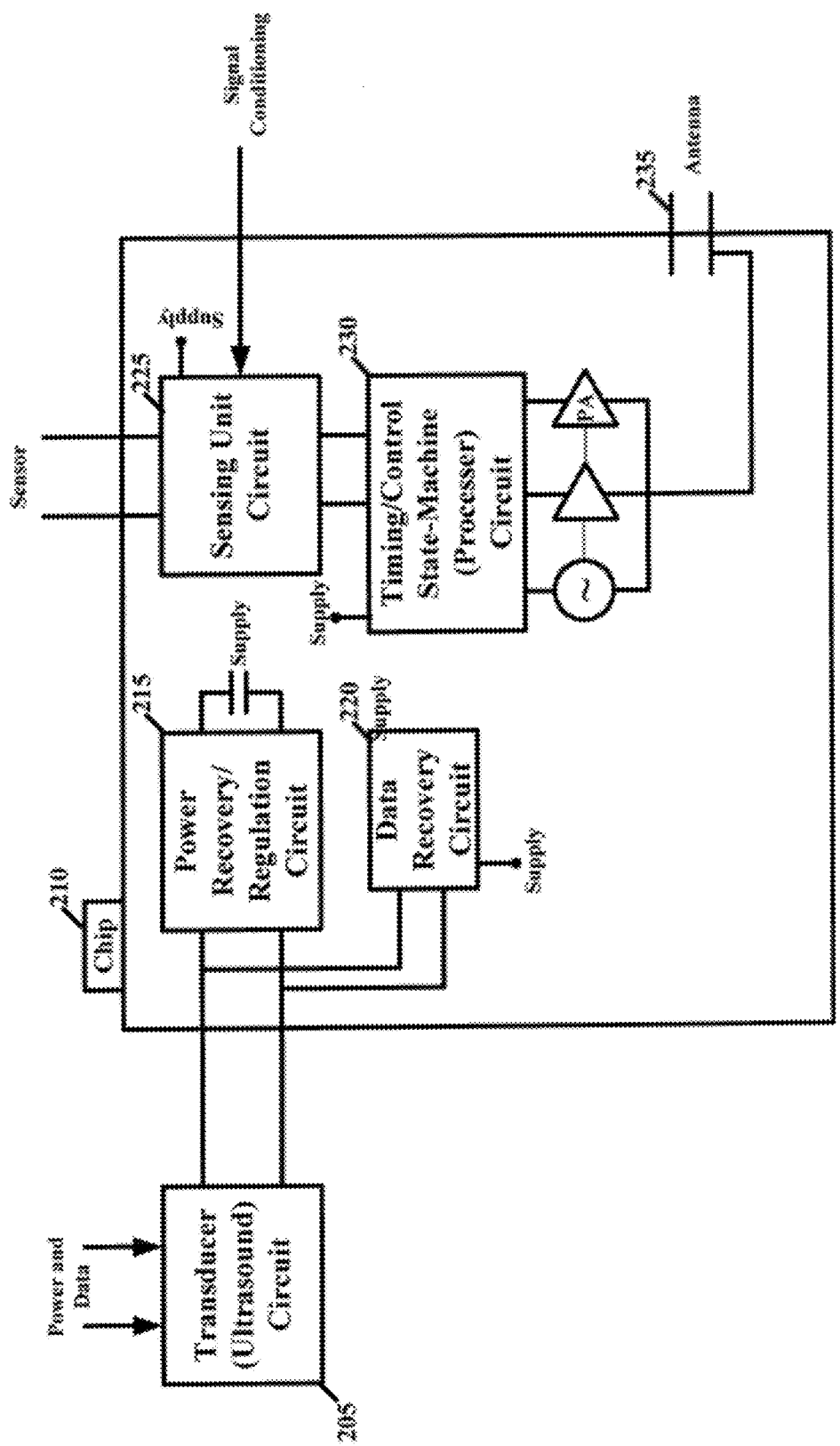
FIG. 2 shows another block diagram of an example base unit, according to various aspects of the current invention.

FIG. 2 shows another block diagram of an example base unit 200, consistent with various aspects of the present disclosure. The base unit 200 includes a transducer (ultrasound) circuit 205 and an integrated chip circuit 210 that includes a power recovery and regulation circuit 215, a data recovery circuit 220, sensing unit circuitry 225, timing/control processor circuitry 230, and circuitry for operating an RF antenna 235. The transducer (ultrasound) circuit 205 receives power and/or data signals provided in the form of US signal(s) from an external device, which will be passed to the power recovery and regulation circuit 215 as well as the data recovery circuit 220. The power recovery and regulation circuit 215 captures the power that is generated and received by the transducer (ultrasound) circuit 205, and also regulates the power that is provided to the remaining aspects of the integrated chip circuit 210. The data recovery circuit 220 receives the signals from the transducer circuit (ultrasound) 205, and passes the signals on if required. For instance, the data recovery circuit 220 can pass the data signals to the timing/control processor circuitry 230, which can activate the sensing unit circuitry 225. As discussed above, the sensing unit circuitry 225 controls and/or receives data from a sensor provided with the integrated chip circuit 210. Additionally, the integrated chip circuit 210 can communicate with external devices and/or other integrated chip blocks utilizing the circuitry shown for operating an RF antenna 235. The power recovery and regulation circuit 215 can also include an on-chip power supply (such as a battery) that can store the energy received by the transducer (ultrasound) circuit 205.

The timing/control processor circuitry 230 recovers the sensor output (data) from the sensing unit circuitry 225. Additionally, the timing/control processor circuitry 230 recovers timing data received from the downlinked signals from the data recovery circuit 220. The timing/control processor circuitry 230 also generates the modulated signals for RF transmission via the RF antenna 235. The timing/control processor circuitry 230 provides all timings, control, and duty cycles for the transmitted signals. The transducer (ultrasound) circuit 205 can include one or more transducers. In this manner, for example, the transducer (ultrasound) circuit 205 can have a dedicated transducer for downlink data and power, and a dedicated transmitter for uplink data (as described in further detail above).

FIGS. 3A-3C show example base units 300, consistent with various aspects of the present disclosure. Each of base units 300 includes a sensor interface 305, a silicon chip 310, and a transducer 315. Additionally, the base units 300 can also include a capacitor that can be on or off the silicon chip 310. The base unit shown in FIG. 3A includes a stack of the sensor interface 305, the silicon chip 310, and a transducer (the capacitor and an RF antenna are not shown). FIG. 3B shows a different example base unit 300 that also shows an RF antenna 320. FIG. 3C shows another different example base unit 300 base unit that includes the RF antenna 320 around the edge of a substrate 325.

Figure 4:
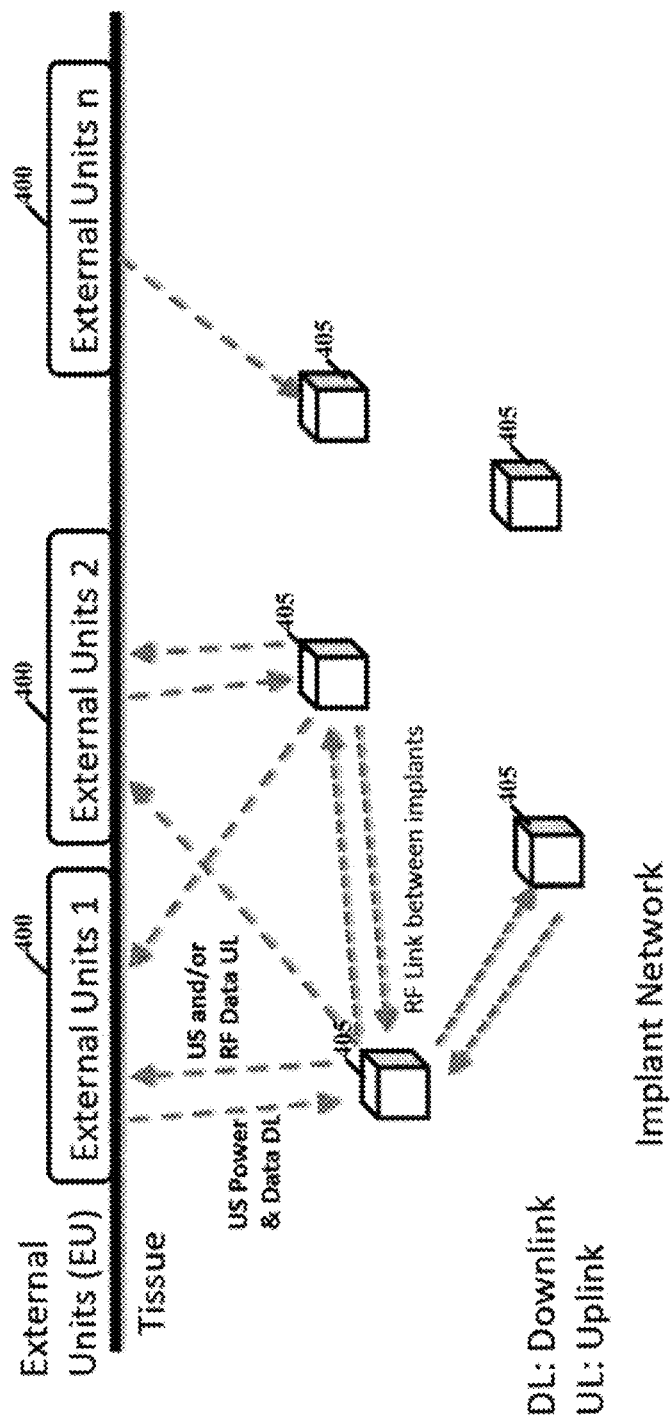
FIG. 4 shows an example network of devices 400 that are external to a patient (e.g., tissue) and base units 405, according to various aspects of the current invention.

FIG. 4 shows an example network of devices 400 that are external to a patient (e.g., tissue) and base units 405, consistent with various aspects of the present disclosure. As noted above, the base units 405, consistent with various aspects of the present disclosure, communicate with one or more devices 400 that are external to a patient. Additionally, the base units 405 can communicate amongst each other. In both instances, the communication is bidirectional (uplink and downlink). The downlink from the one or more devices 400 that are external to a patient and one or more of the base units 405 occurs using RF or US signals that include data.

The uplink from the one or more devices 400 that are external to a patient and one or more of the base units 405 occurs using US signals and/or RF signals, which includes data. The communication between the base units 405 occurs via an RF link that carries RF signals.

Each of the base units 405 includes a unique address or a time window to transmit the signals. For example, one or more devices 400 that are external to a patient can communicate to one or more of the base units 405 using an allocation of the signal(s) based on slot, data and/or position. Additionally, the signal modulation can be in multiple-pulse pulse position modulation (MPPM) format, and each of the base units 405 can send multiple pulses to calibrate errors in the timing of the communication protocol. After one or more devices 400 that are external to a patient address and provide data to one or more of the base units 405, the signal position to the base units 405 can also be modulated based on the physical position of the base units 405 in the patient. This can be used for ranging/tracking of the base units 405 (e.g., the movement of the patient can shift the original position of the base units 405).

As noted above, the base units 405 can synchronize with one or more devices 400 that are external to a patient using periodic beacons sent from one or more devices 400 that are external to a patient. There is no explicit timing circuitry that is required for the base units 405 based on this synchronization capability. To reduce errors in communication, the base units 405 can send multiple calibration pulses to communicate the actual clock cycle to one or more devices 400 that are external to a patient. This eliminates the need for very high-accuracy clocks on the base units 405 (which can minimize the power needed) and eliminate issues of drift.

To facilitate the downlink power transfer from one or more of the devices 400 external to the patient to one or more of the base units 405, the US energy can be focused (either using an electronic beamforming array or by a passive acoustic lens) at the sites where the base units 405 are implanted in the patient. Additionally, as described above, feedback can be provide over the RF (up)link from one or more of the base units 405 to one or more of the devices 400 external to the patient. For example, US power can be gradually increased with feedback from the RF link. Once the position of the one or more of the base units 405 is identified based on this feedback, using ranging/tracking and determining the time of flight of the signal, US signal focusing will take place (with high power density). US energy will only be directed to positions of the base units 405 (or a focal volume that is set by the array).

Figure 5C:
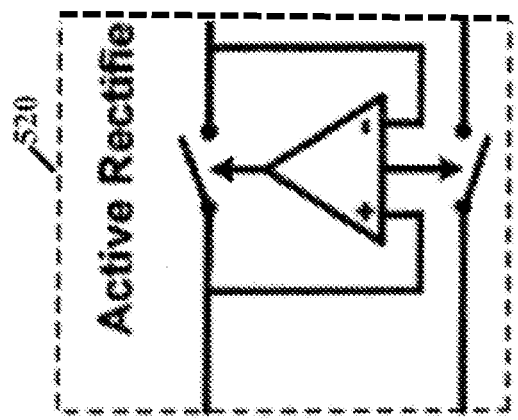
FIGS. 5A-5C shows example power harvesters, according to various aspects of the current invention.
Figure 5B:
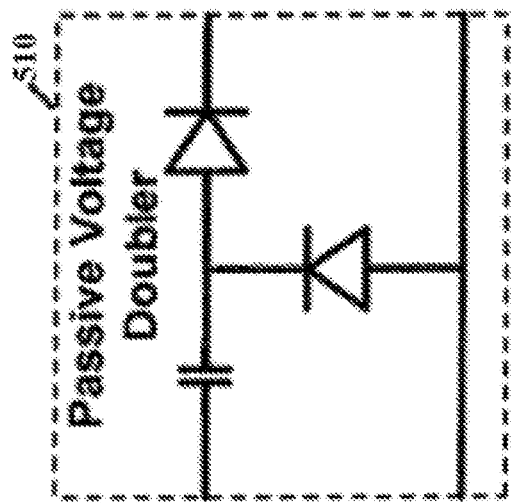
Figure 5A:
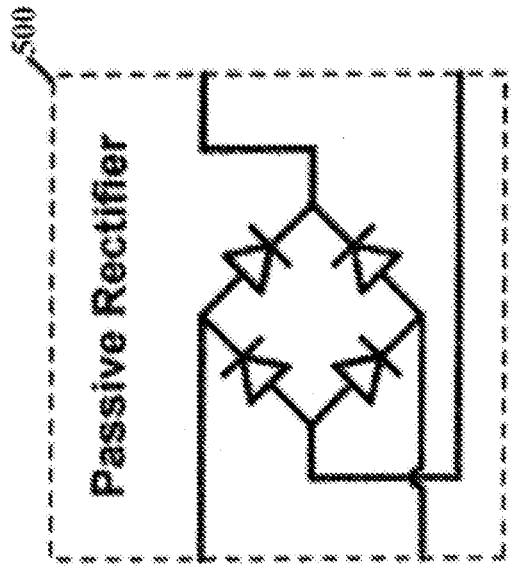

FIG. 5 shows example power harvesters, consistent with various aspects of the present disclosure. The example power harvesters shown are a passive rectifier 500, a passive voltage doubler 510, and an active rectifier 520. One or more of the example power harvesters can be included with a base unit, consistent with various aspects of the present disclosure.

Figure 6:
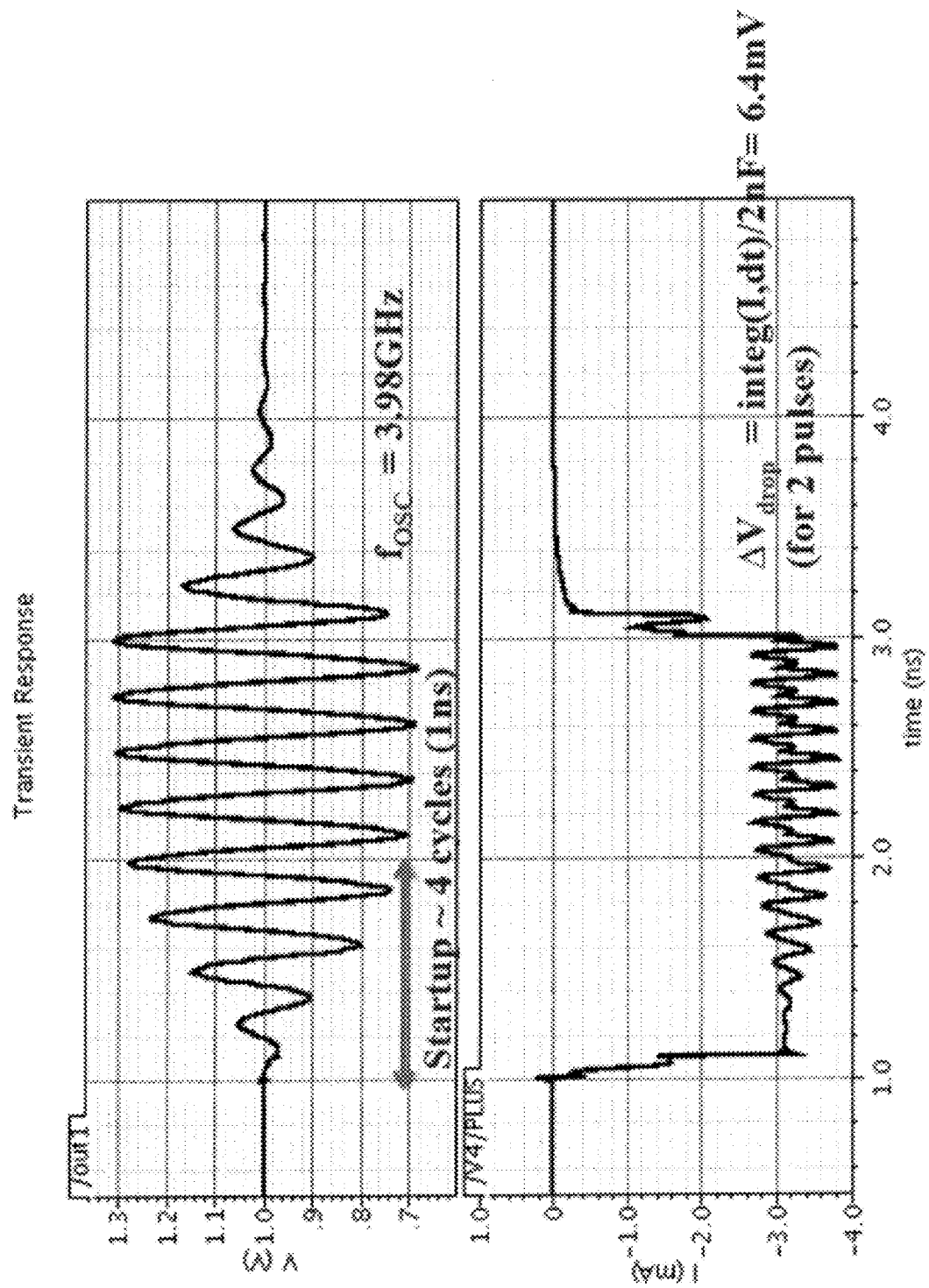
FIG. 6 shows an example transient response of a RF transmitter and a voltage drop, according to various aspects of the current invention.
Figure 7:
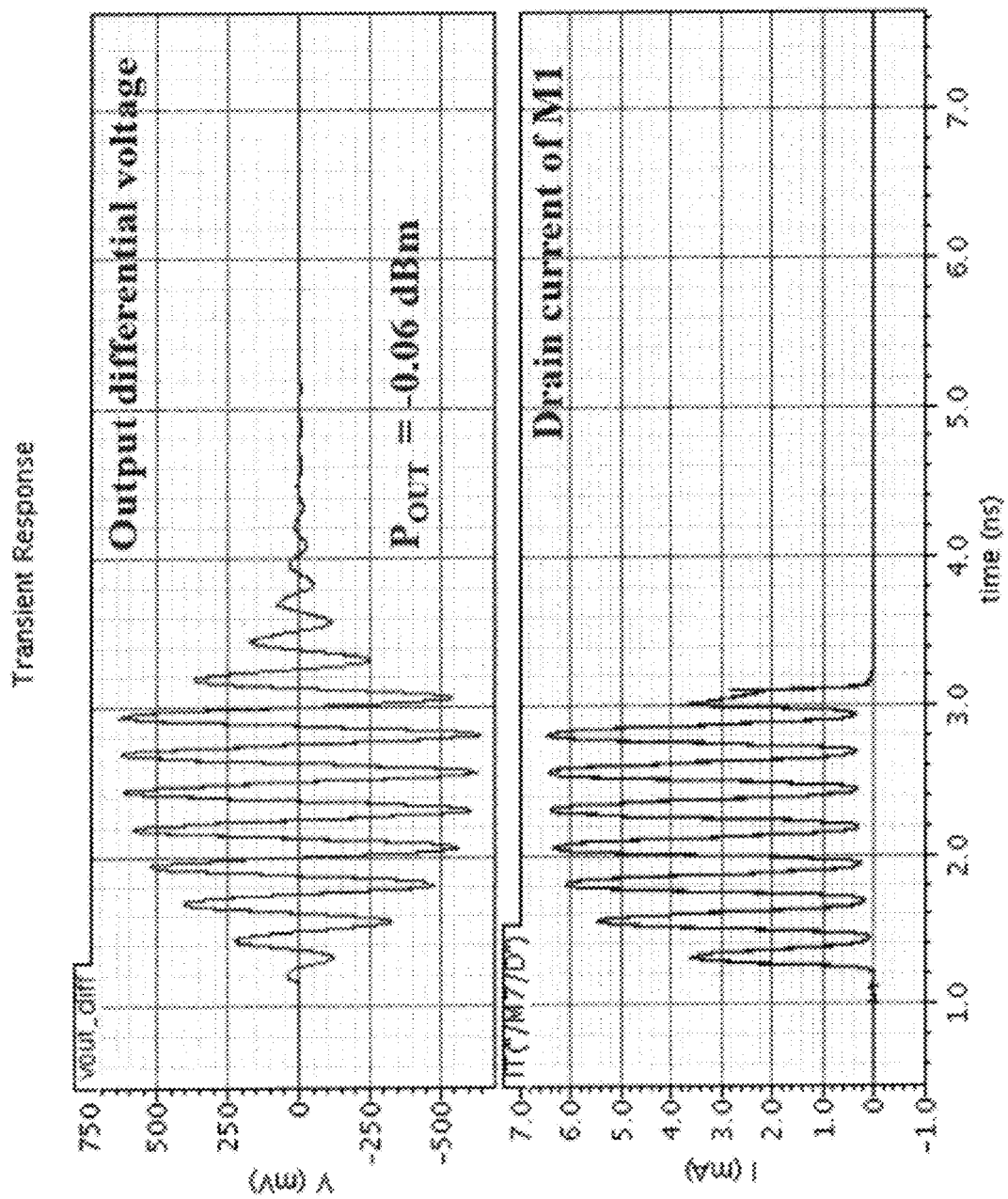
FIG. 7 shows an example output differential voltage of a base unit and drain current, according to various aspects of the current invention.

FIG. 6 shows an example transient response of an RF transmitter and a voltage drop, consistent with various aspects of the present disclosure. FIG. 7 shows an example output differential voltage of an implantable package and drain current, consistent with various aspects of the present disclosure.

As an example experimental budget link calculation, based on an order of magnitude per calculation, a base unit that does not include an external (additional) capacitor circuit is sized to include a 65 nm CMOS circuit. The total on-chip capacitor (storage) is approximately 1-5 nF, so it is reasonable to assume a total energy of approximately 1 nJ (for 2 nF capacitor charged to 1V). Typical duty-cycled RF pulses could consume approximately 1-100 mA current in active time and span from 0.1 to 100 (or even 1000) ns. Assuming a 10 mA current with a 2 ns pulse width, each pulse would draw approximately 20 pC of charge from the capacitor, which is 2% of the total stored charge. For charging using US, the power density of the signals is assumed to be 100 mW/cm$^2$. Thus, for a 1 mm$^2$ base unit, there is 1 mW of available power. Assuming 20% net efficiency, the charging power is 200 µW. So the time it takes for the capacitor circuit to recover the lost charge is approximately 100 ns, with a maximum duty cycle of 2%. Thus, if 5 pulses are transmitted (resulting in a 10% loss), the base unit will take 500 ns to recover its full power.

Various aspects of the present disclosure are also directed toward an apparatus or methods that include an implantable package that receives US acoustic waves from an external device, and converts those US acoustic waves into electrical energy. In certain more specific embodiments, the implantable package includes a piezoelectric or capacitive transducer to convert the US acoustic waves into electrical energy.

Aspects of the present disclosure are also directed toward an apparatus or methods that include an implantable package that communicates with an external device and/or other implantable packages or sensors using a combination of RF and US signals. The implantable package can communicate utilizing a pulse-based communication scheme that includes periodic (<100 nanosecond) bursts of energy at RF or microwave frequencies (0.1-10 GHz). Other forms of communication are also possible (e.g., Frequency-Shift Keying FSK).

Certain aspects of the present disclosure are also directed toward an apparatus or methods having an implantable package that utilizes a pulsed-based signaling timing to receive and convert US acoustic waves into electrical energy 5 from an external device. Additionally, the implantable package communicates with the external device and/or other implantable packages or sensors using a combination of RF and US signals. In certain more specific embodiments, the pulsed-based signaling timing includes utilizing at least one of pulse PPM, multi-PPM, and PWM.

Various aspects of the present disclosure are directed toward an apparatus or methods that utilize an implantable package to communicate with an external device or other implantable packages or sensors using an active pulse transmission. More specifically and in certain embodiments, such an implantable package includes an antenna or transducer, and a local oscillator that generates active pulse transmission signals. Further, the implantable package also includes a pulser to modulate the active pulse transmission signals, and a power amplifier that buffers the active pulse transmission signals and transmits the active pulse transmission signals to the antenna or the transducer.

Moreover, aspects of the present disclosure are directed toward an apparatus or methods having an implantable package. The implantable package can communicate with an external device or other implantable packages or sensors, and also receive signals from the external device. The received signals include periodic beacons to synchronize the implantable package with the external device and other implantable packages or sensors. Further, in certain embodiments, the periodic beacons are used to synchronize all sensors or implantable packages and to calibrate and correct for any mismatch, delay, skew, or jitter.

Various aspects of the present disclosure are also directed toward an apparatus or methods that utilize an implantable package. The implantable package can include an integrated circuit as well as a capacitor (provided on the integrated circuit or provided external from the integrated circuit) that provides power to the integrated circuit to periodically transfer an active pulse from the implantable package. Further, the implantable package can include an antenna (external from the integrated circuit) that communicates with RF signals and/or an acoustic transducer that communicates with US signals to an external device in response to the power-up of the integrated circuit. Additionally, the implantable device can also include an acoustic transducer and interface that provides a power-up to the integrated circuit in response to an US signal provided from an external device. Implantable packages, consistent with various aspects of the present disclosure, can also include different types of sensors such as a chemical sensor, a molecular sensor, an impedance sensor, a fluorescence sensor, an optical sensor, a temperature sensor, and/or a vibrational sensor. Further, implantable packages can also include an LED or other light source, which is powered-up and modulated in response to signals received by the implantable package.

Various aspects of the present disclosure utilize directed US energy for remote power delivery to a sensor or implantable device or package. The US energy can act as the sole power-up scheme or to supplement the power from a RF power delivery system. In certain embodiments, the implantable device or package can include an antenna or a near-field element (loop or capacitor) for RF communication. The antenna or near-field element can be provided on the same chip or external to the chip on the common board or substrate. In such an embodiment, downlink data can be modulated on top of a carrier in the form of amplitude-shift keying (ASK), on-off keying (OOK), phase shift keying (PSK), or other types of suitable modulation schemes. Additionally, RF frequencies can be used for uplink communication from an implantable device or sensor to an external transceiver. This communication technique can also be used to compliment an US uplink. In this manner, a hybrid communication scheme can be formed that intelligently uses a combination of RF and US for power-up and communication. The active uplink pulse can be an RF pulse (typically with center frequency in the range of 0.1 GHz-10 GHz) or a US pulse actuated by a piezoelectric device or similar US transducers. The US pulse has a center frequency typically in the 100 KHz-100 MHz range and can be several cycles long (up to 1000's of cycles long).

Further, active pulse transmission (or backscatter) can be used for communication. In this manner, the charge or energy from the power delivery system (US or US-assisted) is stored on an on-chip or off-chip capacitor (e.g., typically 1 nF-100 µF depending on type of capacitor and implant size). This energy is used to periodically transmit an active pulse from the device.

Various implementations of the devices and/or sensors of the present disclosure can be implemented or packaged in a single millimeter-size "cube" that would include a chip, transducer(s), an energy storage unit, and one or more antennas. Uplink communication can use 14 GHz frequency. In the wireless uplink channel, the external receiver can have a low noise floor in order to allow for a large dynamic range in the link. Losses in the order of 50-80 dB can be tolerated since the goal is not power delivery but communication. Thus, using RF for data uplink may not face the same challenges as for power delivery.

In certain embodiments, the RF link provides a high bandwidth in communication in the case of many implantable packages. This aids with both data rate (aggregate data rate from all implantable packages) as well as multiplexing/multi-access (fewer number of collisions in the shared channel). Further, the communications can be pulsed on the range of nanoseconds that provides heavy duty cycling, and therefore can provide high energy efficiency in the implantable package. This can allow for use of a single piezo element. Further, utilizing active pulse transmission can extend the operation range of the implantable package or sensor. The active pulse can have a peak power in the range of −50 dBm to 20 dBm (for implants this number is typically between −30 dBm and 0dBm). The sensor can be integrated with other sensing and actuation elements. For example a fluorescence imager can be integrated in the package. Additionally, an array of LEDs or other light sources can be used for deep tissue implants in optogenetics. Glucose monitoring and insulin delivery can also be provided.

Various aspects of the present disclosure are directed toward a device or sensor that utilizes a piezoelectric or capacitive micro-machined transducer to convert acoustic waves into electrical energy. The electrical energy recovered by the transducer is stored on a capacitor and is used to operate the device. This operation includes communication, sensing, actuation, and stimulation by the sensor (e.g., using an LED or other light source to excite with light). The transmission is "wireless" and non-contact. The downlink communication (from external device to sensor) also takes place with this US wave. Depending on the application and to achieve higher data rates the downlink stream could also be using RF with a dedicated receiver chain that is powered up using the US signal through the power circuit. Different modulation schemes can be used to transmit this data (e.g., OOK on top of the incident US wave). Utilizing an US wave for power delivery, in certain embodiments, can assist in bringing the physical dimensions of the sensor (~1 mm^3 or even smaller) closer to the wavelength (acoustic wavelength is orders of magnitude shorter than electromagnetic wave due to lower wave velocity). This can allow the sensor to capture more of the incident energy with limited aperture. Additionally, acoustic propagation of US waves in human tissue can experience significantly lower loss compared to electromagnetic wave propagation (e.g., 1 dB/cm compared to >3-10 dB/cm for RF/electromagnetic wave in the low GHz frequency range). Moreover, US waves can be provided with a higher allowable power density than RF waves.

In certain embodiments, an US signal used for wireless power delivery to the base unit is provided by one or more ultrasonic transducers in an external device. An array of US transducers can be used to perform focusing by electronic beamforming. In the case of medical implants these external transducers will be external to the body and reside on the surface of the skin. On applications as in brain implants (e.g., closed-loop deep-brain stimulation (DBS)), these ultrasonic transducers can be intracranial implants and reside on the cortex itself. That array and the electronics will then be powered up by another transcranial wireless link (either RF or US).

In other embodiments, base units, consistent with various aspects of the present disclosure, use an ultrasonic transducer to recover energy from the ultrasonic signal that is provided by the external units, and then use that energy to power up independent RF transmitter and/or receiver units that communicate with the external units and/or other base units in the environment. The communication may be duty-cycled and pulsed, and a large energy storage unit could be used to provide burst-mode energy for this type of communication.

More specifically, in certain embodiments, this transducer is used to harvest the energy carried by the US signals as well as to recover the downlink (DL) data that is sent to the base unit. This data can be modulated on the amplitude of the US signal. In another example and in case of using US for uplink, the base unit can transmit active US pulses using the acoustic transducer, or alternatively use backscatter modulation. If the same transducer is used for both downlink and uplink then a transmit/receiver switch or some form of time-multiplexing the two functions will be utilized.

For further discussion of implantable sensors, as relating to the embodiments and specific applications discussed herein, reference may be made to the underlying U.S. Provisional Patent Application, Ser. No. 61/822,763 filed on May 13, 2013 (including the Appendices therein) to which priority is claimed and which are fully incorporated herein by reference generally and for the reasons noted above. The aspects discussed therein may be implemented in connection with one or more of embodiments and implementations of the present disclosure (as well as with those shown in the figures). Moreover, for general information and for specifics regarding applications and implementations to which one or more embodiments of the present disclosure may be directed to and/or applicable, reference may be made to the references cited in the aforesaid provisional application and Appendices, which are fully incorporated herein by reference generally and for the reasons noted above. In view of the description herein, those skilled in the art will recognize that many changes may be made thereto without departing from the spirit and scope of the present disclosure.

Various modules and/or other circuit-based building blocks may be implemented to carry out one or more of the operations and activities described herein and/or shown in the figures. In such contexts, a "module" is a circuit that carries out one or more of these or related operations/activities. For example, in certain of the above-discussed embodiments, one or more modules are discrete logic circuits or programmable logic circuits configured and arranged for implementing these operations/activities, as in the circuit modules shown in the figures (e.g., the power recovery/regulation circuit shown in FIG. 2). Additionally, one skilled in the art may appreciate that antennas shown in the figures (such as FIG. 1) are representative and can be formed of different shapes and/or sizes. In certain embodiments, the programmable circuit is one or more computer circuits programmed to execute a set (or sets) of instructions (and/or configuration data). The instructions (and/or configuration data) can be in the form of firmware or software stored in and accessible from a memory (circuit). As an example, first and second modules include a combination of a CPU hardware-based circuit and a set of instructions in the form of firmware, where the first module includes a first CPU hardware circuit with one set of instructions and the second module includes a second CPU hardware circuit with another set of instructions.

Certain embodiments are directed to a computer program product (e.g., nonvolatile memory device), which includes a machine or computer-readable medium having stored thereon instructions, which may be executed by a computer (or other electronic device) to perform these operations/activities.

A first proof-of-concept mm-sized implantable device using ultrasonic power transfer and a hybrid bi-directional data communication link is disclosed. Ultrasonic power transfer enables miniaturization of the implant and operation deep inside the body, while still achieving safe and high power levels (100 μW-a few mWs) required for most implant applications. The current implant embodiment measures 4 mm×7.8 mm and comprises of a piezoelectric receiver, an IC designed in 65 nm CMOS process and an off-chip antenna. The IC can support a maximum DC load of 100 µW for an incident acoustic intensity that is ~5% of the FDA diagnostic limit. This demonstrates the feasibility of providing further higher available DC power, potentially opening up new implant applications. The hybrid bi-directional data link embodiment includes ultrasonic downlink and RF uplink. Falling edge of the ultrasound input is detected as downlink data. The implant transmits an ultra-wideband (UWB) pulse sequence as uplink data, demonstrating capability of implementing an energy-efficient M-ary PPM transmitter in the future.

Conventional wireless powering techniques such as inductive coupling and RF power transfer are inefficient for large range-to-implant-size ratio. Also, inductive powering is more sensitive to mutual orientation of coils as compared to far-field techniques. The inefficiency of RF power transfer in body is due to mismatch between the wavelength (~cm) and aperture of mm and sub-mm sized antennas, and the absorption of RF waves in tissue. The available power from such electrically small antennas is low due to a low radiation efficiency, small radiation resistance, large antenna quality factor (Q), and losses in typical matching networks from limited Qs of on-chip inductors and capacitors. Another major drawback of the large RF wavelength is that energy cannot be focused to a mm or sub-mm spot size, resulting in excessive heating, safety concerns, and low overall link efficiency. Other techniques such as ambient energy scavenging offer inadequate power densities for applications such as DBS.

Figure 8:
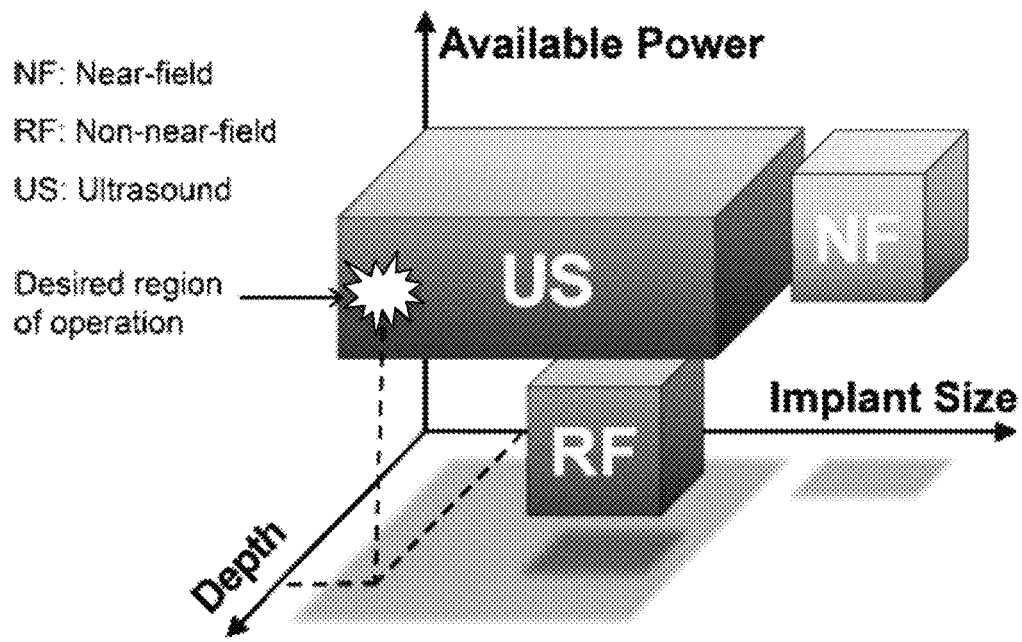
FIG. 8 shows a conceptual diagram showing the regimes of applicability of different wireless powering techniques and our desired region of operation.

The current invention uses ultrasound for power transfer since it has significantly smaller wavelength, comparable to miniature implant dimensions, due to orders of magnitude slower sound wave velocity. Smaller wavelength enables efficient focusing of energy at the implant as well as significantly improved coupling and transduction efficiency. The feasibility of beamforming ultrasonic energy to mm-sized focal spots at large depths in body, in a controlled and programmable way, and without exceeding safety limits in surrounding tissue, has already been demonstrated. Moreover, it is feasible to design miniature ultrasonic receivers with impedance profiles that allow for more efficient power transfer as compared to electrically small antennas, as discussed later in this paper. In addition, the FDA allows an intensity of 7.2 mW/mm$^2$ for diagnostic ultrasound applications, which is about two orders of magnitude higher than the safe RF exposure limit in body (10-100 µW/mm$^2$ [21, 22]). FIG. 8 shows a conceptual diagram of the regimes of applicability of different wireless powering techniques, with ultrasound being favorable for transferring high power levels to miniature, deeply-implanted medical devices.

Figure 9:
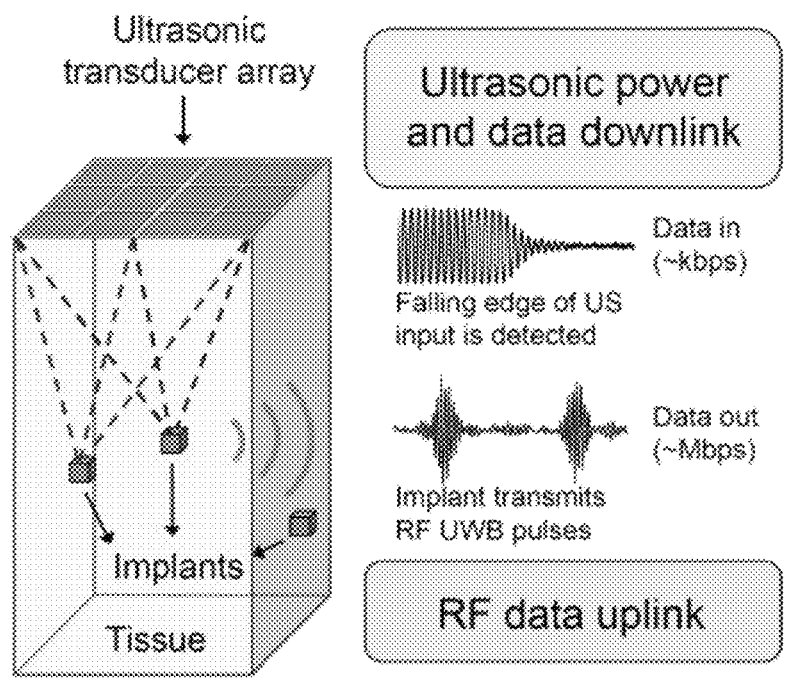
FIG. 9 shows a conceptual end application diagram showing external ultrasonic transducer array, a network of implants in body and the bi-directional data communication protocol in our current demonstration, according to embodiments of the current invention.

In addition to ultrasonic power transfer, the current invention provides a first demonstration of a hybrid bi-directional data communication link for implants. The end application diagram is shown in FIG. 9, where a network of implants are powered by an external ultrasonic transducer array. The current invention uses ultrasound for downlink and ultra-wideband (UWB) RF for uplink data transfer. While the ultrasonic downlink can be useful for transmitting low data rate (~kbps) control, command or clock signals to the implant, an energy-efficient RF uplink can be designed that enables high data-rates (~Mbps) for recovering in-vivo imaging data and high-resolution, multi-site neural recordings. In lower data-rate applications, a purely ultrasonic data link could be implemented. While the current implant fully demonstrates ultrasonic power recovery, and the capability of bi-directional data transfer, future designs could incorporate bio-sensors, electrodes for recording and/or stimulation, as well as clock recovery and data modulation circuits for implementing a more practical data link.

Figure 10:
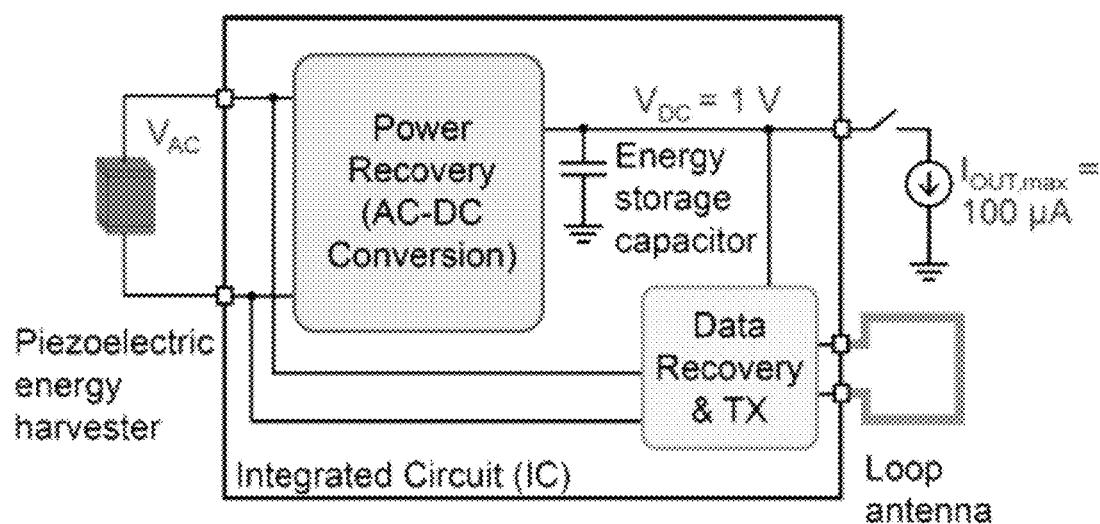
FIG. 10 shows a system block diagram of the implant, according to embodiments of the current invention.

The implant system according to one embodiment of the invention includes a piezoelectric energy receiver, an integrated circuit (IC) chip and a loop antenna as shown in FIG. 10. Ultrasonic energy is harvested in the form of AC power by the piezoelectric receiver, which is then converted to DC energy, via power recovery circuits on the IC, and stored on an on-chip capacitor ($C_{STOR}$). The stored energy could be used for powering different functions such as: stimulation, bio-sensing and neural recording. The IC also includes a data recovery and transmitter circuit for downlink and uplink communication with the implant.

The piezoelectric receiver is designed to simultaneously achieve small dimensions, high available power, and favorable impedance for efficient energy harvesting. The impedance and available power for a piezoelectric receiver are dependent on several design variables such as: material, dimensions and acoustic loadings from the package. One embodiment for the piezoelectric device involves using the 1D Krimholtz, Leedom and Matthaei (KLM) model for first-order insight and performing 3D finite element simulations using the COMSOL Multiphysics tool. For this demonstration, Lead Zirconate Titanate (PZT) is chosen as the piezoelectric material due to its high electro-mechanical coupling factor, though a more rigorous study could be performed in the future to optimize for power conversion efficiency, small dimensions and bio-compatibility. A piezoelectric device has a fundamental open-circuit and a short-circuit resonance frequency at which the device impedance can be purely real. From the KLM model, these frequencies are mainly controlled by the thickness of the device, which, to first order, is equal to its half-wavelength at the open-circuit resonance frequency for low-impedance acoustic loadings. Operating frequency of 1 MHz is chosen based on the trade-off between the thickness of the device and losses in tissue. In order to achieve short-circuit resonance for PZT at 1 MHz, the device thickness was chosen to be 1.4 mm. Further, the lateral dimension was chosen to be 1 mm in order to achieve minimal coupling to parasitic vibration modes of the device. This sub-wavelength dimension also helps in achieving a large acceptance angle, thereby reducing the impact of implant rotations on power recovery. Measurements of our piezoelectric devices are performed in a tank filled with mineral oil since it has similar acoustic impedance to soft tissue. FIGS. 11A-11B show the measured and simulated impedance profiles (using COMSOL) of two different sized piezoelectric receivers in oil. The measurements and simulations show good agreement—demonstrating our simulations' utility in design. The measurement shows slightly lower Q because we have not modeled all of the packaging in the simulations. The simulated displacement profile of the 1.4 mm$^3$ device is also pictured. The equivalent circuit model of the piezoelectric device at its short-circuit resonance frequency is shown in FIG. 11C. The short-circuit impedance can be varied between 2-6 kΩ through design of the package loadings. The 1.4 mm$^3$ and 0.5 mm$^3$ piezoelectric devices also achieve a high measured acoustic-to-electrical conversion efficiency (>50%) as shown in Table I. From the data, both devices achieve an electrical available power >100 µW at just 0.72 mW/mm$^2$ acoustic intensity (10% of the FDA diagnostic limit), allowing us to reach the mW range by further increasing the acoustic intensity.

TABLE I

MEASURED ACOUSTIC-TO-ELECTRICAL CONVERSION EFFICIENCY (η) CALIBRATED USING A HYDROPHONE, AND CALCULATED AVAILABLE ELECTRICAL POWER ($P_{AV}$) FOR AN INCIDENT ACOUSTIC INTENSITY ($I_O$) OF 0.72 mW/mm$^2$ (10% OF THE FDA LIMIT).

| Piezoelectric receiver dimensions | Measured η | Calculated $P_{AV}$ for $I_O$ = 0.72 mW/mm$^2$ ($P_{AV}$ = η × $I_O$ × Area) |
|---|---|---|
| 1 mm × 1 mm × 1.4 mm (1.4 mm$^3$) | >50% | 360 µW |
| 0.7 mm × 0.7 mm × 1 mm (0.5 mm$^3$) | >50% | 176 µW |

Since downlink data rates required in typical implant applications are kbps, an ultrasonic downlink operating at a carrier frequency of ~MHz is feasible. The proof-of-concept downlink protocol, as shown in FIG. 9, uses the falling edge of the ultrasound signal as an input "trigger" for the implant. In this protocol, the maximum achievable downlink trigger rate is determined by the minimum required ON and OFF times of the ultrasound input. The minimum OFF time is limited by the rate of discharge of the ultrasound envelope as well as the speed of the envelope detector circuit. The discharge rate of the ultrasound envelope largely depends on the impedance profile of the piezoelectric receiver, and other complex factors such as the dispersion of its acoustic-to-electrical conversion efficiency and the non-linear input impedance of the IC. The minimum ON time is determined by the time required to fully recharge $C_{STOR}$. Based on typical values of ON and OFF times from our design and measurements, downlink trigger rates >10 kbps can be achieved. For applications demanding a larger downlink data rate, a different protocol such as amplitude-shift keying with a small modulation depth can be implemented in the future.

In spite of the drawbacks of RF for wireless power transfer, it is still feasible to implement an RF data uplink, because signal level required at the external data receiver can be as low as −70 to −80 dBm, as opposed to −20 to 0 dBm for power. This is possible because the link is highly asymmetric, allowing the external receiver to be large, consume more power, and thus, have higher sensitivity as compared to the implant. Assuming a bandwidth of 1 GHz, a signal-to-noise ratio (SNR) of 10 dB and a noise figure of 3 dB, the sensitivity of the external receiver can be calculated to be −71 dBm. The uplink protocol includes transmitting two UWB pulses from the implant, upon the recovery of the input trigger, as illustrated in FIG. 9. This demonstrates sufficient energy at the implant showing capability of implementing m-PPM modulation in the future, where the first pulse can serve as a calibration or synchronization pulse, and the second pulse can be positioned to lie in one of 'm' slots. This protocol enables heavy duty-cycling of the transmitter, resulting in extremely low average power consumption and an improved energy efficiency, as demonstrated in upcoming sections.

In this embodiment, an RF frequency of 4 GHz was chosen, based on considerations of the implant antenna size and depth in tissue, as discussed further in section V. The nominal pulse width is chosen to be 2 ns and the nominal inter-pulse delay is fixed at 10 ns. A further smaller pulse width could enable lower energy consumption per pulse and higher uplink data rates, but would require a wideband antenna and a higher RF carrier frequency, which has larger losses in tissue. Accounting for losses in the link (discussed in section V), the peak power delivered to the implant antenna is targeted to be between −10 and 0 dBm in order to meet the −71 dBm sensitivity of the external receiver. Thus, the current system demonstrates the capability of uplink and downlink communication. However, as discussed below, additional blocks for clock recovery, data processing and modulation should be implemented for achieving a complete wireless data link.

A power recovery and management circuit is required, along with a regulated output DC rail, for reliably powering data transmitters, sensors or stimulation circuits required in most implant applications. In this embodiment, a regulated DC output voltage of 1 V and a maximum DC output current ($I_{out}$) of 100 µA were targeted, i.e. a maximum DC load power ($P_{out,dc}$) of 100 µW. The target peak AC input voltage ($V_{in}$) range for the power recovery circuit is 0.6-1.1 V, based on the threshold voltage of typical rectifiers and the breakdown voltage limit of transistors.

The fundamental component of the input resistance ($R_{in}$) of a typical AC-DC power recovery circuit is approximately given by:

$$R_{in} = \frac{V_{in}^2}{2P_{in,avg}} = \frac{V_{in}^2 \times \eta_{AC-DC}}{2P_{out,dc}} \quad (1)$$

where, is the average input power of the IC and $\eta_{AC-DC}$ is the efficiency of the AC-DC converter. For $V_{in}$ between 0.6-1.1 V, $P_{out,dc}$ between 10-100 µW and $\eta_{AC-DC}$ between 30-70%, $R_{in}$ is between 0.5-42.4 kΩ The input impedance also comprises of a shunt capacitance, which includes the parasitic capacitance of MOS transistors or diodes connected at the AC inputs. However, it can be ignored at the frequency of interest (1 MHz) and for the typical values of $R_{in}$ in this design. Thus, the resistances of the AC-DC converter and the piezoelectric receiver can be designed to lie in a similar range (~kΩ), alleviating the need for a dedicated input matching network, while still achieving good power transfer efficiencies.

A typical Dickson multiplier used for power recovery in this design would require very large values of coupling capacitors due to low input frequency (1 MHz) and large $I_{out}$ (100 µA) requirement. The output DC voltage ($V_{dc}$) of a single-stage Dickson multiplier is approximately given by $V_{dc}=V_{in}-I_{out}/(C_C f)$, where, $C_C$ is the coupling capacitance and f is the input frequency. For simplicity, the above equation assumes zero voltage drop across the diodes in the multiplier circuit and ignores the effect of diode parasitic capacitance. Based on the above equation, if $V_{in}=1$ V, $I_{out}=100$ µA and f=1 MHz, then for achieving $V_{dc}=0.9$ V, for instance, the required value of $C_C$ is 1 nF. Moreover, the load capacitance at $V_{dc}$ node is typically chosen to be an order of magnitude larger than $C_C$, resulting in a very large on-chip area.

Figure 12:
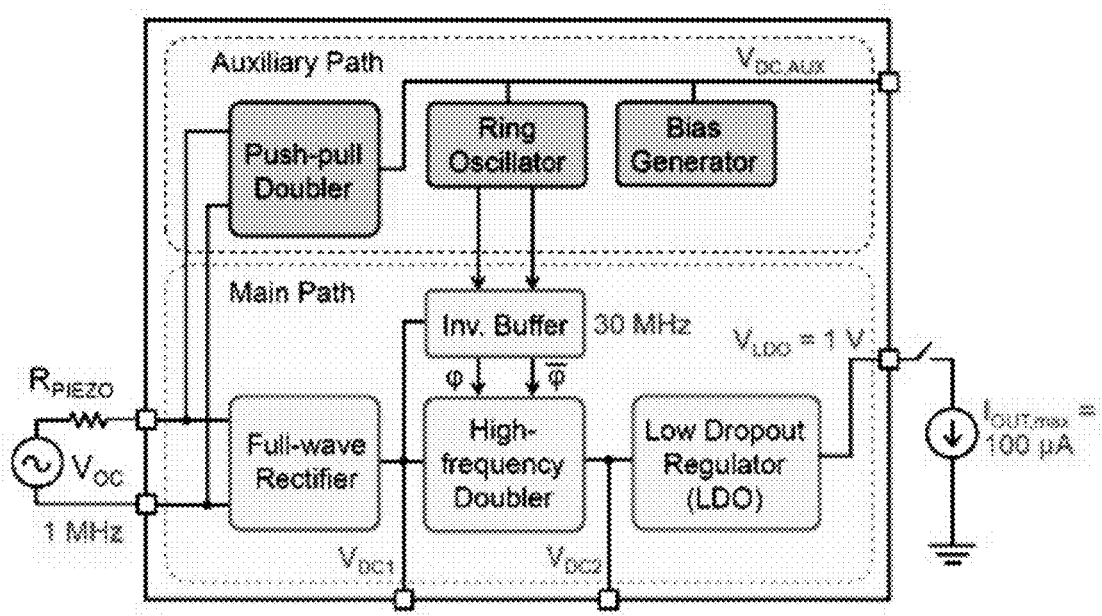
FIG. 12 shows a hybrid two-path architecture of the power recovery circuit, according to embodiments of the current invention.

Thus, in order to reduce the size of coupling capacitors, we decouple the constraints of low f and large $I_{out}$ by designing a power recovery circuit with a hybrid two-path architecture as shown in FIG. 12. In this architecture, the main power path is designed to support the large $I_{out}$ (100 µA) and operate at a high switching frequency (30 MHz) for reducing the size of coupling capacitors. In this path, the AC input voltage is first rectified to a DC voltage ($V_{DC1}$) using a full-wave active rectifier. A high-frequency voltage doubler is then used to double this voltage to $V_{DC2}$. Subsequently, a low dropout regulator (LDO), powered from $V_{DC2}$, generates a constant DC rail ($V_{LDO}$). In parallel to the main path, we implement an auxiliary power path consisting of a push-pull voltage doubler that generates an auxiliary DC rail ($V_{DC,AUX}$) for powering low power consuming blocks, such as a constant-gm bias circuit and a ring oscillator that drives the high-frequency doubler. Due to low output power of this path, the size of coupling capacitors required in the push-pull doubler need not be large. This architecture, thus, enables the generation of reference and clock signals at low available powers during startup, while still supporting a large load power, without compromising efficiency or using impractical values of coupling capacitors.

For high available input power, power conversion efficiency (PCE) for this architecture increases with $P_{out,dc}$, up to the maximum sustainable $P_{out,dc}$. For very low $P_{out,dc}$, PCE is limited by the quiescent power dissipation in the LDO and other circuit blocks. For low available input power, $V_{in}$ is low, resulting in lower rectification efficiency. Techniques for improving the efficiency of the rectifier at low $V_{in}$, and implementation of an efficient and reconfigurable charge-pump] for minimizing the voltage drop across the LDO pass transistor, can further improve the PCE across a wide range of input powers and load currents.

Figure 13B:
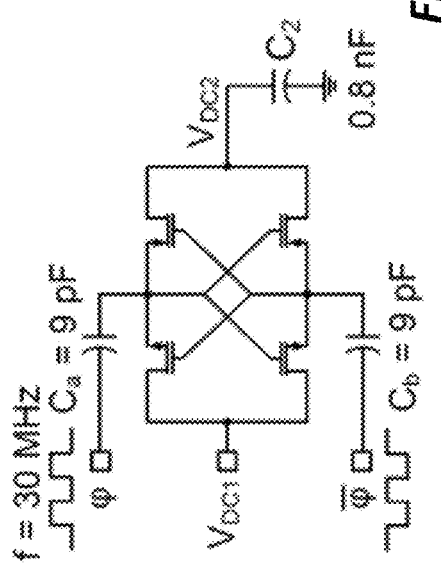
FIGS. 13A-13C show a power recovery circuits in the main power path: (a) active full-wave rectifier and the comparator used in the active PMOS diode; (b) high-frequency voltage doubler; (c) LDO circuit and generation of the POR signal, according to embodiments of the current invention.
Figure 13C:
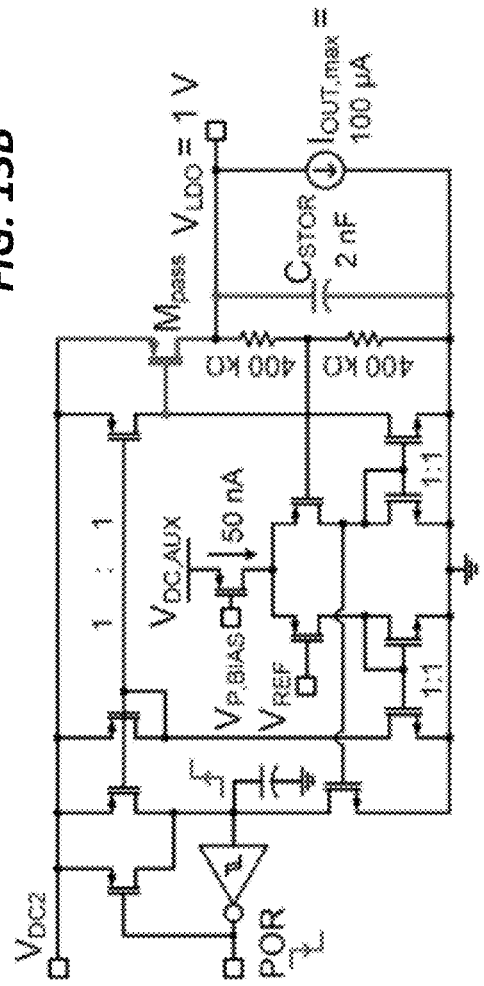
Figure 13A:
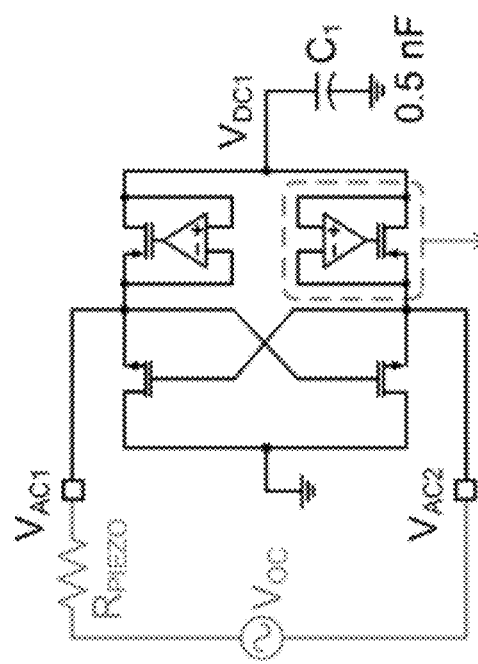

FIG. 13A shows a schematic of the full-wave active rectifier consisting of a gate cross-coupled NMOS pair and active PMOS diodes operating as switches. This topology enables low dropout voltage across the transistors, resulting in a high PCE. The active PMOS diode uses a high-speed comparator with a common-gate input stage. Current sources of the comparator are biased from the constant-gm bias circuit powered from the $V_{DC,AUX}$ rail. Reliable startup of the active rectifier is, thus, guaranteed since $V_{DC,AUX}$ rail is generated using a passive voltage doubler. Post-layout simulation of this rectifier results in a $V_{DC1}$ of 0.72 V for peak $V_{in}$ of 0.8 V and a load power of 100 µW, confirming a voltage conversion ratio of 0.9 and a PCE of 89.4%. In this simulation, the dropout voltage across the NMOS transistors is 5.6 mV and that across the active PMOS diodes is 72 mV.

The high-frequency switched-capacitor voltage doubler, shown in FIG. 13B, is implemented using cross-coupled MOS transistors with two coupling capacitors ($C_a$ and $C_b$) driven by anti-phase clock signals φ and $\overline{φ}$. The values of these coupling capacitors (9 pF) and the switching frequency (30 MHz) are chosen based on the trade-off between switching losses, losses due to finite output resistance of the converter and charge redistribution losses. For $V_{DC1}$ of 1.0 V and a load power of 100 µW, post-layout simulations of this doubler yield a voltage conversion ratio of 1.78 and a PCE of 88%. The 30 MHz clock signal is generated using a 5-stage current-starved ring oscillator powered from $V_{DC,AUX}$. The output of the ring oscillator is further level-shifted to $V_{DC1}$ supply and fed at φ and $\overline{φ}$ through an inverter buffer.

The value of on-chip load capacitance of the rectifier ($C_1$) is chosen to be 0.5 nF, that of the doubler ($C_2$) is 0.8 nF and the storage at the output of the LDO ($C_{STOR}$) is 2 nF, based on the trade-off between startup time and the discharge rate of these rails during OFF time of the ultrasound input, as well as for minimizing voltage ripple. In layout, these capacitors are implemented as a combination of MOS and metal-oxide-metal (MOM) capacitors, achieving a capacitance density of 3.8 nF/mm². On-chip capacitors are used in this embodiment, since off-chip capacitors pose more integration challenges, in addition to consuming a large implant volume.

The schematic of the LDO is shown in FIG. 13C along with the scheme for generating a power-on-reset (POR) signal. The LDO, using a PMOS pass transistor and a current-mirror OTA as error amplifier, is designed for a maximum load of 100 µA and consumes a nominal quiescent current of 3.2 µA in simulation. The startup time of the LDO from post-layout simulations is 100 µs, which is also confirmed from measurements, as discussed in section VII. The LDO startup time is important because it would influence the throughput of a system consisting of a network of implants accessed by the external unit through time-domain multiple access (TDMA).

Figures 14A, 14B:
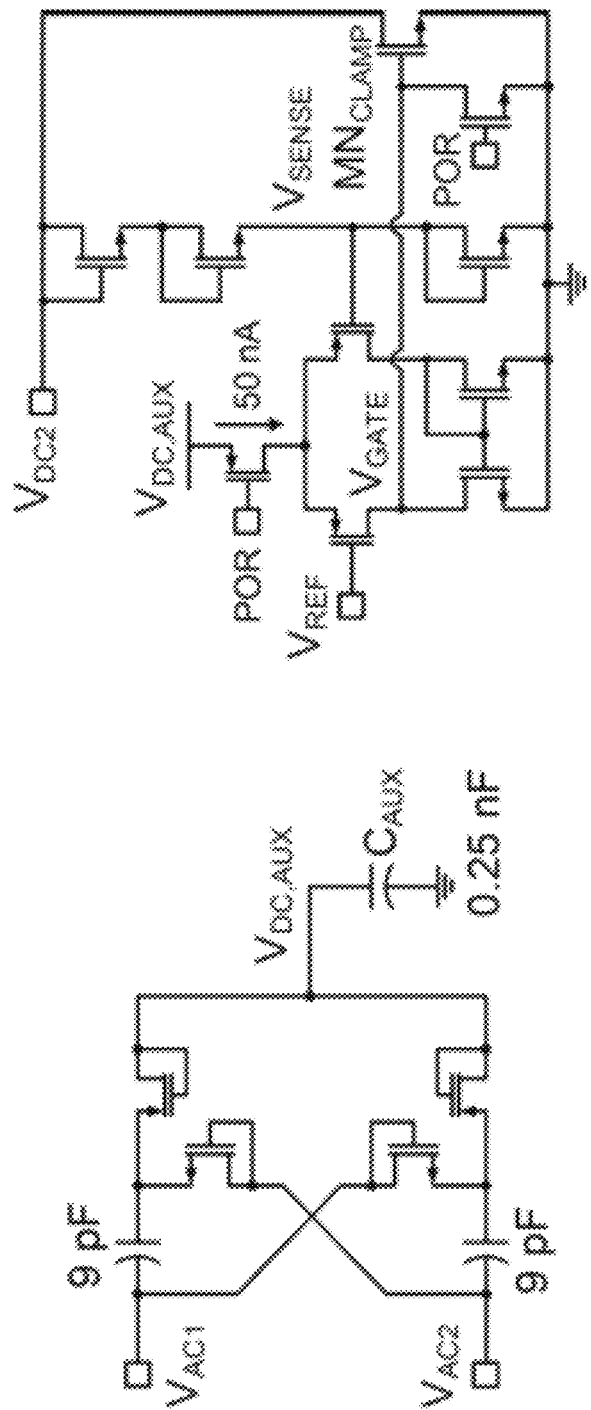
FIGS. 14A-14B show (a) Push-pull voltage doubler circuit used in the auxiliary power path, (b) Over-voltage protection circuit for $V_{DC2}$ rail, according to embodiments of the current invention.

In the auxiliary power path, the passive push-pull voltage doubler, shown in FIG. 14A, is implemented using diode-connected transistors. Although the diode-connected transistors result in a forward voltage drop, the PCE of this block does not impact the overall PCE due to a small load current for this stage. In order to prevent breakdown due to over-voltage at the inputs, diode-based and active voltage limiting clamps are added between the two AC inputs of the IC and at the DC rails: $V_{DC,AUX}$, $V_{DC1}$ and $V_{DC2}$. The active clamp on $V_{DC2}$ rail is shown in FIG. 14B. It uses a negative feedback loop to sense a voltage excursion beyond ~1.6 V and, in response, draw more current through $MN_{CLAMP}$ transistor, thereby, limiting $V_{DC2}$ voltage.

Figure 15:
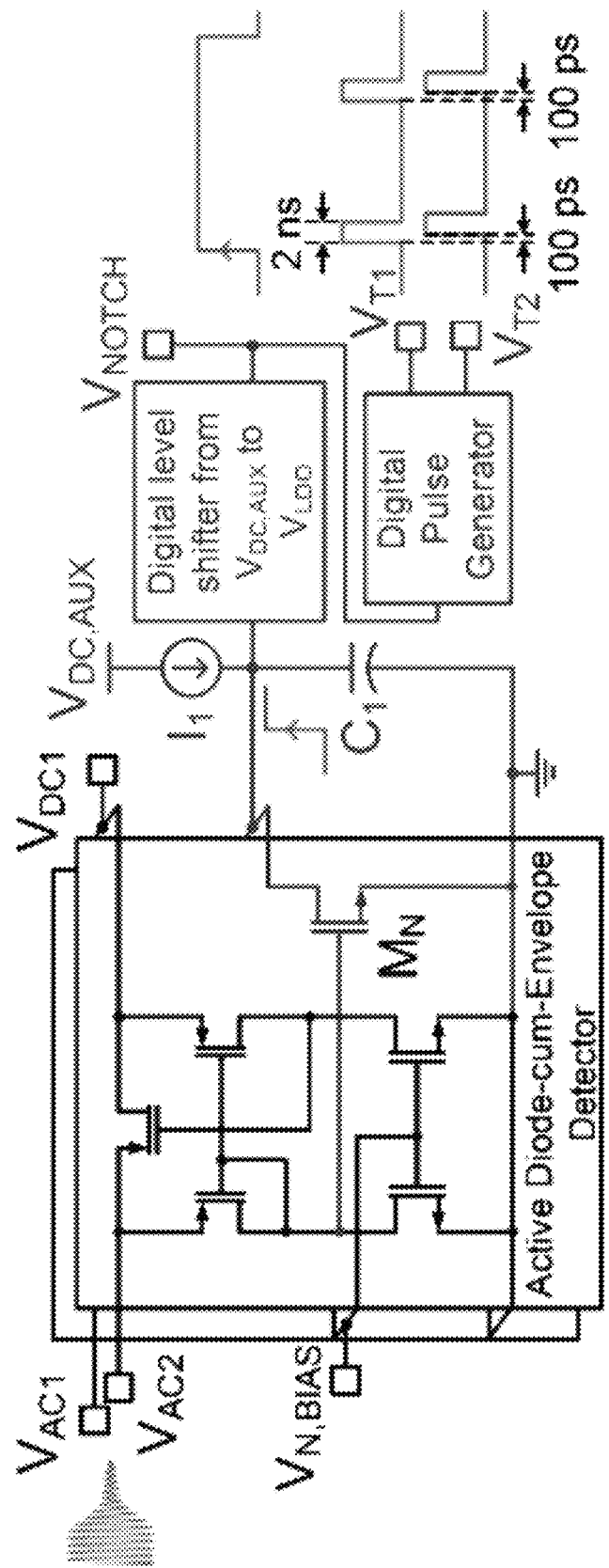
FIG. 15 shows data recovery circuit with envelope detection of ultrasound input and generation of trigger pulses, $V_{T1}$ and $V_{T2}$, according to embodiments of the current invention.

The novel technique of envelope detection for the data recovery circuit, according to the current invention, includes reusing the comparator in the active PMOS diode of the rectifier, as shown in FIG. 15. When the envelope of the AC inputs, $V_{AC1}$ and $V_{AC2}$, falls roughly below the sum of an NMOS and a PMOS threshold voltage, transistor $M_N$ turns off, allowing current $I_1$ to charge capacitor $C_1$ to $V_{DC,AUX}$. As illustrated in FIG. 15, this triggers a digital pulse generator to generate two trigger voltages $V_{T1}$ and $V_{T2}$ with a nominal pulse-width of 2 ns and a fixed inter-pulse delay of 10 ns in post-layout simulations. These trigger voltages serve as "enable" signals for the RF transmitter. $V_{T2}$ is simply a delayed version of $V_{T1}$, with a delay of 100 ps, and is required for the fast startup of the oscillator. The generation of these pulses during startup is avoided by gating the data recovery circuit with the POR signal.

Figure 16:
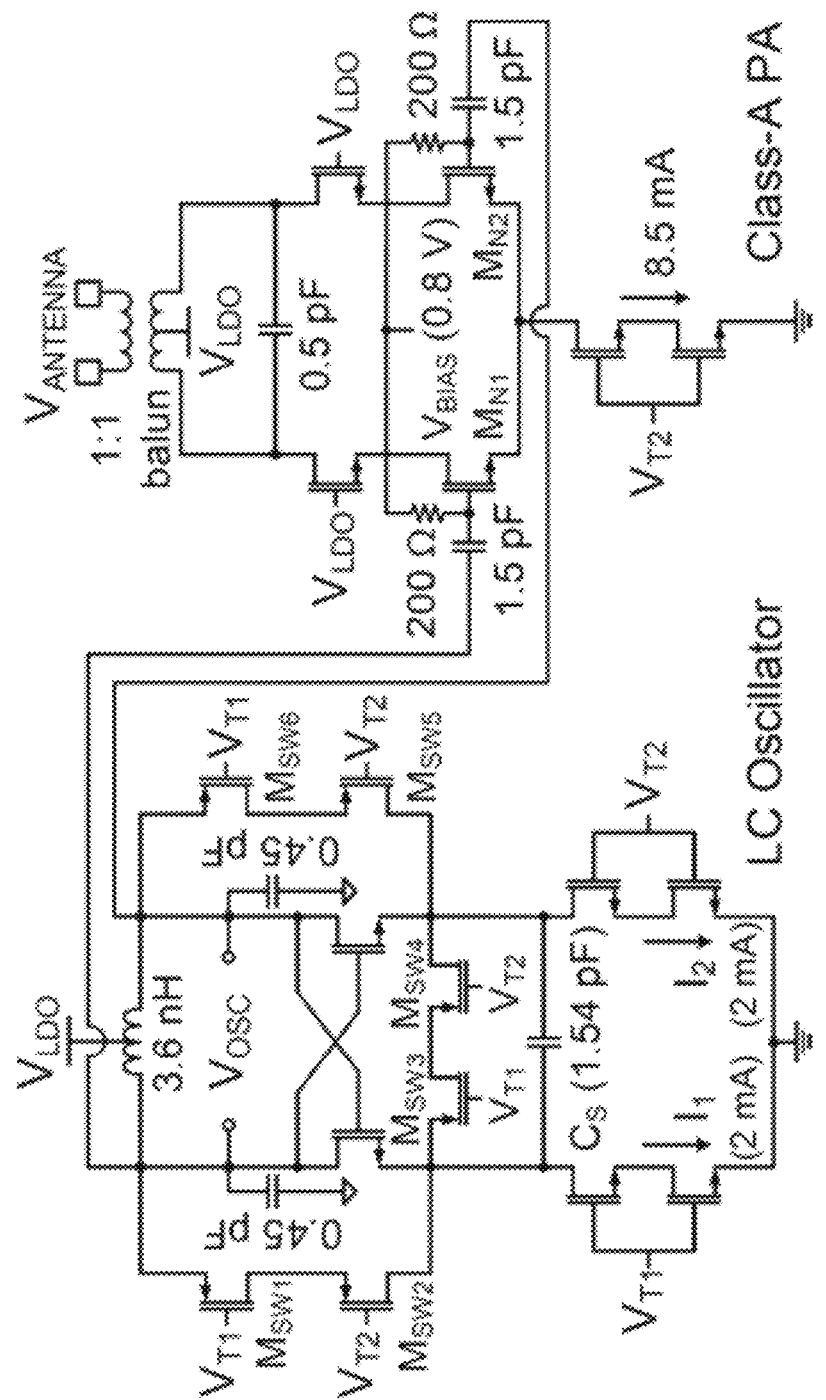
FIG. 16 shows RF data transmitter circuit having the oscillator and the PA schematics, according to embodiments of the current invention.

The RF UWB transmitter, shown in FIG. 16, includes a 4 GHz LC oscillator with a cross-coupled NMOS pair, followed by a power amplifier (PA), both gated by $V_{T1}$ and $V_{T2}$ pulses. A major goal in the design of this transmitter is to minimize its total on-time by ensuring fast startup and turn off of elements that consume a high peak power. The number of cycles required for the startup of a conventional LC oscillator is proportional to the tank Q. However, a pulse width of 2 ns and a carrier frequency of 4 GHz necessitates startup of the oscillator within 3-4 cycles. Therefore, a modified tail current source was used, which provides an asymmetric drive to the oscillator, establishing a large initial condition for oscillations and resulting in a startup time <1 ns. Capacitance $C_S$ in the modified tail current source is sized (1.54 pF) such that it provides a large voltage difference during startup, while minimally degenerating the transconductance of the cross-coupled NMOS transistors in steady-state. In post-layout simulations, the nominal ON-state oscillator current is 4 mA, resulting in a per pulse energy dissipation of <9 pJ (0.9% of the total energy stored on $C_{STOR}$). Switches $M_{SW1}$-$M_{SW6}$ ensure that the oscillator is fully turned OFF when the pulses are not being transmitted.

The PA uses a cascoded class-A topology and was co-designed with the antenna to generate a peak output power between -10 and 0 dBm. Fast startup of the PA is ensured by designing a strong driver for $V_{T2}$ node. The input transistors of the PA are biased at a DC voltage of 0.8 V derived from the resistor divider of the LDO. The high-pass filter at the input of the PA ensures good AC coupling to the oscillator output at 4 GHz. An on-chip 1:1 balun/transformer, with its primary center tap connected to $V_{LDO}$, is designed to interface the PA to the off-chip antenna. The balun provides ESD protection, while also enabling direct measurement of the PA output using a single-ended probe. The nominal PA tail current in post-layout simulations is 8.5 mA, resulting in a per pulse energy consumption of <18 pJ (1.8% of the total energy stored on $C_{STOR}$). The OFF-state leakage power of the PA is limited to <50 nW.

Figure 17B:
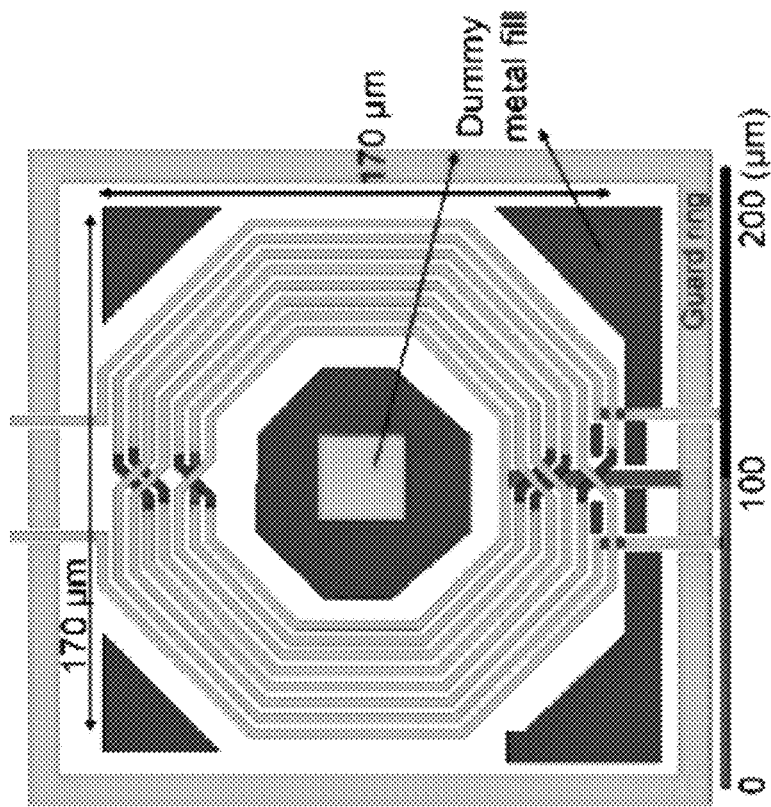
FIGS. 17A-17B shows HFSS simulation setups for the (a) inductor used in the LC oscillator and (b) balun at the output of the PA, according to embodiments of the current invention.
Figure 17A:
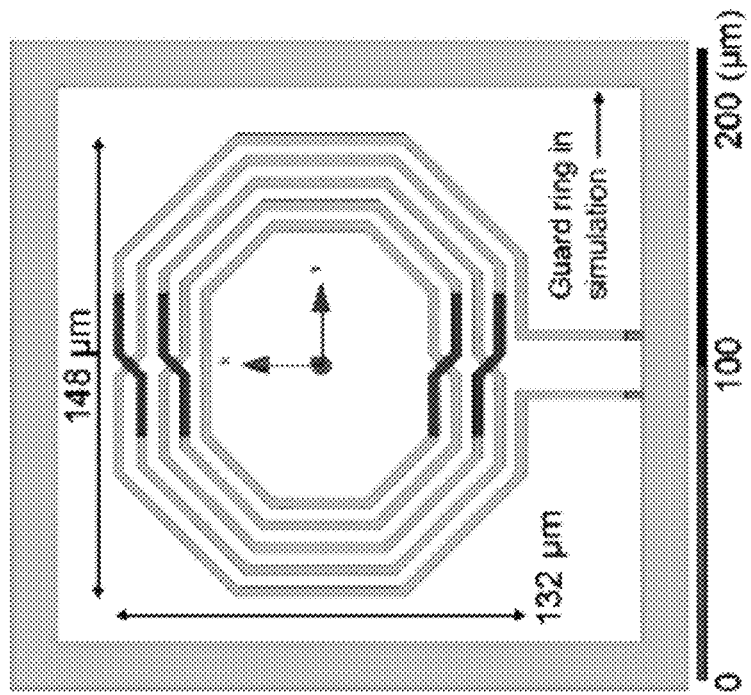

HFSS models of the inductor and balun are shown in FIGS. 17A-17B, respectively. The spiral inductor, designed with 5 turns, a trace width of 3 μm and a spacing between traces of 4 μm, achieves an inductance of 3.6 nH, Q of 11 and a self-resonance frequency of 12.5 GHz. The 1:1 balun has 4 turns on each side, a trace width of 3 μm and a spacing of 2 μm between the primary and secondary turns. At 4 GHz, the balun achieves a coupling factor of 0.88, primary and secondary side inductances of ~3 nH with quality factors of ~10. Epoxy and tissue surrounding the IC were found to have a minimal impact on the inductor and the balun in HFSS simulations.

Small loop antennas of 1.5 mm to 3 mm are used for data uplink for our proof-of-concept system. ANSYS HFSS software was used to simulate a full RF transmission link with the internal implanted antenna, in 3 cm of body tissue, and an external loop antenna. The simulation setup is shown in FIG. 18A. A homogeneous muscle medium was used because no specific application was intended for the embodiment, muscle is abundant around the body in thick layers and is a likely place for implants, and muscle has relatively high loss which will give a conservative link. When designing a miniature implanted antenna, there is a tradeoff in frequency between the electrical length of the antenna and the losses in the tissue. Lower frequency operation results in high-Q impedance and gives poor matching to the PA; however, high frequency operation results in increased body losses. For the example embodiment, antenna sizes between 1.5 mm to 3.0 mm were investigated since they are on the order of IC and piezoelectric receiver dimensions and keep the overall area of the implant small. The frequency range 3.5-4.5 GHz (1 GHz BW for 2 ns pulse) was found to be favorable, for the investigated antenna sizes, since the input impedance to the 2.5 mm antenna was largely real and optimal for the power and voltage levels in our design. FIG. 18B shows the impedance of a 2 mm, 2.5 mm and 3 mm loop from 3.5-4.5 GHz on a Smith Chart. Based on this impedance, a class-A PA was provided to have a favorable load-pull profile for the 2.5 mm antenna, as also shown in FIG. 18B.

After designing the implanted antenna, an external loop receiving antenna was parametrically designed such that high power link gain ($G_p$) in the 3.5-4.5 GHz band was achieved. The external receiver antenna in our system is a square loop of side length equal to 10.5 mm. In future systems, the design of this antenna should be optimized, primarily with the objectives of achieving maximum effective aperture or gain and circular polarization, within the size constraints set by the specific application. FIG. 18C shows $G_p$ over 2-5 GHz, simulated with a load impedance of 50Ω. A transmit power between −10 and 0 dBm was assumed and computed a −71 dBm sensitivity, in a previous section, meaning we needed at least −61 to −71 dB of link gain. As can be seen from the data, all three antenna designs have a link gain much greater than the required value over the entire band. $G_p$ is relatively similar for the three antennas because they all have similar radiation patterns and $G_p$ is normalized to input power to the antenna. Although, the overall received power is greatest for the 2.5 mm antenna, because of the impedance presented to the PA, the other antennas can also be used without significant degradation of received power. Since the implant could undergo small rotations in the body, simulations were also performed with the 2.5 mm antenna at 4 GHz to assess the angular dependence of $G_p$. The antenna was rotated about the x- and y-axis up to 90 degrees (angles labeled in FIG. 18A as $\theta_X$ and $\theta_Y$), and found that $G_p$ was insensitive to angle. Maximum $G_p$ was obtained for the orientation shown in FIG. 18A, and minimum $G_p$ was just ~1.5 dB below maximum $G_p$ at larger values of $\theta_X$ with the loop faces normal to each other. Measurements were also preformed at a few discrete angles and observed that the link was relatively insensitive to angular rotations and misalignment, which is in agreement with simulations.

Figure 19:
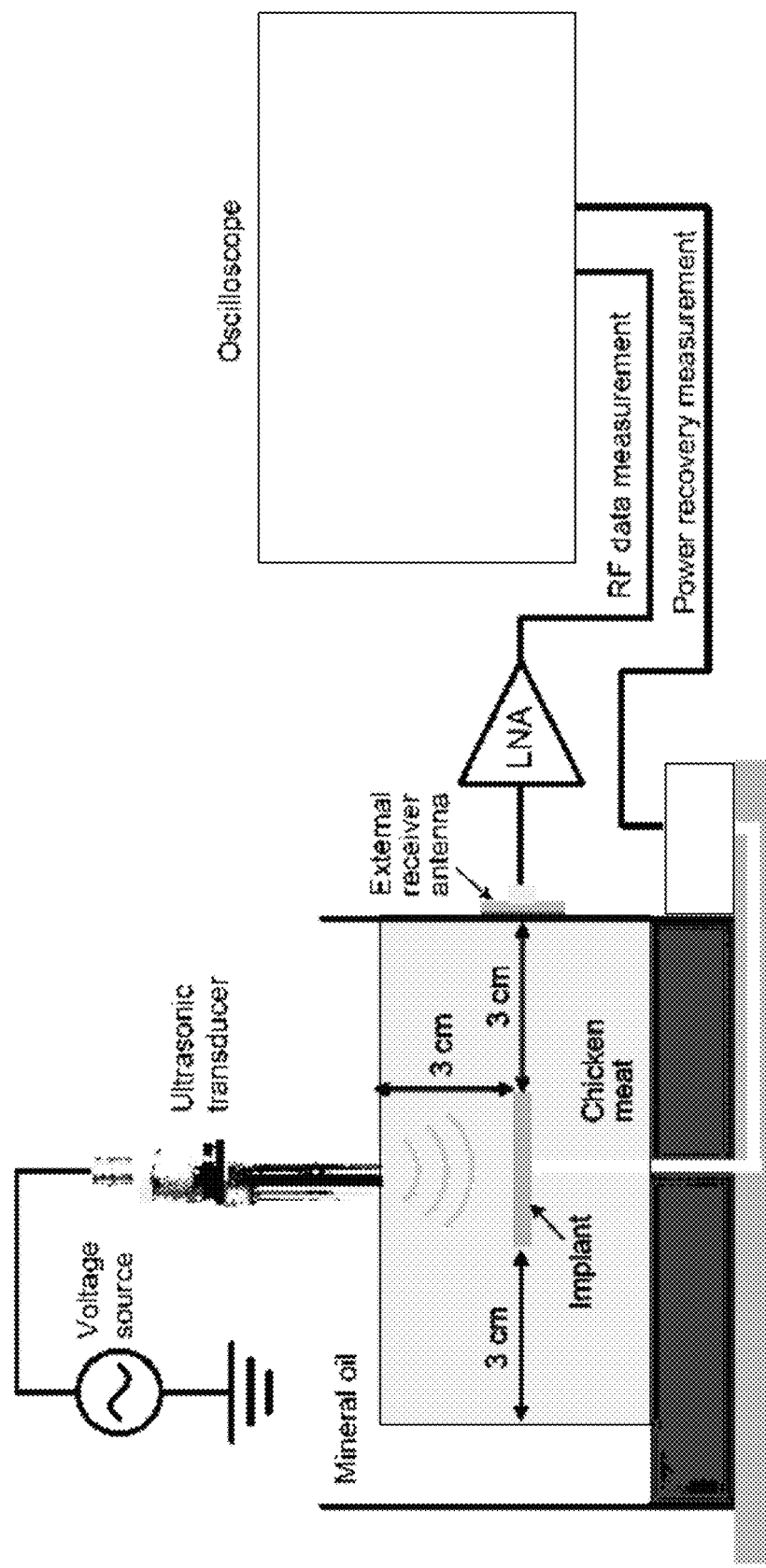
FIG. 19 shows a schematic drawing of a measurement setup for characterizing the implant, according to an embodiment of the current invention.

In order to demonstrate the feasibility of wireless power and data transfer in body, ex vivo measurements of the implant were preformed in chicken meat. Chicken meat is chosen because its acoustic and electromagnetic properties closely resemble those of human tissue. The measurement setup is shown in FIG. 19. Note that while mineral oil is used for acoustic coupling and has a minimal impact on the RF link, in a real scenario, an acoustic matching layer will be used between the wearable ultrasonic transmitter and skin.

The external ultrasonic transmitter (Olympus A303S-SU) is driven at 1 MHz using a signal generator. For varying input power levels, the AC inputs and the DC outputs of the IC are measured for characterizing the performance of the power recovery circuit. An external load resistor is connected to $V_{LDO}$ for characterizing the DC output power capability of the IC. An external RF receiver chain, consisting of an antenna, a low-noise amplifier and an oscilloscope, is used to characterize the performance of downlink data recovery and uplink RF transmitter circuits. Additionally, a blind test of the fully-packaged implant was preformed, embedded in 3 cm of chicken meat on all sides, without accessing any of its terminals using PCB or wires.

Figure 20B:
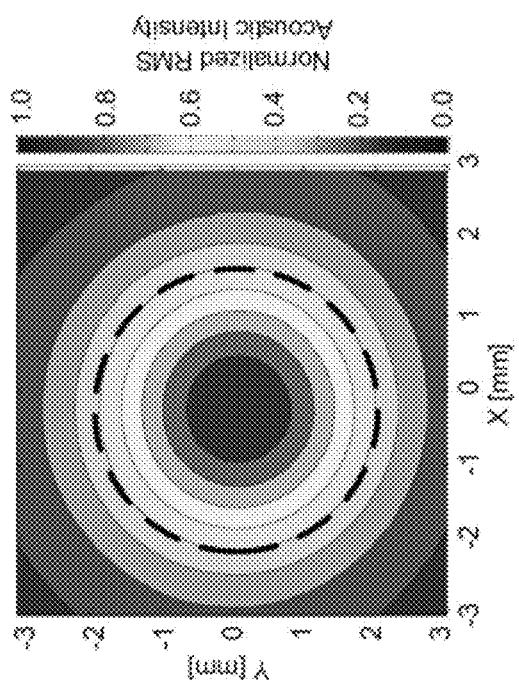
FIGS. 20A-20B show that characterization of the external ultrasonic transducer. (a) Normalized RMS acoustic intensity vs vertical depth, measured in oil medium using a needle hydrophone with an aperture of 1.5 mm diameter. The plot also shows available power for our 1.4 $mm^3$ piezoelectric device through oil and 2.7 cm of chicken meat for an acoustic intensity of mW/mm at 3 cm depth. The device cross-section is mm. (b) Beam profile of the transducer in the horizontal plane at 3 cm depth, showing a focal spot size of 3 mm (dashed circle), according to embodiments of the current invention.
Figure 20A:
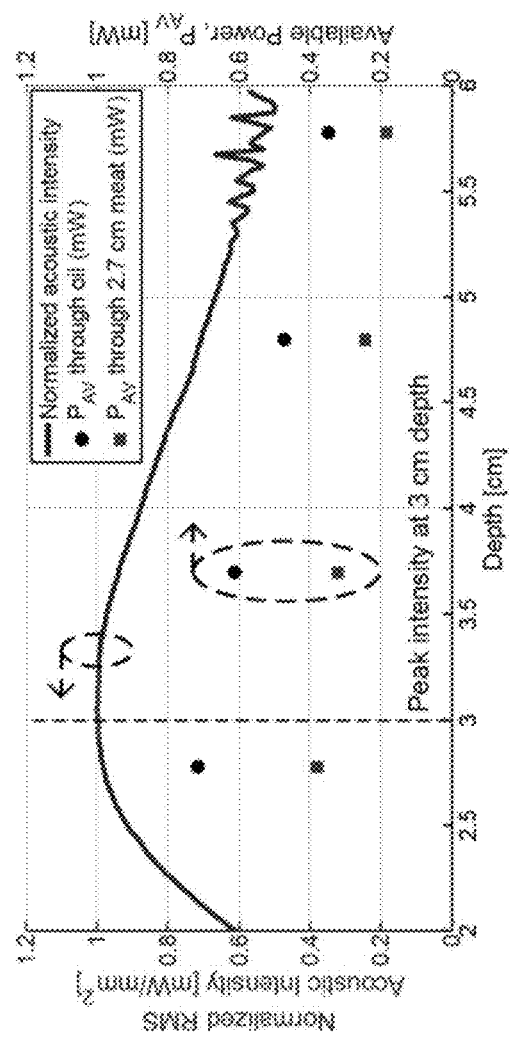

A wideband needle hydrophone was used to characterize the vertical and horizontal beam profiles of our external ultrasonic transmitter, shown in FIGS. 20A-20B. This measurement shows that the maximum RMS intensity is achieved at 3 cm depth, and therefore, our implant measurements are performed at this depth. FIG. 20A also shows the available power for the 1.4 mm$^3$ piezoelectric device, measured through oil and 2.7 cm of chicken meat for an acoustic intensity of 1 mW/mm$^2$ for this transmitter at 3 cm depth. FIG. 20B shows a horizontal beam diameter of ~3 mm for our transducer, resulting in a beam spot size (~7 mm$^2$) which is ~7× larger than the cross-sectional area of our piezoelectric device (1 mm$^2$). In the future, ultrasonic array beamforming can be used for further optimizing the beam spot size in order to maximize link efficiency at greater implant depths (up to 10 cm). However, at larger implant depths, the efficiency of the RF data link may degrade, requiring a careful choice of the RF carrier frequency based on the trade-off between tissue losses and implant antenna size.

Measurement results are presented for our implant system designed using the 1 mm×1 mm×1.4 mm piezoelectric receiver, 1 mm×2 mm IC and square loop antenna sizes of 2.5 mm and 3 mm, packaged together on an FR4 PCB. The die photo of the IC, designed using TSMC 65 nm general purpose (GP) process technology. For characterization tests, components were assembled on a PCB along with connectors for access to all terminals. Measurement results presented in FIGS. 21-24 and FIG. 26A are with this PCB placed inside the oil tank, with the external transducer providing the ultrasound input. Measurement results for bench characterization of the IC are presented in FIG. 25A and FIG. 26B.

Figure 21:
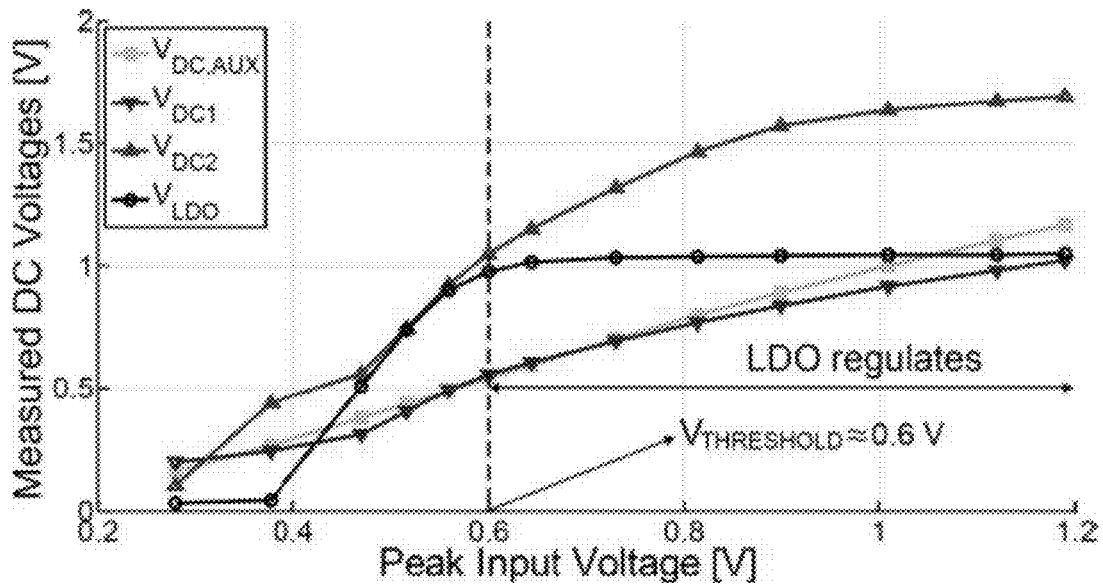
FIG. 21 shows measured DC voltages of the IC as a function of the peak input AC voltage, according to one embodiment of the current invention.
Figure 22:
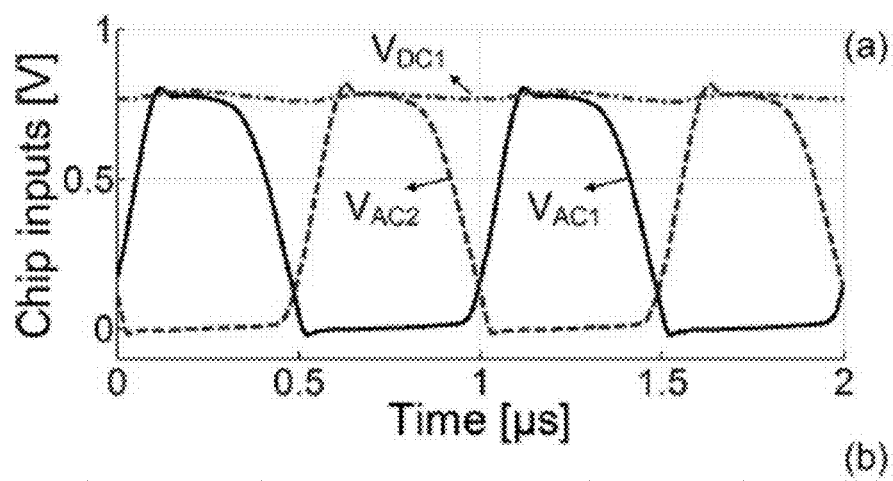
FIG. 22 shows (a) Measured waveforms at the two AC inputs of the IC and the rectifier output voltage $V_{DC1}$. (b) Measured values of peak AC input to the IC and the recovered DC voltages for an incident acoustic intensity of 0.13 mW/mm (18% of FDA limit), according to one embodiment of the current invention.

FIG. 21 shows successful recovery of DC voltages, with no external load on $V_{LDO}$, for peak AC input voltages of the IC ranging from 0.6-1.2 V, as expected from design. FIG. 22A shows measured waveforms of the two AC input voltages of the chip (i.e. at the terminals of the piezoelectric receiver) and the output of the full-wave rectifier for an incident acoustic intensity of 0.13 mW/mm$^2$ (1.8% of the FDA limit) at the implant and no external load on $V_{LDO}$. The voltage conversion efficiency of the rectifier is 97.5%. Measured $V_{DC2}$ (1.49 V) is lower than twice the value of $V_{DC1}$ (0.78 V) because the active voltage limiter at $V_{DC2}$ is partially ON. The output of the LDO is 1.04 V, which is close to the simulated value of 1.0 V. This small difference could be attributed to the susceptibility of the LDO reference voltage to process variations in the constant-gm bias circuit. The value of $V_{DC,AUX}$ in this measurement is 0.69 V, and is lower than its value in FIG. 21 for $V_{IN}$=0.8 V due to process variations, which further motivates the need for generating a regulated DC rail using an LDO in such applications.

Figure 23:
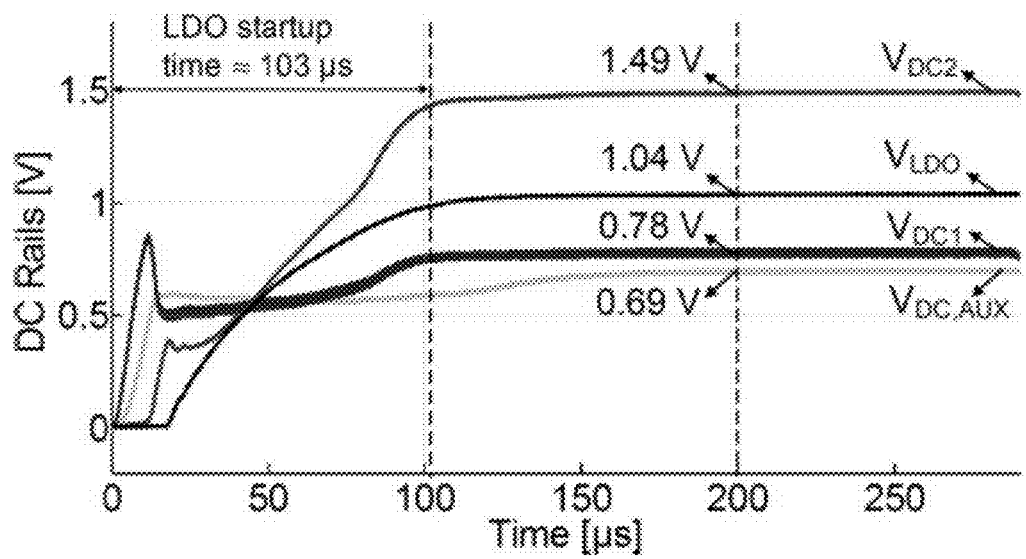
FIG. 23 shows measured startup waveforms of the DC rails for a peak AC input voltage of 0.8 V, according to one embodiment of the current invention.
Figure 24:
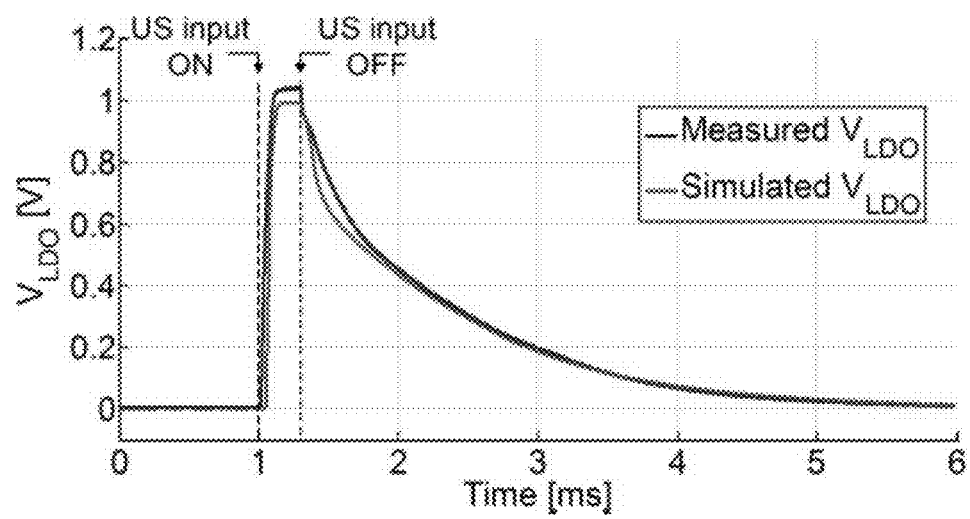
FIG. 24. Shows measured charging and discharging waveforms for the LDO output voltage ($V_{LDO}$) showing good correlation with simulation, according to one embodiment of the current invention.

FIG. 23 shows the measured startup waveforms of the DC rails for a peak AC input voltage of 0.8 V. It can be seen that $V_{LDO}$ settles to 95% of its steady-state value in 103 µs, which is close to the simulation value of 100 µs. In FIG. 24, the startup and discharge profiles of $V_{LDO}$ rail are compared with simulations. For this measurement and simulation, the ultrasound input is turned ON for 300 µs and is subsequently turned OFF for 5 ms. It can be noted that the measured discharge rate of $V_{LDO}$ matches simulation, signifying that the leakage within $C_{STOR}$, as well as the leakage current of circuits powered from $V_{LDO}$ are modeled with good accuracy in simulation.

Figure 26A:
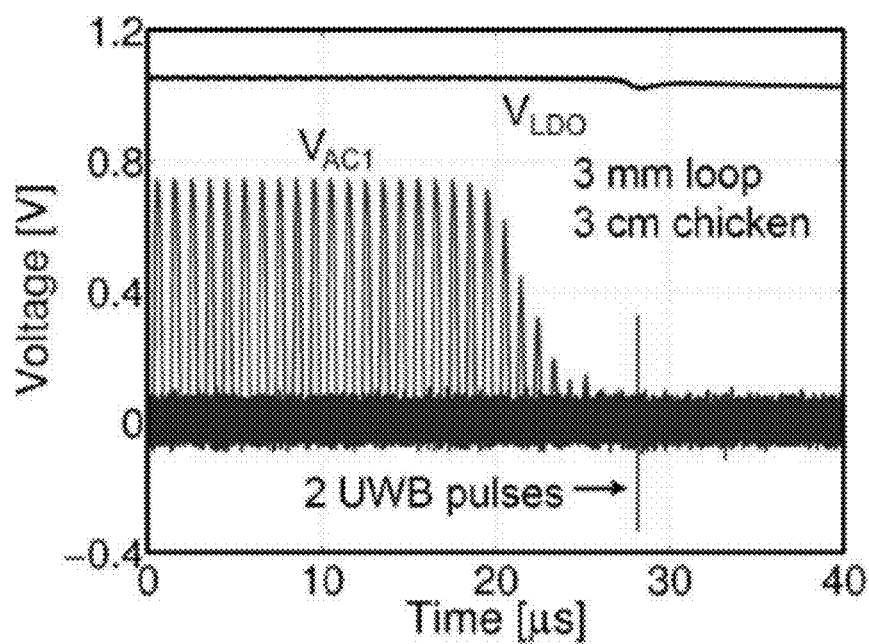
FIGS. 26A-26B show (a) Wireless data recovery and transmission measurement through 3 cm of chicken meat for the implant with 3 mm loop antenna. (b) UWB pulses measured at output of the PA according to one embodiment of the current invention.

Data recovery and transmission of UWB pulses from the implant was demonstrated by modulating the amplitude of the ultrasound input at the external transmitter and detecting the resulting RF pulses via the external RF receiver chain. FIG. 26A shows the falling edge of the ultrasound input and the UWB pulses measured for the implant loop antenna size of 3 mm.

Figure 25A:
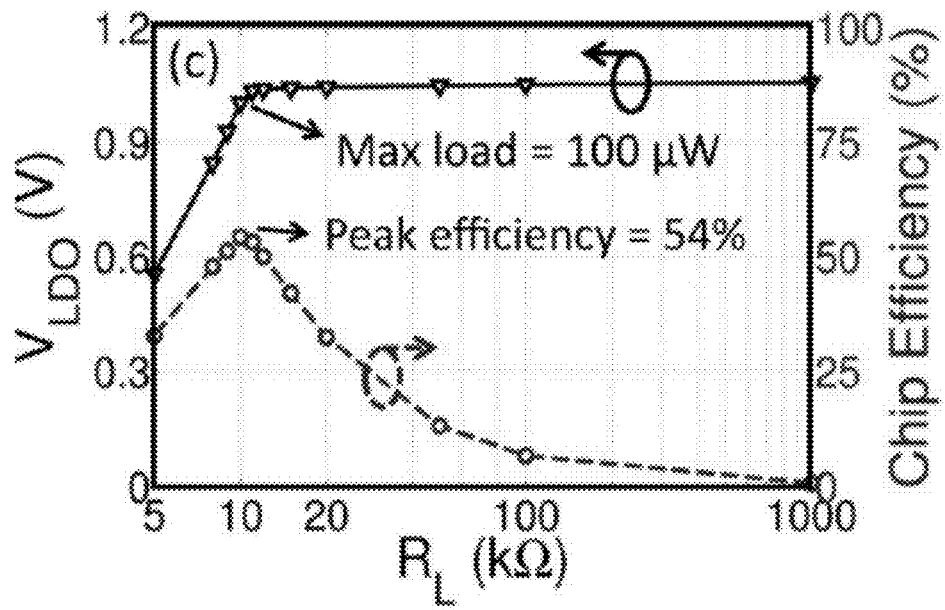
FIGS. 25A-25B show (a) Measured LDO output voltage and the AC-DC conversion efficiency of the IC as a function of the external load resistor connected to $V_{LDO}$. (b) Simulated breakdown of power consumption of the IC, which is 85 W for full load of 100 W according to one embodiment of the current invention.
Figure 25B:
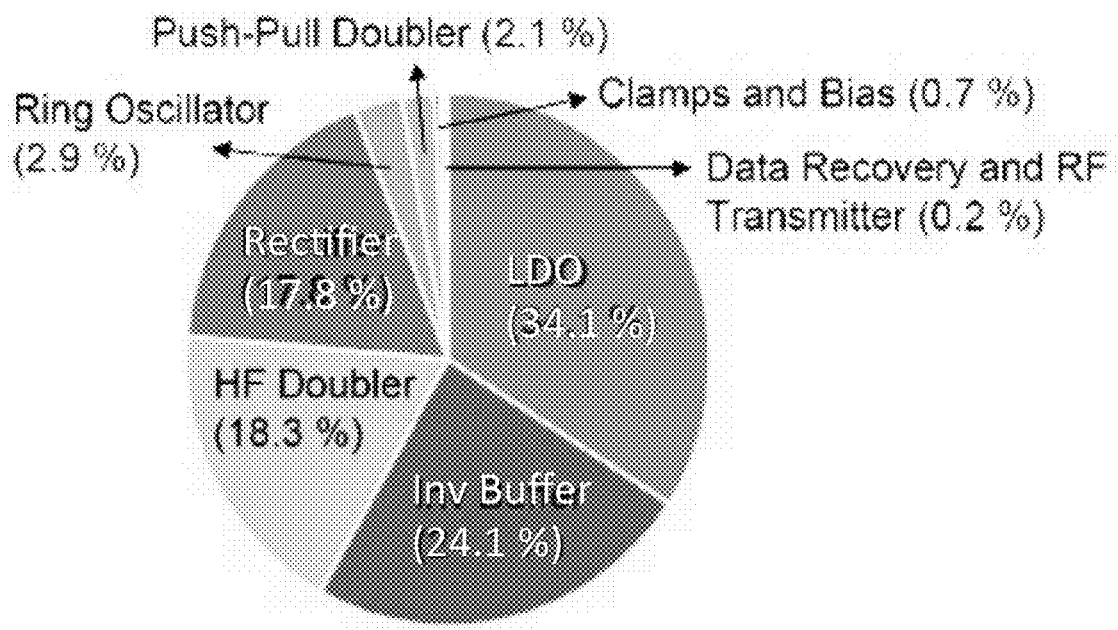
Figure 26B:
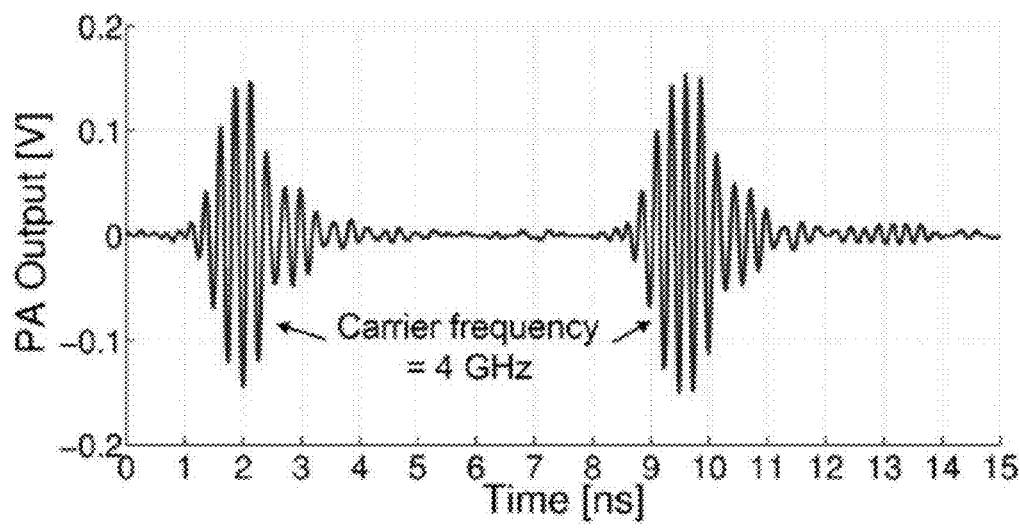

FIG. 25A shows the bench characterization result for the LDO output voltage and the AC-DC conversion efficiency of the IC for varying external load resistance ($R_L$) connected to $V_{LDO}$. The LDO regulates up to a maximum DC load power of 100 µW, as expected. At this full load, the IC achieves a maximum AC-DC conversion efficiency of 54%. As discussed previously, future designs can be optimized for maximizing this efficiency. The measurement with a 100 µW external load connected to the LDO was also performed in the oil tank and required an incident acoustic intensity of 0.36 mW/mm$^2$ (5% of the FDA limit). FIG. 25B shows a breakdown of the simulated power consumption of the IC, which is 85 µW for 100 µW load, highlighting that the largest power consumption (34.1%) is across the pass transistor of the LDO, and that the data communication circuits, which are OFF during ON time of the ultrasound input, consume the lowest (0.2%) percentage of total power. FIG. 26B shows the UWB pulses measured by probing the output of the PA with a $\sqrt{2}$:1 balun and connecting a 50Ω oscilloscope on the secondary side, showing a peak PA output power of −4 dBm after accounting for external losses.

Figure 27A:
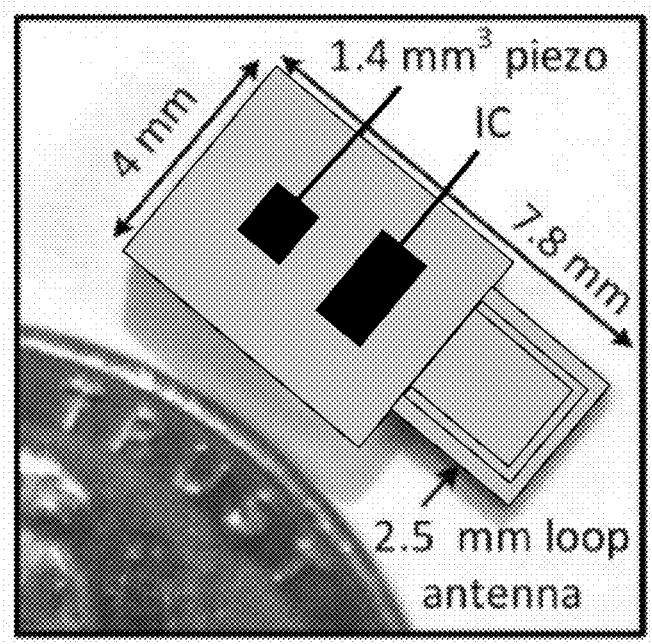
FIGS. 27A-27B show (a) Fully packaged implant. (b) Results of the end-to-end blind test of the fully packaged implant showing successful recovery of UWB pulses at the external receiver according to one embodiment of the current invention.
Figure 27B:
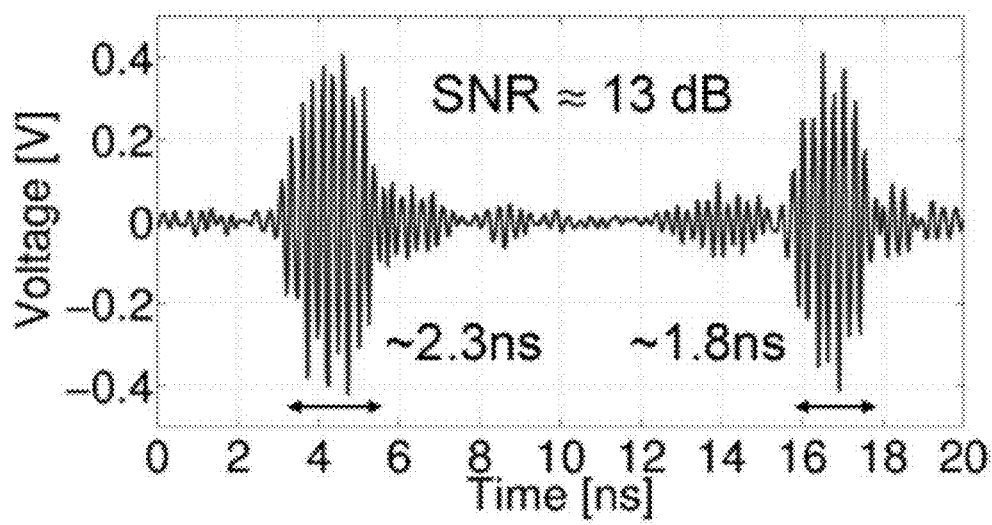

Finally, all components (2.5 mm antenna) of the implant are integrated into a package size of 4 mm×7.8 mm as shown in FIG. 27A. The piezoelectric device is placed inside a through-hole of the PCB, chip-on-board assembly is used for the IC and the loop antenna is fabricated using a copper trace on the FR4 PCB. The two terminals of the piezoelectric device are interfaced to the two input terminals of the IC by using a copper foil and conductive epoxy for the bottom terminal and a bondwire for the top terminal. Further, the piezoelectric device and the IC are encapsulated in Sylgard 184 for protecting the bondwires and because Sylgard has minimal impact on their properties. The weight of our fully-packaged implant is 0.07±0.01 g. The fully wireless blind test performed for this implant, without any access to its terminals, demonstrates successful power transfer and bi-directional data communication capability. UWB pulses from this measurement, shown in FIG. 27B, were received with an SNR of ~13 dB through precisely 3 cm of chicken meat and another 3-4 mm of glass, as shown in the measurement setup of FIG. 19.

The dimensions of the implant can be further scaled down depending on the application requirements. UWB pulses have been successfully measured with smaller loop antennas down to 1.5 mm. Also, as discussed before, a 0.5 mm$^3$ piezoelectric receiver is provided with high available power and ~kΩ range resonant impedance. Smaller piezoelectric receivers will typically require a higher ultrasound frequency, which can result in smaller areas for on-chip capacitors. However, high frequency operation will result in higher tissue losses as well as degradation of the PCE of the IC due to lower available power and input voltage levels. This will require further investigation of external transmitter design and low-voltage circuit techniques for optimizing the link and IC efficiencies. Moreover, reducing the size of the IC by implementing a part of the storage capacitor off-chip, and performing a full 3D integration of the package can allow further miniaturization of the implant.

In summary, a first proof-of-concept demonstration of a mm-sized implantable device, using ultrasound for power transfer, and a hybrid bi-directional data communication link, is disclosed. Ultrasonic power transfer is ideal for providing high power levels (100 µW-a few mWs) to mm and sub-mm sized implants operating deep inside the body (up to ~10 cm). A hybrid data link consisting of ultrasonic downlink and RF uplink was proposed in this design. The RF uplink protocol includes transmitting UWB pulses, demonstrating the feasibility of implementing an energy-efficient PPM transmitter in the future. Our current implant prototype supports a maximum measured DC load power of 100 µW while operating at an incident acoustic intensity of ~5% of the FDA diagnostic ultrasound limit. Our current fully-packaged implant has dimensions of 4 mm×7.8 mm. Successful end-to-end tests were performed for the fully-packaged implant, completely embedded in chicken meat (which emulates human tissue). Potential for further miniaturization of the implant is confirmed by our measurements with smaller piezoelectric receivers and antennas, and the possibility of 3D integration of components.

Turning now to the design of tunable ultrasonic receivers for efficient powering of implantable medical devices with reconfigurable power loads. Miniaturized ultrasonic receivers are designed for efficient powering of implantable medical devices with reconfigurable power loads. Design parameters that affect the efficiency of these receivers under highly variable load conditions, including piezoelectric material, geometry, and operation frequency, are provided. Measurements were performed to characterize electrical impedance and acoustic-to-electrical efficiency of ultrasonic receivers for off-resonance operation. Finally, adaptive matching and frequency tuning techniques are provided using two different reconfigurable matching networks for typical implant loads from 10 µW to 1 mW. Both simulations and measurements show a significant increase in total implant efficiency (up to 50 percentage points) over this load power range when operating off-resonance with the proposed matching networks Implantable medical devices (IMDs) employing neuromodulation therapies, or "electroceuticals," may supplant drugs as the primary treatment for many neurological disorders. Unlike drugs, which freely diffuse about the body, neuromodulation therapies are more targeted, allowing for the mitigation of unwanted side-effects. There are already many neuromodulation devices on the market or in development to treat disorders like Parkinson's and chronic pain however, some of them are large, invasive, and prone to causing infection. In order to alleviate these issues, the current invention provides implants down to millimeter or sub-mm sizes and replaces bulky batteries with reliable and highly efficient wireless power links. Previously researchers have focused on RF or inductive powering. Provided herein, ultrasonic power delivery has several key advantages over conventional RF and inductive powering when shrinking down to the mm-scale. Namely, ultrasound undergoes relatively small propagation losses through tissue (~1 dB·MHz/cm) and has a high FDA allowed time-averaged intensity (7.2 mW/mm$^2$), making it ideal for efficient power transmission at great depths (>5 cm). Additionally, ultrasound has small wavelengths in tissue (e.g. 1.5 mm at 1 MHz) allowing for superior energy focusing down to mm-spots, as well as more efficient energy recovery from a ultrasonic receiver.

Current and future IMDs may be equipped with several functionalities, such as electrical or optical stimulation, neural recording, and temperature and pressure sensing within one module—these functions require a large range of average implant load ($P_{load}$) typically ranging from 10 µW to 1 mW. In addition, next-generation IMDs will be programmable with duty-cycled operation and different functional modes, leading to dynamically varying $P_{load}$ for an individual IMD. Static links can become inefficient with large load perturbations due primarily to impedance mismatch between the power receiver and the non-linear power recovery chain. As demonstrated herein, an implant optimally matched for 1 mW achieves less than 5% efficiency when operated at 10 µW. Low efficiency is a major reliability problem, leading to significantly reduced battery life of the external source and potential loss of function of the IMD if the required power cannot be achieved. Therefore, an ideal power receiver should be tunable, along with the source, to maximize the power matching efficiency over a wide variety of applications and dynamic loads.

With proper choices of material and dimensions, a piezoelectric ultrasonic receiver can be designed to be mm-sized with an optimal electrical impedance for a highly variable load. In addition, by using frequency as a degree of freedom, demonstrate off-resonance operation to modulate the receiver impedance for adaptive matching is demonstrated herein. In contrast, mm-sized implantable antennas, which are typically operated in the low-GHz range to combat tissue loss, offer much smaller radiation resistance and efficiency, due to mismatch in aperture and wavelengths as well as dielectric loading.

An implant power recovery chain for an IMD is provided, and the impedance consider the effect of average $P_{load}$ on the input impedance of the power recovery circuit and demonstrate the concept of off-resonance operation for adaptable impedance tuning is described. Then a design procedure is presented to achieve the impedance specifications with a piezoelectric receiver. The selection of material and dimensions for ultrasonic receivers greatly influences frequency of operation and the impedance tuning range, so several different materials, including bio-compatible options, are compared. Later, two adaptive matching topology examples are provided to show significant improvement in the total implant efficiency over a non-tunable power recovery chain.

Figure 28:
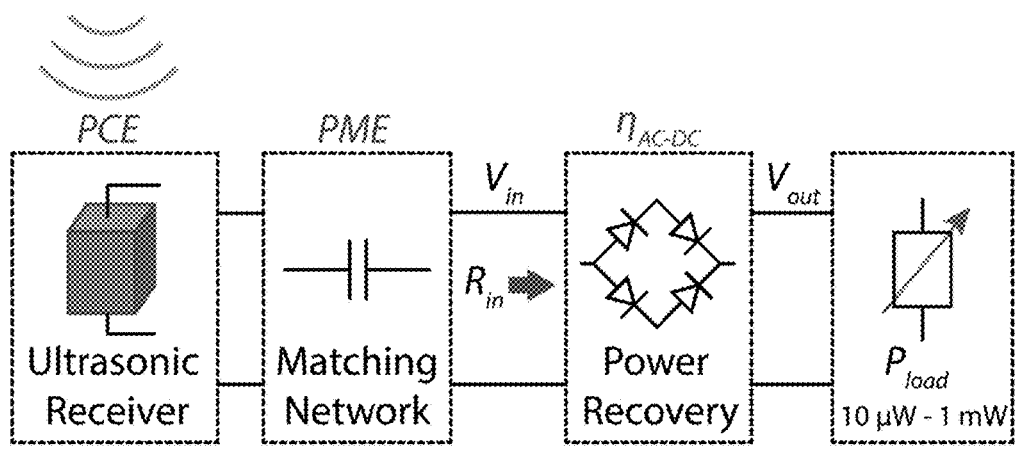
FIG. 28 shows a schematic diagram of an ultrasonic power recovery chain. An effective load impedance, $R_{in}$, models the non-linear power recovery circuits, along with the implant power load, $P_{load}$ according to one embodiment of the current invention.

A schematic diagram of an ultrasonic power recovery chain for an IMD in the steady state is shown in FIG. 28, which includes a piezoelectric receiver, a matching network, power recovery circuits, and an average application load. The total implant efficiency ($\eta_{implant}$) is determined by three major components: the acoustic-to-electrical power conversion efficiency of the receiver (PCE), the efficiency of the power recovery circuit ($\eta_{AC-DC}$), and the power matching efficiency (PME) between the first two components. Therefore, $\eta_{implant}$ can be represented as, $$\eta_{implant} = \frac{P_{load}}{P_{acou} = PCE \cdot PME \cdot \eta_{AC-DC}}, \qquad (2)$$

where $P_{acou}$ is the total incident acoustic power on top of the receiver. There is extensive literature on designing power electronics for power receivers to achieve high $\eta_{AC-DC}$; hence, focus is placed on optimizing efficiency of the ultrasonic receiver and impedance matching interface due to the large variation of $P_{load}$ in an IMD.

A first-order calculation can be made to model any non-linear power recovery circuits, along with the implant load, as an effective average load impedance ($R_{in}$) annotated in FIG. 28 using the following equation, $$R_{in} \simeq \frac{V_{in}^2}{2P_{load}}\eta_{AC-DC}, \qquad (3)$$

where $V_{in}$ is the peak input rectified voltage. As a first-order estimation, when assuming a peak input of 2 V and $\eta_{AC-DC}$ of ~80%, the effective resistance can be computed from (3) to be between ~200 kΩ and ~2 kΩ for 10 µW to 1 mW load powers. An input voltage of 2V is assumed since it is much greater than typical CMOS thresholds, allowing for high $\eta_{AC-DC}$ (>80%) while also remaining below typical CMOS technology voltage limits. This calculation and the approximations are sufficient for our purpose of getting a first-order estimate of the effective implant load since modest differences do not greatly influence the PME and further refinements can be made using circuit simulators.

Figure 29:
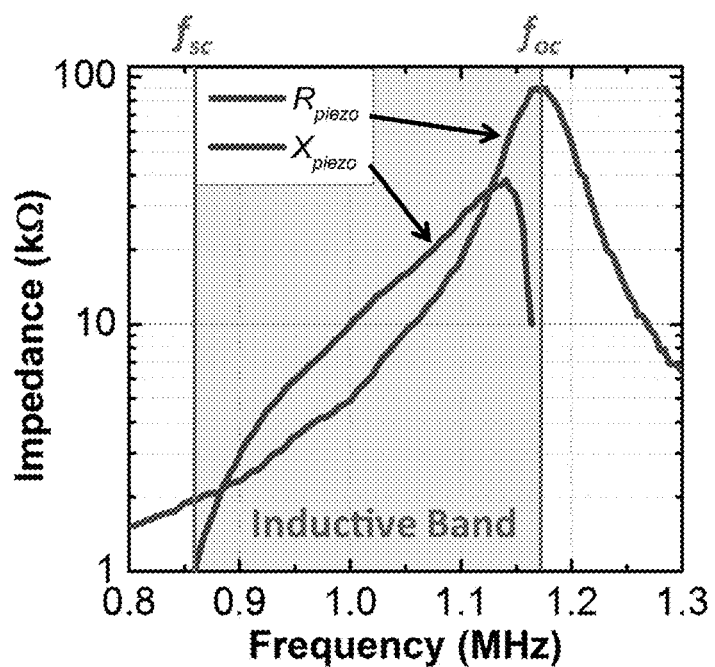
FIG. 29 shows impedance plot of a 1.5 mm×1.1 mm×1.1 mm ultrasonic receiver made from PZT5H measured with an impedance analyzer (Agilent 4294A). The shaded region indicates the inductive band (IB) for off-resonance tuning, according to one embodiment of the current invention.

In order to achieve a high PME over the wide range of $R_{in}$, a power receiver should exhibit a similar impedance range as $R_{in}$. FIG. 29 shows an example measured impedance profile of a mm-sized ultrasonic receiver made from Lead Zirconate Titanate 5H (PZT5H), a piezoelectric material, with dimensions of 1.5 mm×1.1 mm×1.1 mm. As seen in the figure, there is nearly two orders of magnitude change in the real part of the impedance ($R_{piezo}$) between the short-circuit ($f_{sc}$) and open-circuit ($f_{oc}$) resonances. The large value and range of $R_{piezo}$ offers a significant advantage for powering various $P_{load}$. With the appropriate design methodology to choose material and dimensions of the ultrasonic receiver, $R_{piezo}$ can be tuned to match the targeted $R_{in}$ range. Furthermore, the inherent inductive nature of a piezoelectric receiver operating around mechanical resonance can be leveraged, in a band hereinafter referred to as the inductive band (IB), for impedance matching to obtain high PME. Conventionally, passive reactive components are used in order to perform impedance matching. Though large inductance around MHz is not practical when the form factor of implantable device is limited to mm-dimensions, capacitance is easy to obtain in a small volume or even on chip. The large inductive reactance with a reasonable quality factor in the IB, allows for impedance transformation with purely capacitive matching networks. Depending on the operating frequency and the topology of matching network, the required matching capacitance ranges only from ~1 pF to 40 pF. The details of the matching network design will be described below.

TABLE 2

MATERIAL PROPERTIES FOR LENGTH EXPANDER BAR MODE [33]

| | PZT4 | PZT5H | BaTiO$_3$ | LiNbO$_3$ |
|---|---|---|---|---|
| Density, ρ (kg/cm$^3$) | 7500 | 7500 | 5700 | 4640 |
| Sound Velocity, v (m/s) | 4100 | 3850 | 5000 | 6400 |
| Acoustic Impedance, Z$_C$ (MRayls) | 30.8 | 28.9 | 28.5 | 29.7 |
| Electrical-Mechanical Coupling Coefficient, k$_{33}$ | 0.70 | 0.75 | 0.5 | ~0.5 |
| Relative Permittivity, ε$^T$ | 1300 | 3400 | 1700 | 30 |
| Mechanical Quality Factor | 500 | 65 | 300 | >1000 |

Disclosed herein is how to obtain the impedance behavior discussed in above by introducing a first-order circuit model that aids with the design process. The model provides sufficient accuracy for capturing the frequency behavior of the impedance and the radiation resistance of the piezoelectric receivers.

Figure 30:
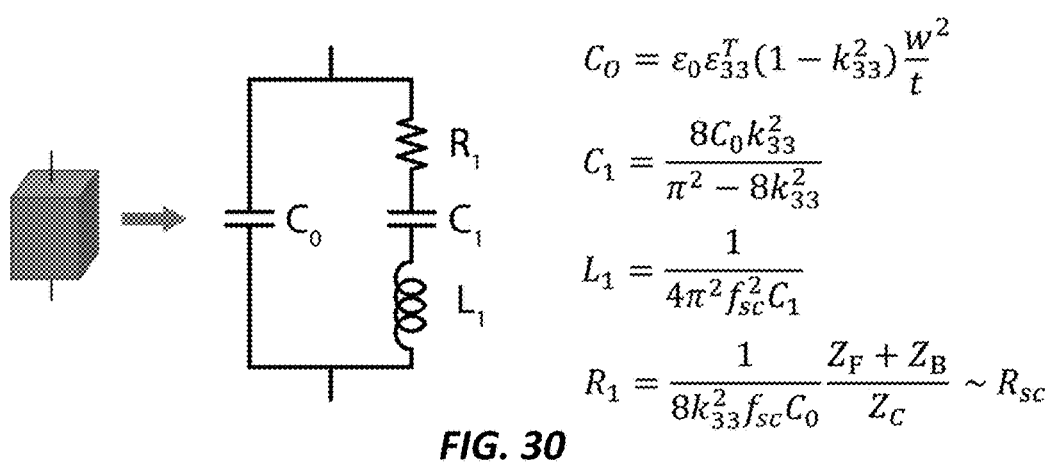
FIG. 30 shows a schematic diagram of the one-dimensional series circuit model around fundamental resonance. The circuit elements are functions of material constants with length expander mode and dimensions as shown in the equations, according to one embodiment of the current invention.

The one-dimensional series circuit model shown in FIG. 30 is used for first-order design of the piezoelectric receivers around fundamental resonance. The model is comprised of a series RLC tank with the intrinsic capacitance of the device ($C_0$) in shunt. The circuit element values are determined by width (w) and thickness (t) of the device, the piezoelectric material properties: relative permittivity ($\varepsilon^T$), electrical-mechanical coupling constant ($k_{33}$), acoustic impedance of the material ($Z_C$), front acoustic loading ($Z_F$), and back acoustic loading ($Z_B$). The model is more accurate when $Z_F$, $Z_B \ll Z_C$. This condition is satisfied in the design as the front of the device is loaded by tissue ($Z_{tissue} \approx 1.4$-$1.6$ MRayls) when implanted in the body, and the receiver is designed with air backing ($Z_{air}$=400 Rayls) to minimize the effect of mechanical damping. Using this model, four different materials are investigated, PZT4, PZT5H, Barium Titanate (BaTiO$_3$), and Lithium Niobate (LiNbO$_3$), and compare their performances as ultrasonic receivers for IMDs. PZT4 and PZT5H are common piezoelectric materials widely utilized in imaging and sensor transducers. BaTiO$_3$ and LiNbO$_3$ are lead-free piezoelectric materials and are potentially biocompatible. The material properties, assuming length-expander bar mode (LE mode) operation, are listed in Table 2. LE mode is utilized here as it provides better approximation when the aspect ratio of the receivers (G=w/t) is constrained below unity in order to reduce the overall implant volume.

The thickness of the receivers, t, and the sound velocity of the piezoelectric materials, v, are the main parameters for positioning the fundamental resonance. The $f_{oc}$ and $f_{sc}$ for G≪1 are given as, $$f_{oc} = \frac{v}{2t'} \quad (4)$$

$$f_{sc} \simeq \sqrt{1 - \frac{8k_{33}^2}{\pi^2}} f_{oc'} \quad (5)$$

where $f_{sc}$ is lower in frequency than $f_{oc}$, and they are related by $k_{33}$, which in turn determines the span of the IB. The resonance frequencies are inversely proportional to thickness of the material; thus, thinner devices have higher operating frequency. Due to mode coupling from finite width, the fundamental resonances will shift to slightly lower values for a practical aspect ratio. A correction factor of 1 to 0.7 for G≤1 can be inserted into (4) and (5) for more accurate determination of resonances. Nonetheless, this small shift does not have significant impact on the design process.

The goal is to operate the devices with an IB between ~1-2 MHz as a trade-off between acoustic propagation losses through soft tissue (~1 dB MHz/cm) and overall implant thickness. Based on equations above, and the material velocities listed in Table 2, the IB can be positioned sufficiently close to the target range for all four materials using a thickness of 1.5 mm. Table 3 shows the calculated 1-D resonance frequencies for different materials. Receivers made from PZT4 and PZT5H have lower resonance frequencies than those made from BaTiO$_3$ and LiNbO$_3$ due to lower sound velocity.

The area of the ultrasonic receiver and piezoelectric materials offers another trade-off between implant size and power capture area. As an example demonstration, we choose a lateral dimension, w, of 1.1 mm and use material as a design parameter to achieve the desired impedance range. Shown in FIG. 29, the off-resonance resistance in the IB is bounded by short circuit resistance, $R_{sc}$, and open circuit resistance, $R_{oc}$. Using the chosen dimensions, acoustic loadings, and the material properties in Table I, $R_{sc}$ and $R_{oc}$ can be calculated with the following equations derived from the series circuit model, $$R_{sc} \cong \frac{1}{8k_{33}^2 f_{sc} C_0} \frac{Z_F + Z_B}{Z_c} \propto \frac{1}{\rho v^2 \varepsilon^T k_{33}^2 (1-k_{33}^2)^{\frac{3}{2}}} \frac{t^2}{w^2} \quad (6)$$

$$R_{oc} \cong \frac{2k_{33}^2 f_{sc}}{\pi^2 f_{oc}^2 C_0} \frac{Z_c}{Z_F + Z_B} \propto \frac{\rho k_{33}^2}{\varepsilon^T (1-k_{33}^2)^{\frac{1}{2}}} \frac{t^2}{w^2}. \quad (7)$$

Equations (6) and (7) also show the direct relationship of $R_{sc}$ and $R_{oc}$ to the material properties under the assumption of given acoustic loadings (i.e. tissue and air for front and backing loading respectively). The calculated values for a thickness of 1.5 mm and width of 1.1 mm are shown in Table 3. $R_{sc}$ and $R_{oc}$ are similar for receivers made from PZT4, PZT5H, and BaTiO$_3$; in addition, these materials offer an off-resonance resistance range that is well-matched to the desired $R_{in}$ from above. Conversely, the resistances for receivers made from LiNbO$_3$ are nearly two orders of magnitude higher due to drastically lower relative permittivity as captured by the equations above. Although increasing the area of the piezoelectric receivers can be used to lower impedance range, this is undesirable for the purpose of miniaturization. Therefore, LiNbO$_3$ is not a preferred material for mm-sized implants of the specific targeted power range in the paper, while PZT4, PZT5H, and BaTiO$_3$ are well-suited for our applications.

The above arguments are not meant to be a comprehensive analysis of all piezoelectric materials and sizing, but are added to demonstrate various tradeoffs given a target power level and volume. Depending on the requirements of the application, a similar analysis can be carried out to investigate the feasibility of different materials and dimensions. For example, with the given dimensions, single crystalline piezoelectric materials such as PMN-PT are more suitable for applications requiring a higher power range (>1 mW) due to their large $\varepsilon^T$ (~5000) and $k_{33}$ (~0.9). One can also tune the properties of the piezoelectric materials by utilizing a composite piezoelectric transducer. Additionally, for shallow IMDs (<5 cm), a shorter link reduces the acoustic loss through tissue, and thus, higher frequency operation can be used to further scale down the thickness and width of the receiver while maintaining the desired impedance range.

TABLE 3

CALCULATED RESONANCE AND IMPEDANCE

|  | PZT4 | PZT5H | BaTiO$_3$ | LiNbO$_3$ |
|---|---|---|---|---|
| $f_{sc}$ (MHz) | 1.06 | 0.95 | 1.49 | 1.90 |
| $R_{sc}$ (kΩ) | 2.48 | 1.15 | 1.94 | 82.5 |
| $f_{oc}$ (MHz) | 1.37 | 1.28 | 1.67 | 2.13 |
| $R_{oc}$ (kΩ) | 244 | 119 | 56.6 | 2612 |

*Calculation based on device with t = 1.5 mm, w = 1.1 mm, $Z_F$ = 1.5 MRayls, and $Z_B$~0 MRayls.

Ultrasonic receivers were built using PZT4, PZT5H, and BaTiO$_3$ to compare the general impedance behavior with the first-order analysis. Acoustic-to-electrical power conversion efficiency, PCE, was also measured across the IB for each material. The PCE is defined mathematically as, $$PCE = \frac{P_{av,ele}}{P_{acou}} = \frac{P_{av,ele}}{I_0 A}, \quad (8)$$

where $P_{av,\,ele}$ is, i the available electrical power and P is the incident acoustic power, which is the product of incident acoustic intensity on top of the receiver characterized by a hydrophone, $I_0$, and physical area of the receiver, A. PCE is the acoustic-to-electrical efficiency analogue of aperture efficiency of an antenna. It varies across frequency and does not depend on electrical loading or characteristics of the ultrasonic transmitter so long as the receiver is in the far-field.

Figure 31A:
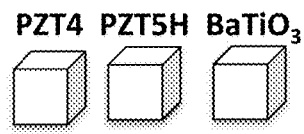
FIGS. 31A-31C show (a) PZT4, PZT5H, and $BaTiO_3$ with dimension of 1.5 mm×1.1 mm×1.1 mm. (b) Diagram and photo of ultrasonic receiver's package. (c) Setup for ultrasonic power transferring measurement. The ultrasonic transmitter is centered above the ultrasonic receiver in an oil tank. $I_0$ is the acoustic intensity on top of the receiver characterized by the hydrophone, according to one embodiment of the current invention.
Figure 31B:
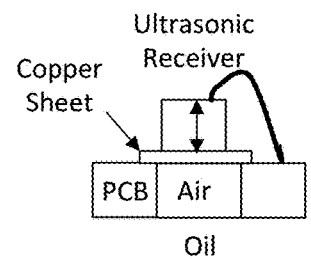

All piezoelectric receivers have a thickness of 1.5 mm, were diced to a width of 1.1 mm, as shown in FIG. 31A, and packaged on top of a print circuit board (PCB). The package was designed to minimize the total volume of the device. A bond wire and copper sheet were used to establish top and bottom electrical connections to receivers' electrodes. Air backing was created by sealing the via hole on the PCB. FIG. 31B shows the diagram of the package.

Figure 31C:
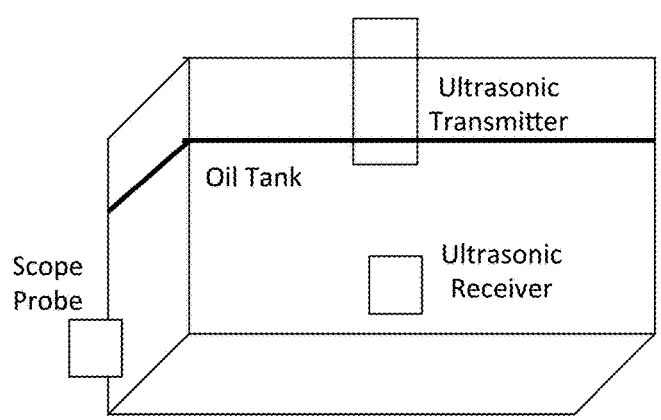

The experimental setup is shown in FIG. 31C. The receiver was immersed in a custom tank filled with mineral oil (1.16 MRayls) in order to minimize electrical parasitics and mimic the acoustic loading of body tissue. The ultrasonic transmitter (Olympus A303S) and the receiver were spaced at a distance of 6.0 cm to ensure both devices are in the far-field region. In practice, one would use a focusing array to get higher link efficiency, but here we are only interested in characterizing the ultrasonic receivers, independent of the transmitter.

Figures 32A, 32B, 32C:
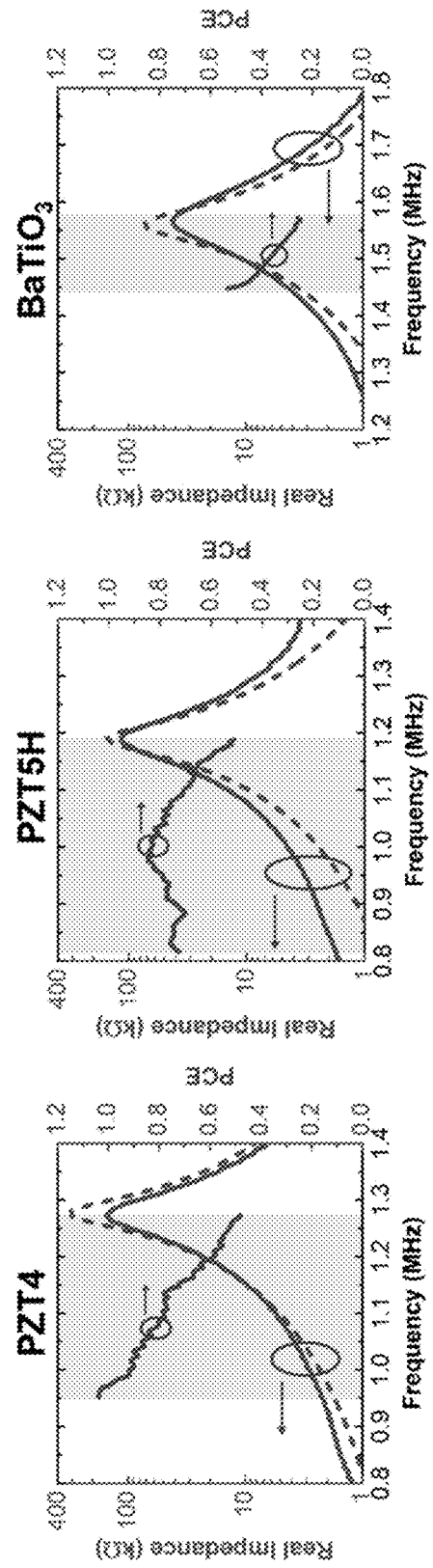
FIGS. 32A-32C show the measured $R_{piezo}$ (blue solid line), the calculated $R_{piezo}$ from the series circuit model (blue dashed line), and the measured power conversion efficiency, PCE (red solid line), of the receivers made from (a) PZT4, (b) PZT5H, and (c) $BaTiO_3$. The IB is shaded in gray.

The impedance profile of the ultrasonic receivers was characterized using an impedance analyzer (Agilent 4294A). FIGS. 32A-32C show the measured and calculated $R_{piezo}$ from the series circuit model with a correction factor of 0.93 (for G~0.7) to correct resonance frequency. The measured IB is highlighted in green and the values of the resonance frequencies, $R_{sc}$, and $R_{oc}$ are listed in Table III. The reactance across the D3 was omitted since a capacitor-only matching network was used to cancel the reactance as described above. The measured $R_{piezo}$ curve has lower mechanical quality factor compared to the first-order model since the model does not take into account the loss from material and package. Nonetheless, the range of measured $R_{piezo}$ agrees reasonably well with the first-order model. For each material, $R_{piezo}$ spans much of the ~2 kΩ to ~200 kΩ targeted range in the IB, suitable materials all present high PCE with variation across the entire IB. Similar to aperture efficiency for antenna, PCE larger than unity is possible for small resonators. As an example, even with a worst case PCE of 30%, we are still able to obtain 1 mW of time-averaged available power with less than 40% of the FDA limit (7.2 mW/mm$^2$). The PCE plots indicate that off-resonance operation can be utilized to transfer power efficiently for various $P_{load}$.

Turning now to a single transducer for data and power in wirelessly powered devices. According to the current invention "positive reactance band" of an acoustic transducer is defined as any frequency band in which the acoustic transducer provides a positive reactance (i.e., has a positive imaginary part of its electrical impedance). Further, an "inductive band" of an acoustic transducer is defined as any positive reactance band of the acoustic transducer +/−20% in frequency. More specifically, if the positive reactance band is $f_1 \le f \le f_2$, the corresponding inductive band is 0.8 $f_1 \le f \le 1.2 f2$.

Figure 33:
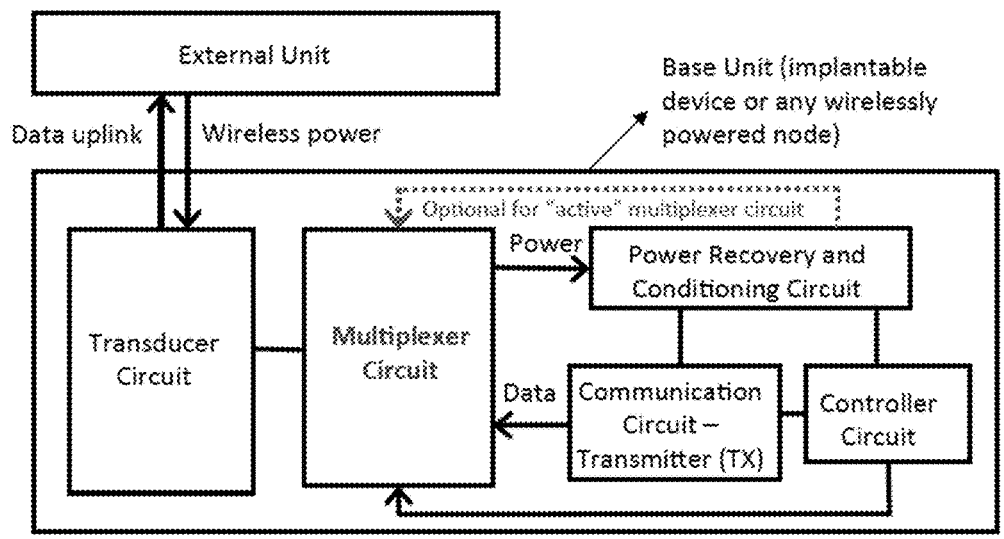
FIG. 33 shows a schematic drawing of a wirelessly powered device having a single transducer power recovery and "active" uplink data communication, according to one embodiment of the invention.

According to the current invention, a wirelessly powered device is provided that includes a single transducer that is used for power recovery and "active" uplink (UL) data communication as shown in FIG. 33. In this context, "active" uplink communication refers to the scenario where the wireless power recovered by the device is used to transmit active data signals to an external unit. In some embodiments, the same transducer is also used for downlink (DL) data communication, or sensing, or stimulation, or a combination of these functions. In this embodiment, the transducer circuit receives or harvests power from the external unit. The current invention relates specifically to a single transducer with a single port or feed, which is used for both wireless power recovery and uplink data transmission in the most general case. In some embodiments, the same port or feed of the single transducer could also be used for downlink data communication, or sensing, or stimulation, or a combination of these functions. A distinction is made with dual-band or multi-band antennas that are typically used for uplink and downlink data communication, and for maximizing the data communication bandwidth. Wireless power recovery through the single transducer (with a single port or feed), in addition to data communication, is the major distinguishing feature between the current invention and other implementations that may use dual-band antennas for bi-directional data communication.

The multiplexer circuit de-couples the data and power paths, which is necessary for operation with a single transducer circuit. In some embodiments, the multiplexer circuit is "active", i.e. it is powered from the power recovery and conditioning circuit, where the power recovery and conditioning circuit receives electrical power from the transducer circuit and converts it into a usable form for powering other circuits included on the base unit. This operation may include conversion of the AC voltage at the terminals of the transducer to a DC voltage and/or storage of energy on a storage element such as a capacitor or a rechargeable battery. The communication (or Comm) circuit-Transmitter (TX), powered from the power recovery and conditioning circuit, transmits "active" uplink data signals, via the single transducer circuit. The controller circuit, also powered from the power recovery and conditioning circuit, controls the data bits to be sent to the external unit, and operation of the TX and/or the multiplexer circuit, and/or also senses analog signals (e.g. frequency, amplitude, phase, timing) and digital bits to control the TX and/or multiplexer circuit. For the above FIG. 33, and all the following FIGS. 34-45, unless specified otherwise, a connection shown between different blocks can comprise a single wire or more wires (e.g. a bus of data signals) as is common in the art. In some embodiments, the multiplexer circuit comprises elements or circuits that are shared between the power and data paths.

Figure 34:
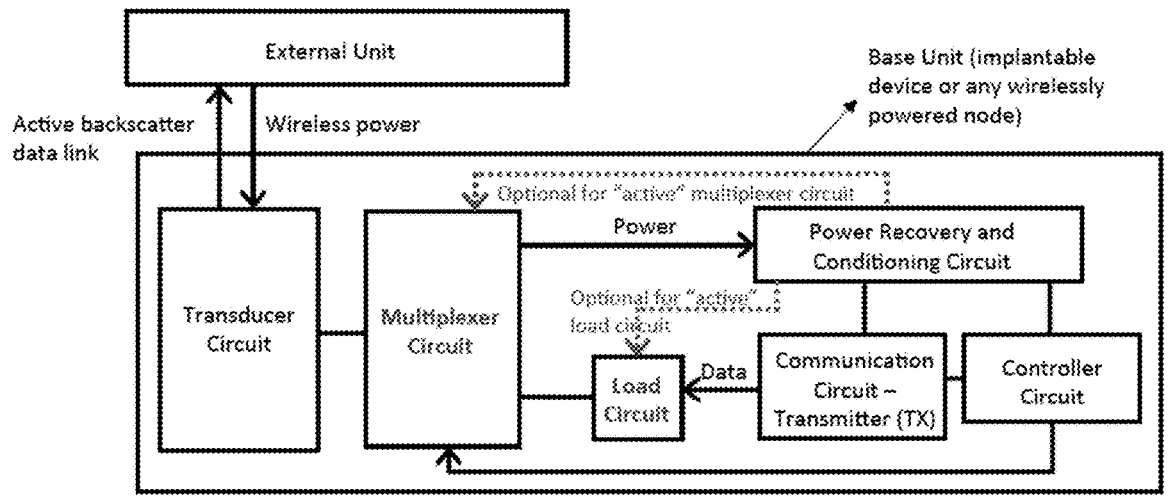
FIG. 34 shows a schematic drawing of a wirelessly powered device having a single transducer power recovery and "active backscatter" uplink data communication, according to one embodiment of the invention.

Regarding a single transducer for wireless power and active backscatter transmission, FIG. 34 is directed to a wirelessly powered device wherein a single transducer is used for power recovery and "active backscatter" data communication. In some embodiments, the same transducer is also used for downlink data communication, or sensing, or stimulation, or a combination of these functions. These embodiments are enabled by the several implementations discussed in the current disclosure. In FIG. 34, the functions of the transducer circuit, multiplexer circuit, power recovery and conditioning circuit, and the controller circuit are the same as described in FIG. 33. Note that "active" backscatter communication refers to the scenario where power recovered by the base unit is used to control the multiplexer circuit, as shown in FIG. 34, and represented by the presence of the Power Recovery and Conditioning Circuit on the base unit, which provides power to the Controller Circuit, which, in turn, controls the operation of the Multiplexer Circuit. The communication circuit-Transmitter (TX), powered from the power recovery and conditioning circuit, modulates the load circuit in order to change the electrical loading or impedance seen by the transducer circuit. The load circuit comprises an electrical load that is either connected directly to the transducer circuit (i.e. the multiplexer circuit comprises wires in certain embodiments), or is connected to the transducer circuit through a multiplexer circuit. The load circuit is modulated by the TX based on the uplink data to be sent to the external unit. In certain embodiments, the load circuit is "active", i.e. it is powered from the power recovery and conditioning circuit. Advantages over using different transducers for power recovery/data downlink and data uplink are the base unit can be significantly miniaturized if a single transducer is used for power recovery and bi-directional data communication (uplink and downlink). For instance, in the case of ultrasonic power/data transfer for implantable devices, this can enable miniaturization of implants to millimeter or sub-millimeter dimensions. This enables the base unit to be biocompatible, low cost, reduced in complexity, the optimization of a single link for power and data, provides for single modality, single transducer, and offers enhanced reliability.

The invention offers further advantages over passive backscatter communication, where in passive backscatter communication, the load presented to the transducer circuit is modulated passively by a sensor, or other circuit, without the use of recovered power or stored energy on the wireless node. In contrast, the current invention recovers energy at the base unit, hence, the base unit has an energy storage element (e.g. battery or capacitor) and can, thus, transmit "active" uplink or backscatter signals. In this configuration, power conditioning and/or storing energy at the implant allows multiple functions for the implant (e.g. sensing, stimulation, data communication, delivery, etc.) in comparison to implants that do not perform any power conditioning and use passive backscatter for communication. Passive backscatter communication has inherent drawbacks because of its limited processing capabilities.

With active backscatter communication power and data can be tuned and independently controlled (time-interleaved), whereas a passive system optimized for efficient power recovery will not be optimal for backscatter and vice versa. For instance, the transducer circuit will typically be impedance matched to the power recovery and conditioning circuit for minimizing reflected power, which will inherently reduce the backscattered signal. Active backscatter allows the use of power recovered by the base unit to decouple the operations of power recovery and backscatter data communication such that both operations are optimized independently, e.g. these operations can be time-multiplexed, wherein the switches used for decoupling these paths are operated using the recovered power or stored energy on the base unit.

Active backscatter communication provides the ability to mitigate power-sensing interference, whereas, in passive backscatter, the incoming interrogation signal from the external unit can interfere with the sensor operation. e.g. for an ultrasonically powered pressure sensor implant, the incoming ultrasound signals can corrupt or saturate the pressure sensor readings. This is avoided with the current invention by separating the sensing and uplink data communication operations in time in certain embodiments. Further, the current invention enables multi-access (TDMA), whereas, in passive backscatter, there will be collision or interference between the data signals from different nodes when the external unit interrogates multiple nodes at the same time. Conversely, by using the recovered power or energy stored on the base unit, signals from different base units can be differentiated from each other in terms of amplitude, or phase, or even frequency, according to embodiments of the current invention.

In other embodiments, the invention enables one to sense the present ultrasound power and judge when to send data, where the same ultrasound transducer can be used as a sensor for sensing the presence of ultrasound. The invention enables one the ability to tune the power and modulation of uplink data signals, where this is fixed for backscatter in a given use scenario (for a given implant design, depth of operation, power level originally transmitted by external unit). This, in turn, allows for optimization over all depths: large depths (even >10 cm), less power for shallow depths. It also enables closed-loop tuning of the power level of the uplink data signals. Further, multi-modulation scheme for downlink/uplink is enabled, where active uplink data transmission allows the modulation scheme used for uplink data transmission (implant to external unit) to be different from that used for downlink data transmission (external unit to implant) in order to mitigate interference, e.g. the external unit can transmit ASK data, implant can transmit FSK. Here, active backscatter is better than passive backscatter because it offers more complex tuning of the electrical loading of the transducer circuit by using the power recovered by the base unit. This helps with improving the signal-to-noise ratio of the backscattered uplink signal.

Turning now to the multiplexer circuit shown in the figures. The multiplexer circuit can include circulators—conventional magnetic circulators, or non-magnetic circulators, including but not limited to active circulators. Power and data uplink/downlink can be at the same frequency or at different frequencies. For frequency selection, impedance and aperture vs frequency characteristics of the transducer circuit can be configured with the goal of decoupling power and data signals by operating at different frequencies according to the dimensions of the transducer, packaging and loading, and the materials used. Considerations are made with respect to the operation at different resonance frequencies of the transducer, the use of harmonics or off-harmonic operation—less effect of non-linearities on interference, and operation in the inductive band.

According to the invention, the Multiplexer Circuit can include fixed or re-configurable matching network(s) or filter(s). In certain embodiments, the multiplexer circuit can include active filter circuits powered through the power recovery and conditioning circuit, which may include an auxiliary low power path. The multiplexer circuit can include passive devices (e.g. a diode, relay, MEMS circuit, blocker, or a passive switch). The multiplexer circuit can also include transmit/receive switches, where the device is configured to perform handshake to determine once VDD (i.e. a reliable DC supply voltage) is established at the base unit, and then do data communication. For example, the external unit transmits a short US signal to look at the state of the implant and then ask if it is ready. When there is no VDD, depletion-mode transistors, or other passive devices, can be used to implement switches. For the logic to drive the switches, envelope detectors, sensor data, or a low power oscillator can be used. For amplitude selection, power and data signals can be differentiated at the implant by the difference in their amplitude, e.g. signals above 3 V can be considered to be power signals and the power recovery path can be turned on when the voltage on the transducer is >3 V, whereas if the signal is smaller, the data recovery path can be turned on. For timing control, fixed or re-configurable time slots for power and data transfer are used, or a handshake is used to determine the state of the base unit and then do power and/or data transfer accordingly. For frequency selection, the controller circuit can include a frequency detector circuit, which detects the frequency of the incoming signal to distinguish between power and downlink data. In some embodiments, the multiplexer circuit is closed loop, while in other embodiments, the timing of the power/data is conveyed by the external source. In some embodiments, the multiplexer circuit includes a calibration circuit to subtract the power and/or TX signals from the total signal on the transducer circuit in order to extract the incoming data signal. In some embodiments, the multiplexer circuit includes wires that directly connect the transducer circuit to the power recovery and conditioning circuit and the load circuit. Some implementations of the above embodiments are time-interleaved while some have simultaneous data/power. In order to prevent breakdown of circuits on the base unit, clamps and protection circuits are appropriately added in all implementations.

Turning now to implementation of the multiplexer circuit for active backscatter communication. In some embodiments, the multiplexer circuit includes wires that directly connect the transducer circuit to the power recovery and conditioning circuit and the load circuit. In other embodiments, the multiplexer circuit can be implemented in any one of the ways discussed above. In one example, the invention allows the use of power recovered by the base unit to decouple the operations of power recovery and backscatter data communication such that both operations can be optimized independently, e.g. these operations can be time-multiplexed, wherein switches used for decoupling the power and data paths are operated using the recovered power or stored energy on the base unit. In certain other embodiments, different frequencies are used to enable the power recovery and backscatter data communication paths.

For implementation of the load circuit, in some embodiments, the load circuit is a single transistor with its drain and source connected between the transducer circuit's terminals, and gate connected to the TX. In some embodiments, the load circuit can comprise any circuit having transistors, or resistors, or capacitors, and/or switches, or any combinations of these elements, controlled/driven by the TX. The load circuit can also comprise N switches (N>1) and different inter-connected loads. The TX can drive these N switches resulting in $2^N$ combinations of states of the load circuit. These states can be used to implement different modulation schemes such as quadrature phase shift keying (QPSK), quadrature amplitude modulation (QAM), etc., where N represents the number of bits per symbol. In some embodiments, the power recovery and conditioning circuit itself serves as the load circuit. Active backscatter data link is used to transmit data about energy stored on the implant based on the change in input impedance of the power recovery and conditioning circuit due to charging of an output capacitor, e.g. this input impedance is small initially, and large when the capacitor is fully charged (actual values depend on implementation). This is useful for closed-loop power control, and/or handshake between the external unit and the base unit to determine time slots for power transfer/data communication. For the different states of the load circuit, any of the load circuit implementations above can be controlled by the TX to present the following loads to the Transducer Circuit for representing "0" and "1" bits: short or an open load, matched or an open load, and matched or a short load.

Figure 35:
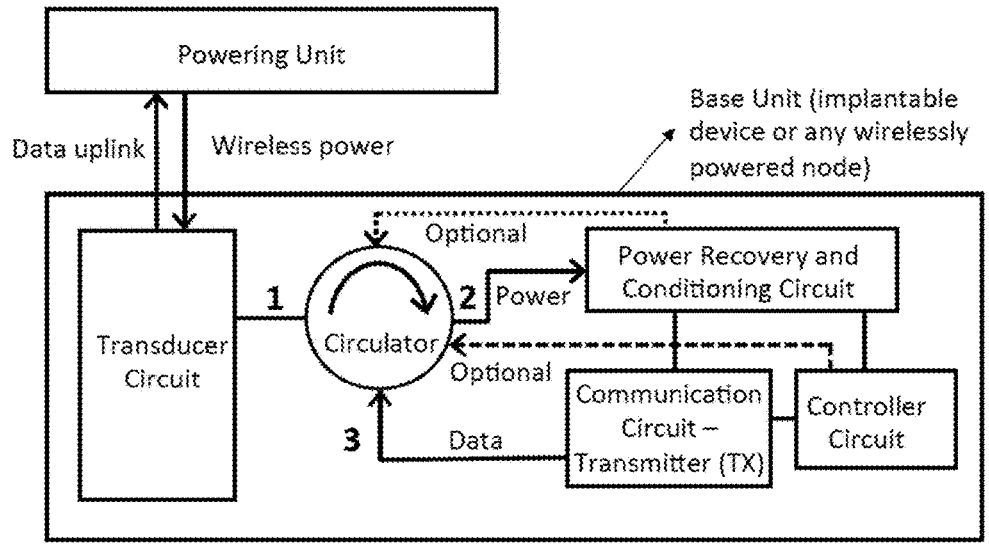
FIG. 35 shows a schematic drawing of the system where the multiplexer circuit comprises a circulator, according to one embodiment of the invention.

For implementations of the multiplexer circuit, in one embodiment the multiplexer circuit comprises a circulator wherein the power signal entering port 1 only exits port 2, and the data signal entering port 3 only exits port 1, as shown in FIG. 35. In some embodiments, the circulator is a passive circulator or active circulator, where when the circulator is an active circulator it includes at least one transistor. In some embodiments, the circulator has one or more active components that are powered from the power recovery and conditioning circuit (represented by the dotted arrow in the figure). This could be done in order to improve the isolation characteristics of the circulator. In other embodiments, the circulator can also be controlled by the controller circuit, as represented by a dashed arrow in the figure. This could also be done in order to improve the isolation characteristics of the circulator, or to control the timing of power transfer and data communication.

Turning now to frequency selection, as discussed earlier, the dimensions, materials and mechanical loadings of an ultrasound transducer can be designed in order to achieve a certain impedance and aperture vs frequency profile. The resonance frequencies (short and open circuit frequencies) can be tuned according to embodiments of the invention. This can also be done for other types of transducers such as RF antennas, inductive coils, etc. Different operating frequencies are then chosen for power transfer, and uplink/downlink data communication. Power, downlink data and uplink data can be transmitted at different resonance frequencies of the transducer circuit to prevent interference, e.g. power can be transmitted at 1 MHz and data at 2 MHz. Power and data can be transmitted at off-harmonic frequencies to prevent interference due to non-linearity of the channel, for example power can be transmitted at 1 MHz and data can be transmitted at 1.6 MHz (not an integer multiple of 1 MHz). Power and data can also be transmitted at intermediate frequencies in the inductive band of the ultrasound transducer. Open circuit ($f_{oc}$) and short-circuit ($f_{sc}$) resonance frequencies of a piezoelectric receiver in the length expander bar mode as discussed above and shown in FIGS. 30-32 as an example of designing an ultrasound transducer to achieve a certain impedance and aperture vs freq profile.

Figure 36:
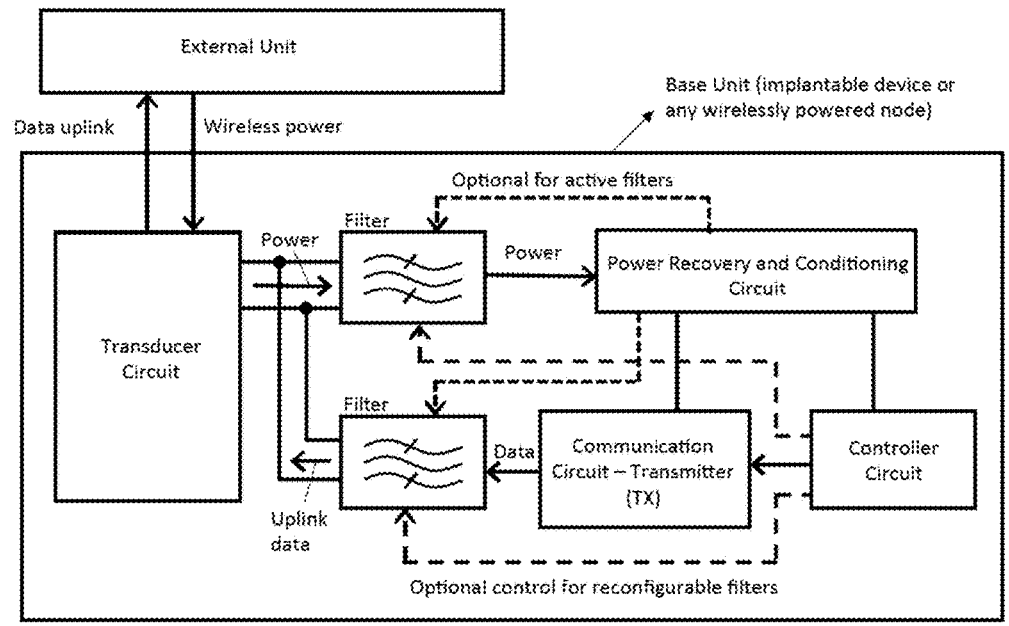
FIG. 36 shows a schematic drawing of an example of filters (fixed frequency or re-configurable) used for implementing the multiplexer circuit, according to one embodiment of the invention.

Further, the multiplexer circuit includes fixed or re-configurable matching network(s) or filter(s) for power and data paths such that power signals only flow through the power path, etc. In the case of operation in the inductive band of the ultrasound transducer, fixed and/or re-configurable capacitive matching networks are used for impedance matching or filtering. The filters can be implemented using components such as resistors, capacitors, diodes, transistors, or any combinations of these circuit elements. In some embodiments, inductors can also be used in the filters. In some embodiments, the filters comprise only capacitor(s), and the ultrasound transducer is operated in the inductive band. The filter may comprise a single capacitor connected in series or shunt with the ultrasound transducer. Also, the filter may comprise a network of capacitors, such as in the form of an L-match, T-match, or pi-match, or any other topology. In certain embodiments, the filter is re-configurable and is controlled by the controller circuit. The controller circuit can tune values of components in the filter, thereby controlling the cut-off frequency or cut-off frequencies, or the roll-off of the filter(s). In other embodiments the filter can be an active filter, which is powered by the power recovery and conditioning circuit. In this case, the active filter operates as a passive filter during startup (which could be achieved through the use of depletion mode transistors in some cases) when there is no recovered power on the implant. Once the implant recovers some power, the active parts of the filter can be powered from the power recovery and conditioning circuit. FIG. 36 shows an example of filters (fixed frequency or re-configurable) used for implementing the multiplexer circuit.

Figure 37:
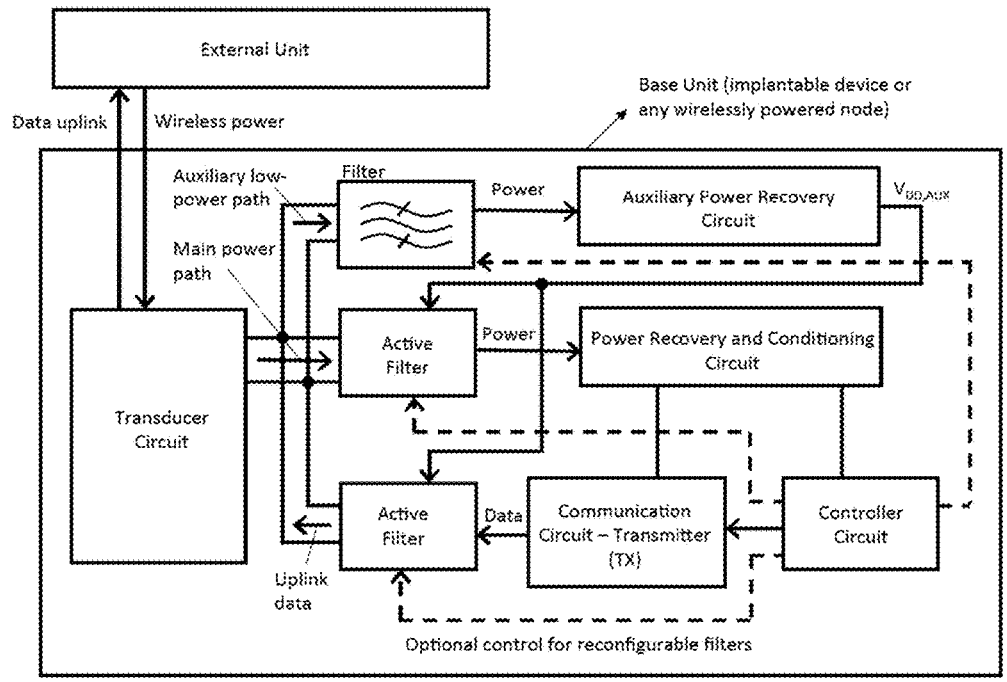
FIG. 37 shows a schematic drawing where the power recovery and conditioning circuit also includes a low-power auxiliary power path to power the active filters, according to one embodiment of the invention.

In some embodiments, active filters are used for frequency selection, wherein the power recovery and conditioning circuit also includes a low-power auxiliary power path to power the active filters, as shown in FIG. 37. In this embodiment, the power recovery and conditioning circuit have a low-power auxiliary path and a high-power main path. A filter (which can be active or passive) allows the power signal to enter the auxiliary power recovery circuit which generates an auxiliary DC voltage rail ($V_{DD,AUX}$). Active filters can enable superior isolation in frequency between the power and data paths as compared to passive filters. Roll-offs of 40 dB/decade, 60 dB/decade and higher can be achieved. Active filters are used in the main power path and the data uplink path. These active filters are powered from $V_{DD,AUX}$. The active filters can include circuits such as active RC filters, gm-C filters, or switched capacitor filters. The power consumption of these active filters is low (<100 uW) and it is therefore feasible to power them from the low-power auxiliary path. In comparison to this, the power in the main power path can be high (~a few mWs). Other circuits may or may not be powered from the auxiliary low-power path.

Figure 38:
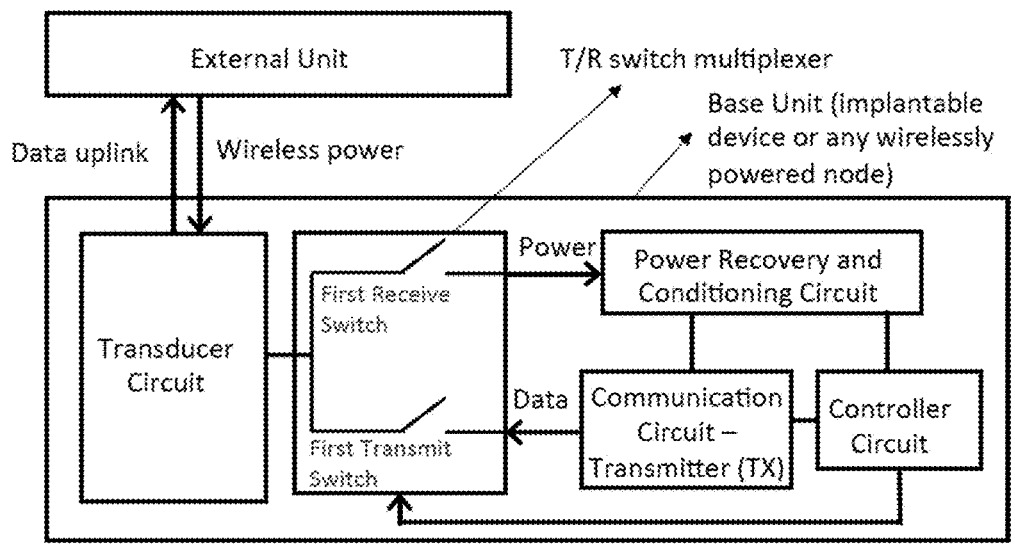
FIG. 38 shows a schematic drawing of T/R switch blocks inserted into the data TX, and power paths to open/close paths, according to one embodiment of the invention.
Figure 39:
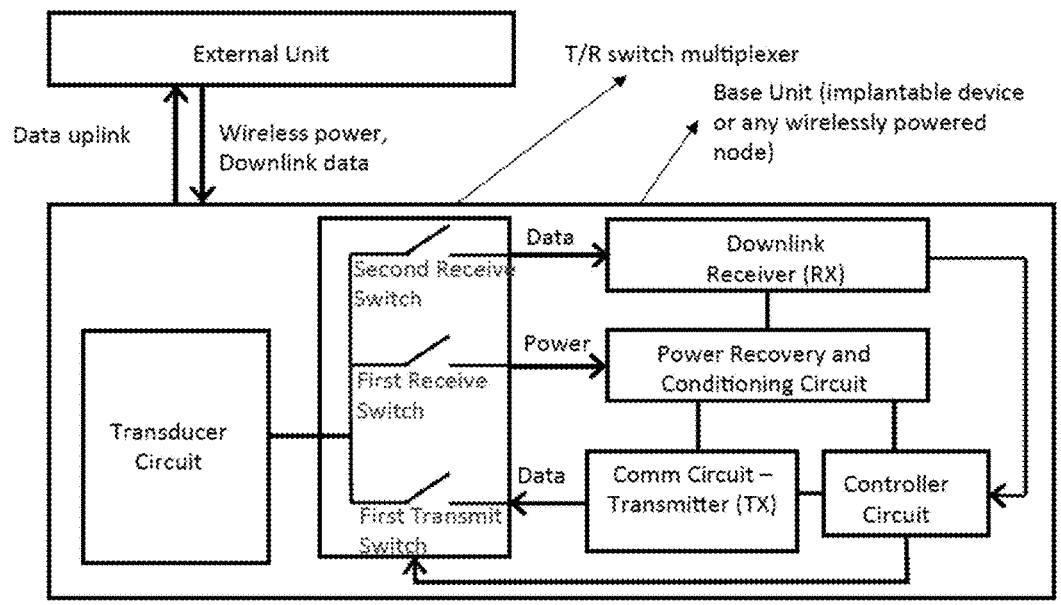
FIG. 39 shows a schematic drawing where T/R switch multiplexer circuit is used for decoupling downlink data, uplink data and power recovery paths, according to one embodiment of the invention.

Turning now to the Transmit/Receive (T/R) Switches. "T/R switch blocks" can be inserted into the data TX, data RX, and power paths to open/close paths as shown in FIG. 38. The switch blocks can include one or more actual switches (e.g. single transistor, transmission gate switch, bootstrap switch, etc.), and could also be implemented using passive devices like a relay or diode. Depletion-mode transistors can be used to implement switches that are "on" without bias—requires a voltage bias to turn off—this is opposed to typical transistors. The transmit switch (labeled as 'First Transmit Switch' in FIG. 38) allows the TX to drive the transducer circuit with data signals/bits. The receive switch (labeled as 'First Receive Switch' in FIG. 38) allows power to flow from the transducer circuit to the power recovery and conditioning circuit. In most embodiments, the T/R switches would be driven by a controller circuit, where the controller circuit is responsible for determining when and which switches to open/close.

The controller circuit may contain logic circuits that open/close the different paths based on timing, where the controller circuit could take inputs from other blocks such as the power recovery and conditioning circuit or communication circuit. The controller circuit could also be signaled by a sensor on the base unit, such as switching on the data TX path to transmit data when some event is detected or measured by the sensor.

The T/R multiplexer itself may be amplitude, frequency, timing, current directionally, or phase selective, for example one path may only be on if the transducer voltage or current amplitude reaches a certain threshold, or it could have multiple thresholds. Alternatively, blocking diodes can be used to allow current flow in only one direction Additionally, the controller circuit may be externally controlled by the external unit if the implant has data downlink capability, where the incoming signal could contain data bits, frequencies, amplitudes, timing, or phases which encode data to control the T/R multiplexer. Further, the external controller could control the multiplexer in real-time or send some commands pre-programming the control circuit and multiplexer for a duration of time following the control signals, for example send a control command dictating the switches for the next 1 millisecond.

The downlink data could be directly pulled from the power path or a separate path could be switched for the downlink data (see FIG. 39), where with many implants according to the current invention, the power and data downlink are in the same path. To implement these various functions, the controller circuit may contain different detector/demodulator circuits such as data demodulation circuits, envelope detectors, frequency detectors, timing circuits, notch detectors, which can interpret incoming signals and properly switch the correct paths.

Figure 40:
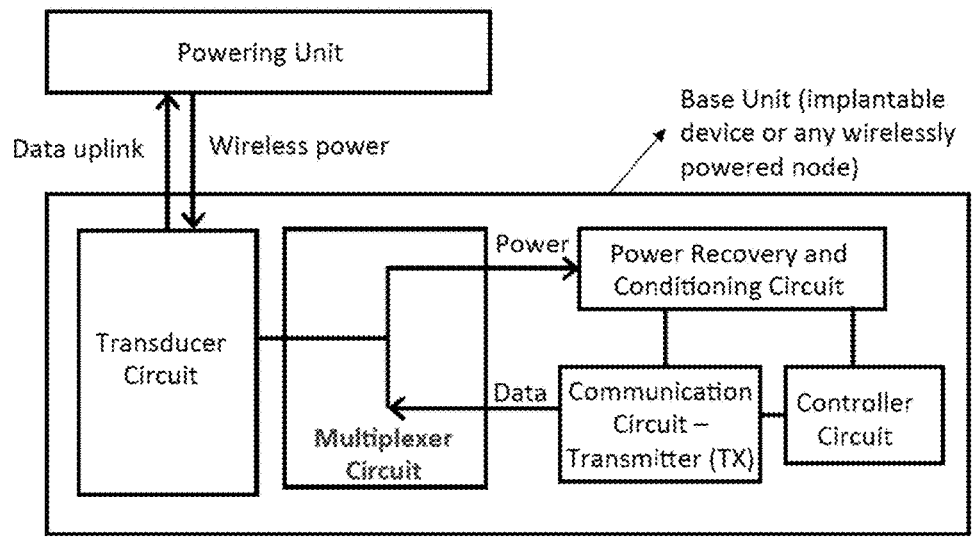
FIG. 40 shows a schematic drawing where the multiplexer circuit comprises direct wired connections, according to one embodiment of the invention.

For direct connections using wires, in this implementation, the multiplexer circuit includes wires connecting the transducer circuit to the power recovery and conditioning circuit and to the transmitter (TX), as shown in FIG. 40. This implementation can be used in a case where the output impedance of the TX is inherently very large (e.g. 10 times large) compared to the input impedance of the power recovery circuit for incoming power signals. Due to this, the TX does not significantly load the power recovery and conditioning circuit during power recovery operation. Also, the impedance of the transducer circuit is small compared to the input impedance of the power recovery circuit (e.g. <10 times small) such that when the TX is transmitting data, it is not significantly loaded by the power recovery and conditioning circuit. Further, this implementation can be used in scenarios where the power recovery and conditioning circuit and the TX have inherent breakdown protection circuits and/or isolation circuits, such that they do not interfere with each others operation. For instance, if the power recovery and conditioning circuit is implemented using a passive rectifier (i.e. using passive diodes), it will prevent reverse discharge of the rectifier output when low-amplitude data signals (i.e. amplitude<rectifier output voltage) are being transmitted by the TX through the transducer circuit. Similarly, in certain implementations, the TX can include an isolation circuit, such as a diode, which prevents reverse current into the TX during power recovery, thereby, preventing any breakdown and avoiding loading effect of the TX on power recovery.

Figure 41:
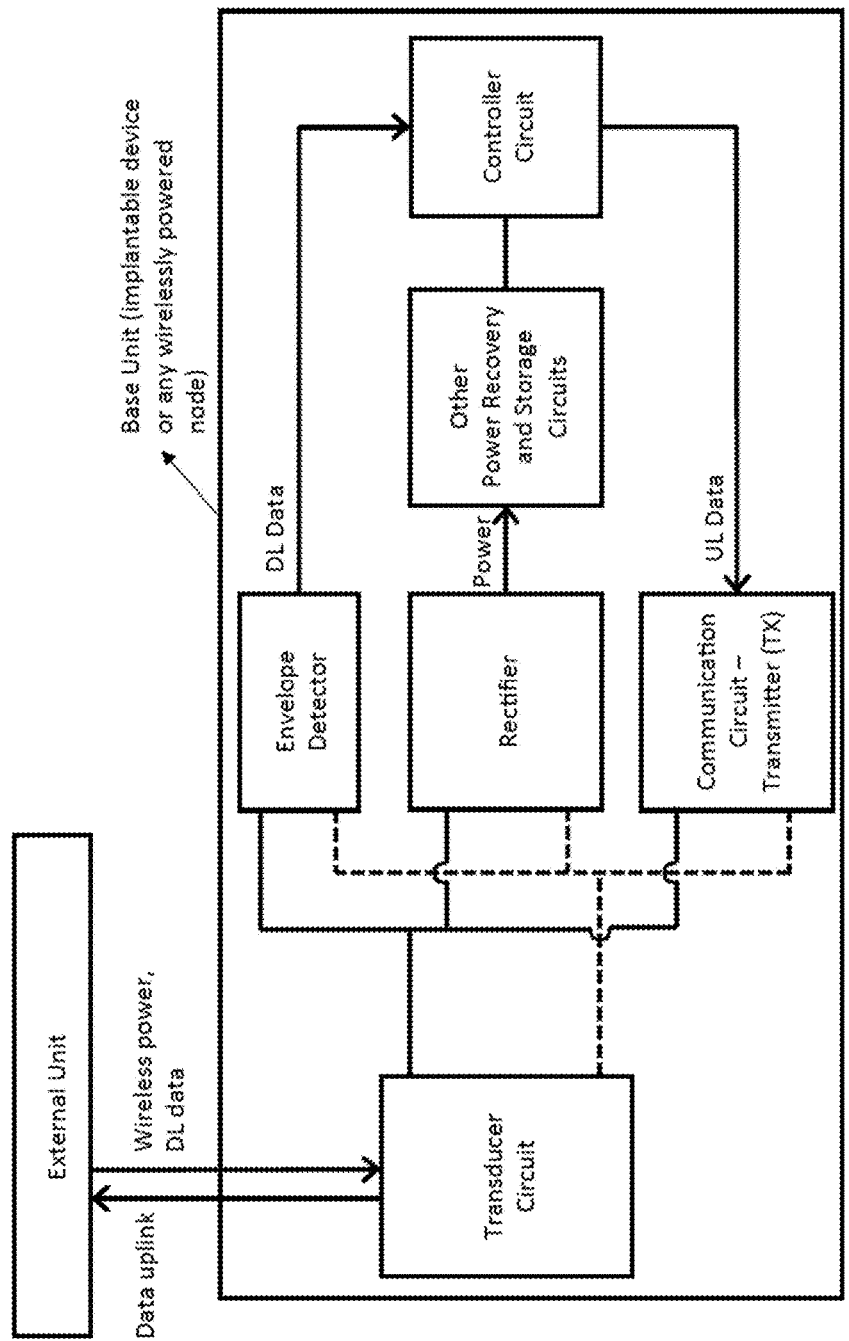
FIG. 41 shows a schematic drawing of an example implementation where the multiplexer itself may share components or blocks with the power recovery and conditioning circuit or the data communication circuit, according to one embodiment of the invention.

For multiplexer combinations, in some embodiments, more than one of the multiplexers can be used or combined. In addition, in some cases, the multiplexer itself may share components or blocks with the power conditioning circuit or the data communication circuit, where an example circuit is shown in FIG. 41. Here, a combination of the multiplexers (T/R switch+filter+amplitude−selection) and some circuits are part of the multiplexer circuit and the other blocks (power and data). In this example, the carrier wave is used for powering, while the envelope is used for data downlink (ASK), the transmitter circuit drives the transducer with a voltage smaller than the input carrier. The rectifier circuit operates as a switch for the power path (i.e. will only charge if input voltage is higher than stored voltage) and ignores the transmitter voltage signals, while also functioning as part of the power conditioning and recovery circuit. The envelope detector circuit acts as a type of filter which can demodulate the envelope of the incoming power/DL data. The communication circuit transmits at a voltage below the rectifier threshold and has internal diodes to prevent reverse currents from the power signal. Further, the rectifier and TX can have diodes that prevent reverse currents. During power-up the diode in TX prevents power from transducer circuit from entering the TX. The rectifier prevents any reverse current from discharging its output voltage. TX is designed to transmit a voltage that is lower than the rectifier output voltage. The rectifier acts as an amplitude-selective power path by ignoring the small TX output voltage. The downlink data path includes an envelope detector which acts as a low-pass filter (frequency selection).

According to other embodiments of the invention, different base units include sensing, and/or stimulation added to the base unit, and they can also interface to the multiplexer. Additional blocks and features to the base unit include downlink data blocks which can be used to process commands from external unit, an auxiliary low power path which can be used for quick power up to enable features before the main power path powers up, sensors for sensing applications including temperature, pressure, impedance, chemical, pH, aptamer-based sensing, bio-sensing, electrical or electrophysiological sensing including but not limited to neural, EMG or ECG recording, or detecting biological species such as: proteins, DNA, biomolecules, or biomarkers, etc.), or a stimulator for applications such as electrical, optical, acoustic stimulation, or release of a chemical, a drug or a biological agent. In certain embodiments, each or all of these blocks (i.e. sensors, stimulators, data downlink, and auxiliary low power path) can be included on the base unit.

Figure 42:
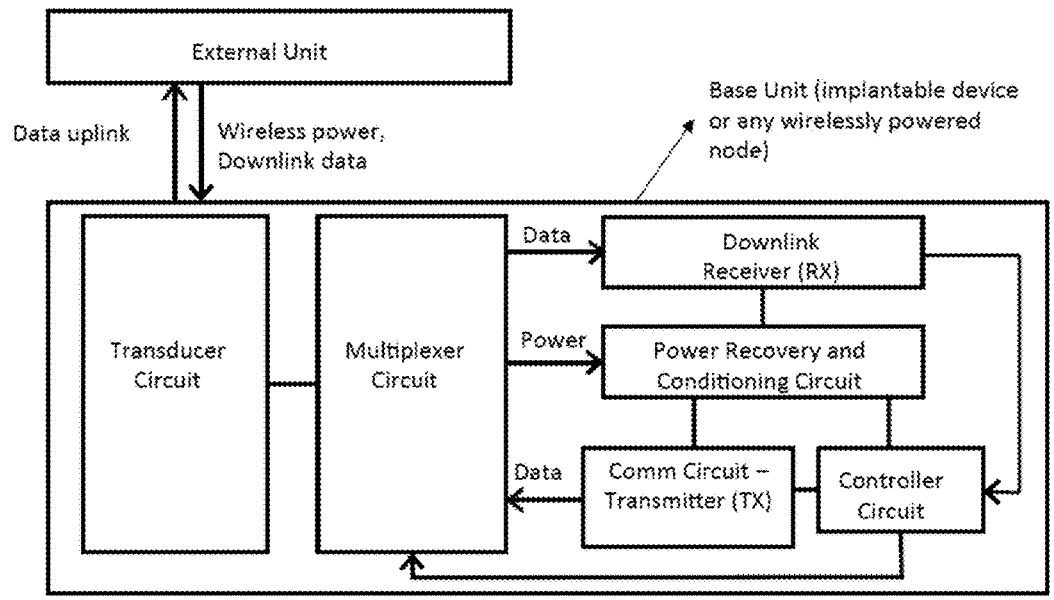
FIG. 42 shows a schematic drawing of a base unit having a downlink data path, according to one embodiment of the invention.

The following figures only show one of the additional blocks added in with the core base unit for simplicity. FIG. 42 shows a base unit having a downlink data path, where a downlink Receiver (RX) interprets incoming commands and relays to the controller circuit. Incoming data can be of any modulation scheme (e.g. ASK, FSK, PPM, etc.) Downlink data can control/program the implant application or also control the multiplexer circuit. Further, the downlink data may have its own "path" in the multiplexer. In some embodiments, the data DL path won't necessarily be in parallel with the power and uplink (UL) path. For example, the DL data may be pulled from the output of the power recovery circuit.

Figure 43:
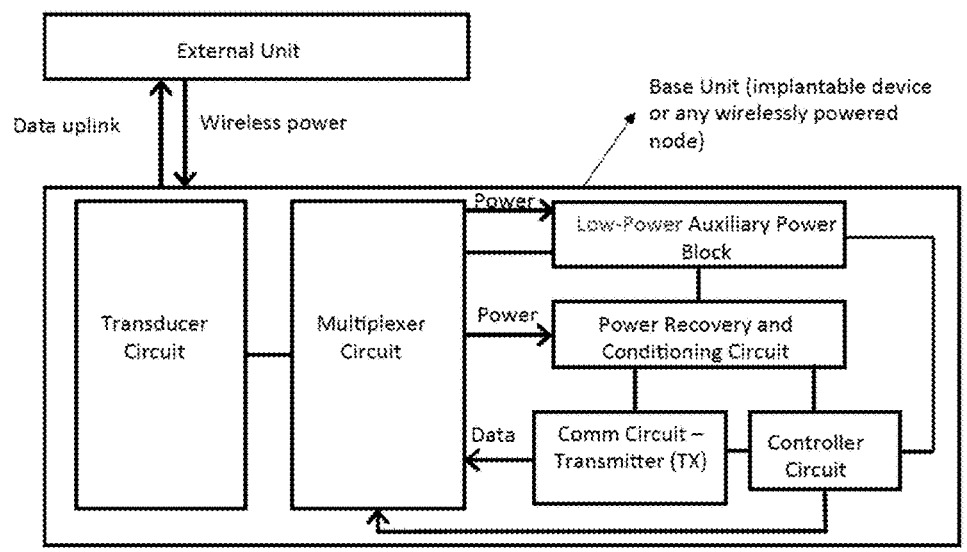
FIG. 43 shows a schematic drawing of the base unit having a low-power auxiliary path, according to one embodiment of the invention.

FIG. 43 shows the base unit having a low-power auxiliary path. In one embodiment, a low power auxiliary power block may be included to quickly power some blocks. The main power path, for example through the power recovery and conditioning circuit, may require longer charging period, so auxiliary power path can be used to perform functions in the meantime. In some embodiments, the auxiliary power path could also be used together with the main power path. The auxiliary power path can have its own "path" in the multiplexer, or the auxiliary power path can be used for powering RX block, multiplexer block, some or all of the controller and power recovery path. Some examples include providing a small amount of power required to switch the multiplexer to route incoming power path and disable data TX path, or providing small power supply required to turn on RX block to parse initial commands.

Figure 44:
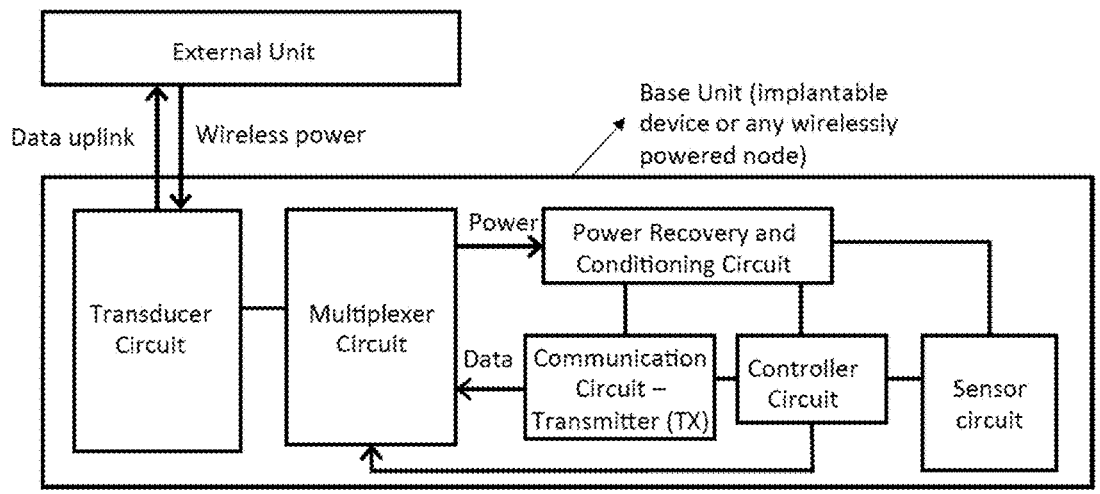
FIG. 44 shows a schematic drawing of a base unit with a sensor circuit, according to one embodiment of the invention.

FIG. 44 shows a base unit with a sensor circuit, such as temperature, pressure, bio-sensor, etc. The sensor circuit includes a sensor and possibly interfacing/conditioning circuits (e.g. amplifiers, filters, comparators, ADC), and the sensor output can also be used to signal the multiplexer, for example the multiplexer state may be changed based on an event sensed by the sensor.

Figure 45:
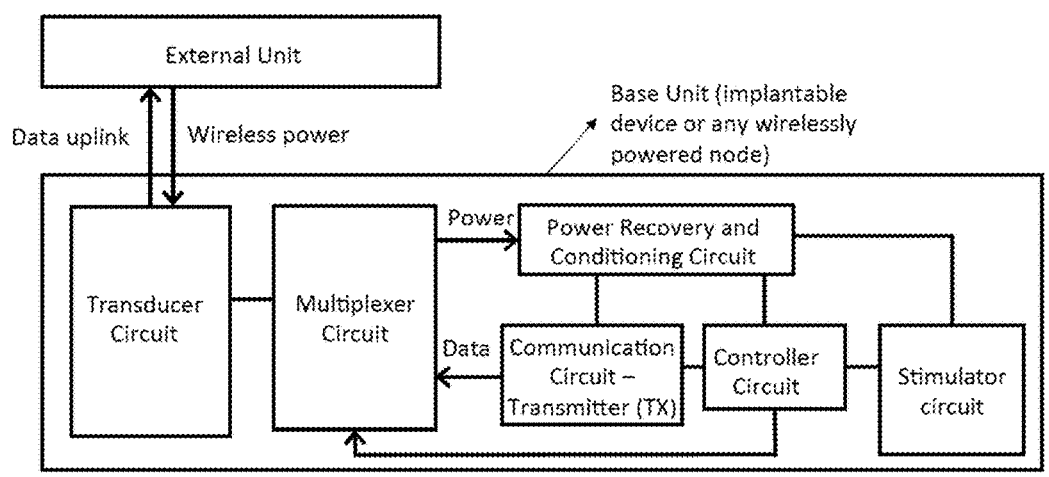
FIG. 45 shows a schematic drawing of the base unit with a stimulator circuit, according to one embodiment of the invention.

FIG. 45 shows the base unit with a stimulator circuit, where the stimulator circuit can include electrical stimulation, optical stimulation, acoustic stimulation, or release of a chemical, a drug, or a biological agent. In one embodiment the stimulator circuit includes a stimulator and possibly interfacing/conditioning circuits (e.g. DAC, current mirrors, amplifiers, etc.). Data downlink could also be incorporated with the system shown in FIG. 45, where the stimulator can be programmed to stimulate according to the downlink data bits. For instance, the downlink data bits can be used to program the stimulation current amplitude and pulse-width for a base unit used for electrical stimulation.

Disclosed herein are the different embodiments of all the blocks in the previous figures except the multiplexer circuit and the load circuit. The external unit can be a wearable device, or a device located external to the body, or another implantable device which is not connected to the base unit through wires, such as subcutaneous, subdural, under the scalp, or under the skin, etc.

The transducer circuit can be an ultrasound transducer such as piezoelectric, capacitive micromachined ultrasound transducer (CMUT) which could either be pre-charged or not, piezoelectric micromachined ultrasound transducer (PMUT), an electro magnetic acoustic transducer (EMAT), and electret for ultrasonic power/data, or an RF antenna for RF power/data, or a coil/inductor for near-field inductive power/data transmission, a photodiode for optical signals, or any transducer that is used to convert a wireless signal into a usable electrical signal.

In some embodiments, the power recovery and conditioning circuit comprises a rectifier circuit which generates a DC voltage rail for powering other circuits on the base unit, wherein the rectifier circuit may comprise a passive rectifier, a passive voltage doubler, a charge pump, or an active rectifier. In some embodiments, the power recovery and conditioning circuit comprises a rectifier circuit and a regulator circuit to generate a regulated DC rail for powering other circuits in the base unit. In other embodiments, the power recovery and conditioning circuit further comprises an energy storage element such as a capacitor or a rechargeable battery to store the harvested energy for use during data communication, or sensing, or stimulation, or any combination of these functions thereof.

The communication circuit-transmitter (TX) comprises an oscillator circuit, or a power amplifier circuit, or a driver circuit, or a combination thereof. These circuits are implemented using designs that are common in the art.

In some embodiments, the controller circuit comprises a finite state machine (FSM) to control the operation of the TX and/or the Multiplexer Circuit. In other embodiments, the controller circuit comprises a signal processor (digital, or analog, or mixed-signal) or a central processing unit (CPU) to process any information and generate the signals required for controlling the operation of the TX and/or the Multiplexer Circuit. In further embodiments, the controller circuit further comprises an encryption processor to perform cryptographic operations for achieving better security in the operation of the base unit and the complete system. According to further embodiments, the controller circuit comprises memory in the form of RAM (e.g. DRAM or SRAM) and/or ROM (e.g. EPROM) or eFUSE.

FIGS. 46A-46C show an example link budget calculation for ultrasonic "active" data uplink, according to the current invention. The current invention provides practical mm-sized (or smaller), implantable US transducers that can achieve higher impedances than RF/inductive sources, with higher impedance facilitating higher voltages, where typical impedances between 100's $\Omega$ to M$\Omega$'s are disclosed, where breakdown (due to over-voltage) is a bigger issue than with lower voltage RF, and impedance loading of non-linear circuits is more important such as overcoming thresholds. The current invention is advantageous for typical implant power levels that include higher received voltages making amplitude selection more practical. Frequency range is between 10 kHz to 30 MHz, where the preferred range is 10 kHz to 10 MHz, and even more preferred range is 300 kHz to 5 MHz specifically for mm to sub-mm-sized US transducers, where for implantable applications typically sizes will be <10 cm$^3$. There are advantages for using a more narrow-band approach that include making a more narrow-band transducer, which will result in smaller tissue losses at low-frequency.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. All such variations are considered to be within the scope and spirit of the present invention as defined by the following claims and their legal equivalents.

What is claimed:
1. A wireless communication system, comprising:
   a) a base unit; and
   b) an external unit, wherein said external unit is separate from said base unit, wherein said base unit comprises:
      i. a single transducer circuit with a single port or feed, wherein said transducer circuit is configured for uplink data communication to said external unit, wherein said transducer circuit is configured for power recovery from said external unit;
      ii. a multiplexer circuit;
      iii. a power recovery and conditioning circuit;
      iv. a controller circuit; and
      v. a communication circuit;
         wherein said multiplexer circuit is configured to decouple power and data paths to enable operation with said single transducer circuit, wherein said power recovery and conditioning circuit is configured to recover and optionally store power from power received by said single transducer circuit, wherein said power recovery and conditioning circuit is configured to power said controller circuit and said communication circuit, wherein said controller circuit is configured to control said multiplexer circuit, wherein said communication circuit is configured to provide data to said multiplexer circuit.

2. The wireless communication system of claim 1, wherein said external unit is configured to detect backscatter signals, wherein said base unit further comprises a load circuit, wherein said load circuit is configured to provide different loads to said transducer circuit during active backscatter communication with said backscatter configured external unit.

3. The wireless communication system of claim 2, wherein said load circuit comprises an active load circuit that is powered from said power recovery and conditioning circuit.

4. The wireless communication system of claim 1, wherein said power recovery and conditioning circuit is configured to power said multiplexer circuit.

5. The wireless communication system of claim 1, wherein said base unit is implantable to a biological host.

6. The wireless communication system of claim 1, wherein said multiplexer circuit comprises a circulator, wherein said circulator comprises a magnetic circulator, a non-magnetic circulator, or an active circulator, wherein said circulator comprises a first port, a second port and a third port, wherein a power signal enters said first port from said transducer circuit, wherein said power signal exits said circulator from said second port and enters said power recovery and conditioning circuit, wherein a data signal enters said third port from said communication circuit, wherein said data signal exits said first port and enters said transducer circuit.

7. The wireless communication system of claim 1, wherein said single transducer circuit comprises a capacitive micromachined ultrasound transducer (CMUT), which could either be pre-charged or not, a piezoelectric micromachined ultrasound transducer (PMUT), an electro magnetic acoustic transducer (EMAT), an electret, a piezoelectric transducer, an RF antenna, a capacitive energy coupler, an inductive coil, or an optical transducer.

8. The wireless communication system of claim 1, wherein said power and data are transmitted at different resonance frequencies, off-harmonic frequencies or intermediate frequencies in an inductive band of said transducer circuit.

9. The wireless communication system of claim 1, wherein said multiplexer circuit comprises a fixed matching network or filter, or comprises a reconfigurable matching network or filter.

10. The wireless communication system of claim 1, wherein said power and data are transmitted at different amplitudes and said multiplexer circuit decouples power and data paths based on said different amplitudes.

11. The wireless communication system of claim 1, wherein said multiplexer circuit comprises a first transmit switch block and a first receive switch block, wherein when transmit switch block is closed, data is communicated from said communication circuit to said transducer circuit, wherein when said receive switch block is closed, power is transferred from said transducer circuit to said power recovery and conditioning circuit.

12. The wireless communication system of claim 11, wherein said first transmit switch block and said first receive switch block are driven by said controller circuit.

13. The wireless communication system of claim 11, wherein said base unit further comprises a downlink receiver circuit, wherein when a second receive switch block is closed, data is communicated from said transducer to said downlink receiver circuit.

14. The wireless communication system of claim 1, wherein said base unit further comprises a sensor, wherein said sensor is configured for temperature, pressure, chemical, pH, impedance, aptamer-based sensing, electrical or electrophysiological sensing including but not limited to neural, EMG recording, ECG recording, or detecting biological species, wherein said biological species are selected from the group consisting of proteins, DNA, biomolecules, and biomarkers.

15. The wireless communication system of claim 1, wherein said base unit further comprises a stimulator circuit, wherein said stimulator circuit is configured for electrical stimulation, optical stimulation, acoustic stimulation, or release of a chemical, a drug or a biological agent.

16. The wireless communication system of claim 1, wherein said multiplexer circuit comprises wires directly connected between said transducer circuit, said power recovery and conditioning circuit, and said communication circuit.

17. The wireless communication system of claim 1, wherein said base unit further comprises a downlink receiver circuit, wherein downlink data is communicated from said multiplexer circuit to said downlink receiver circuit, wherein said downlink receiver circuit receives power from said power recovery and conditioning circuit, wherein said downlink receiver circuit sends data to said controller circuit.

18. The wireless communication system of claim 1, wherein said base unit further comprises a low-power auxiliary power block, wherein said low-power auxiliary power block is configured to recover power from said single transducer circuit before said power recovery and conditioning circuit can fully turn on, wherein said low-power auxiliary power block is configured for partially or fully powering a component selected from the group consisting of said multiplexer circuit, said controller circuit, said power recovery and conditioning circuit, and said communication circuit.

19. The wireless communication system of claim 18, wherein said low-power auxiliary power block is also configured to recover power from said single transducer circuit during the time when said power recovery and conditioning circuit is on.

* * * * *